United States Patent
Holenstein et al.

(10) Patent No.: US 10,707,734 B2
(45) Date of Patent: Jul. 7, 2020

(54) ELECTROMAGNETIC ROTARY DRIVE AND ROTATIONAL DEVICE

(71) Applicant: Levitronix GmbH, Zürich (CH)

(72) Inventors: Thomas Holenstein, Umiken (CH); Reto Schöb, Rudolfstetten (CH)

(73) Assignee: LEVITRONIX GMBH, Zurich (CH)

( * ) Notice: Subject to any disclaimer, the term of this patent is extended or adjusted under 35 U.S.C. 154(b) by 293 days.

(21) Appl. No.: 15/474,453

(22) Filed: Mar. 30, 2017

(65) Prior Publication Data

US 2017/0302145 A1    Oct. 19, 2017

(30) Foreign Application Priority Data

Apr. 14, 2016   (EP) ..................... 16165393

(51) Int. Cl.
*H02K 21/38* (2006.01)
*H02K 21/44* (2006.01)
(Continued)

(52) U.S. Cl.
CPC ............ *H02K 21/38* (2013.01); *A61M 1/101* (2013.01); *A61M 1/1015* (2014.02);
(Continued)

(58) Field of Classification Search
CPC ...... H02K 21/38; H02K 21/44; H02K 19/103; H02K 7/09; A61M 1/105; A61M 1/1031; A61M 1/101; F16C 32/0497
(Continued)

(56) References Cited

U.S. PATENT DOCUMENTS 6,181,040 B1 * 1/2001 Schob ................. F16C 32/0493
                                                                310/103
6,351,048 B1 * 2/2002 Schob ................. F16C 32/0459
                                                                310/90.5
(Continued)

FOREIGN PATENT DOCUMENTS

CN      103825418 A    5/2014
EP      0819330 A1     1/1998
(Continued)

OTHER PUBLICATIONS

Extended European Search Report dated Sep. 19, 2016 in corresponding EP Patent Application No. 16165393.6 (with English Translation of Categories of Cited Documents).

*Primary Examiner* — Michael Andrews
(74) *Attorney, Agent, or Firm* — Global IP Counselors, LLP

(57) ABSTRACT

An electromagnetic rotary drive includes a contactlessly magnetically drivable rotor that is coil-free and free of permanent magnets and that includes a magnetically effective core, and a stator by which the rotor is contactlessly magnetically drivable about a desired axis of rotation in the operating state. The stator has a plurality of coil cores of which each includes a bar-shaped longitudinal limb extending from a first end in a direction in parallel with the desired axis of rotation up to a second end, all the first ends being connected by a reflux of windings generate an electromagnetic rotational field of which each surrounds one of the longitudinal limbs. The coil cores include a plurality of permanent magnets by which a permanent magnetic pre-magnetization flux can be generated.

15 Claims, 23 Drawing Sheets

(51) Int. Cl.
  *A61M 1/10* (2006.01)
  *F16C 32/04* (2006.01)
  *H02K 7/09* (2006.01)
  *B01F 13/08* (2006.01)
  *H02K 19/10* (2006.01)

(52) U.S. Cl.
  CPC ....... *A61M 1/1031* (2014.02); *B01F 13/0827* (2013.01); *B01F 13/0872* (2013.01); *F16C 32/0497* (2013.01); *H02K 7/09* (2013.01); *H02K 19/103* (2013.01); *H02K 21/44* (2013.01)

(58) Field of Classification Search
  USPC .............................................. 310/46, 40 MM
  See application file for complete search history.

(56) References Cited

U.S. PATENT DOCUMENTS

| | | | |
|---|---|---|---|
| 2009/0121571 A1 | 5/2009 | Onuma | |
| 2014/0062239 A1 | 3/2014 | Schoeb | |
| 2017/0040868 A1* | 2/2017 | Noh | .................... F16C 32/0468 |
| 2019/0199186 A1* | 6/2019 | Noh | ...................... H02K 21/20 |

FOREIGN PATENT DOCUMENTS

| | | |
|---|---|---|
| EP | 0860046 A1 | 8/1998 |
| EP | 1063753 A1 | 12/2000 |
| EP | 2065085 B1 | 11/2012 |
| WO | 9631934 A1 | 10/1996 |
| WO | 2012159966 A1 | 11/2012 |

* cited by examiner

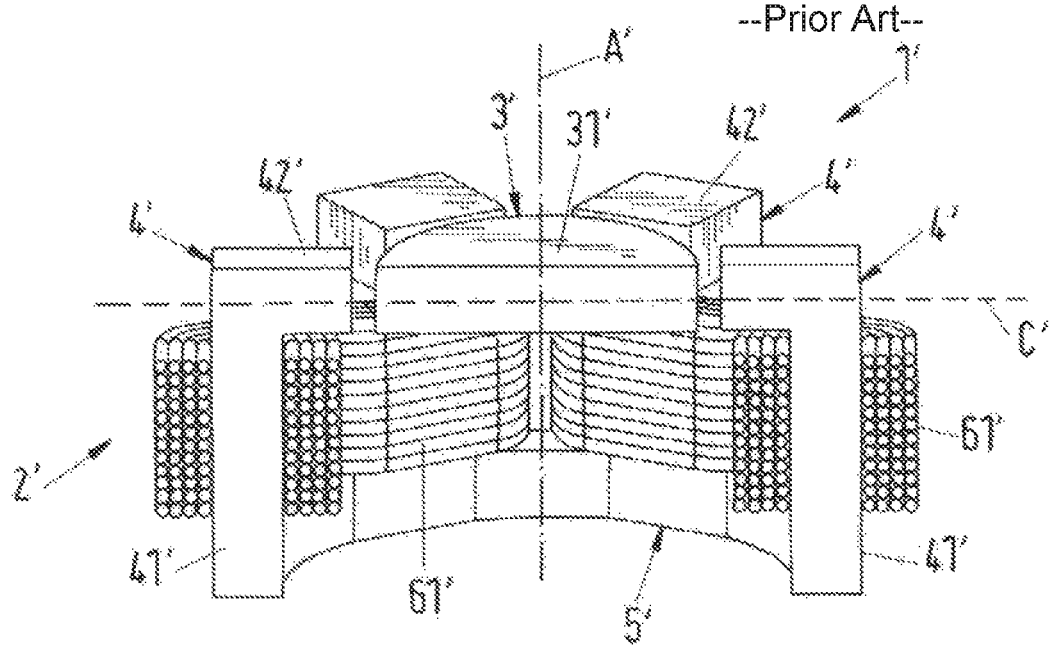

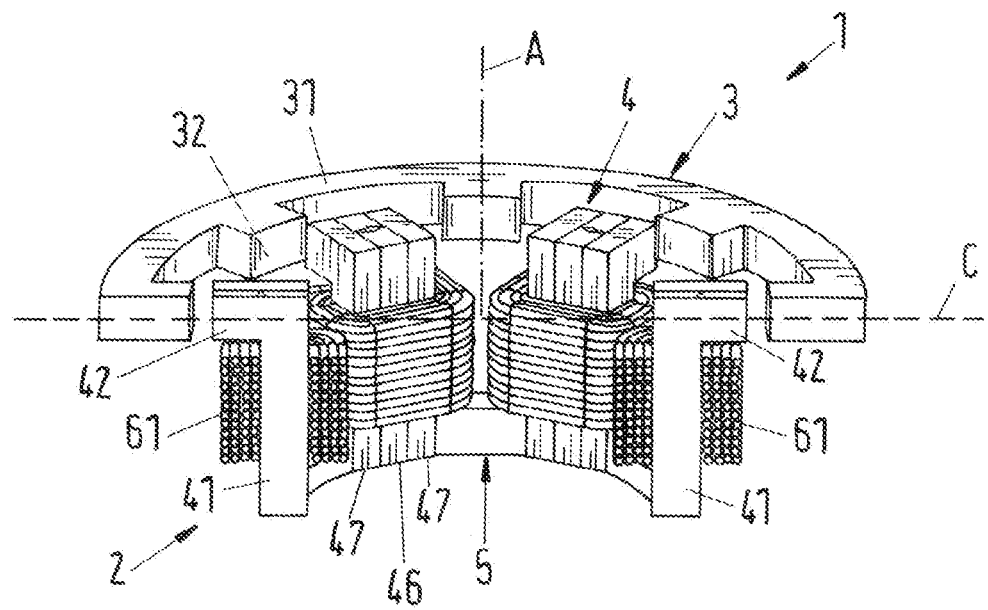
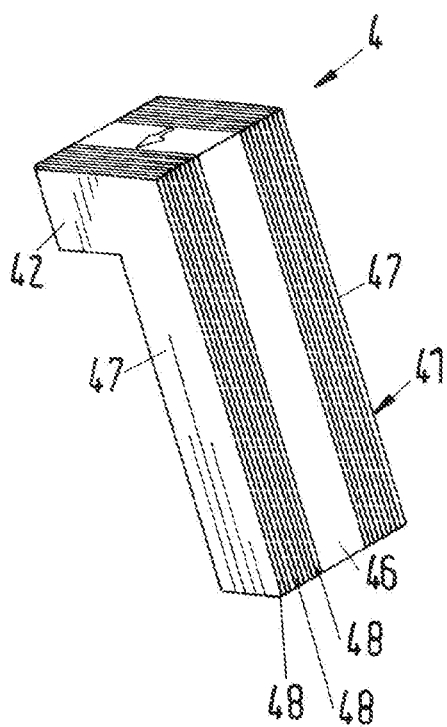
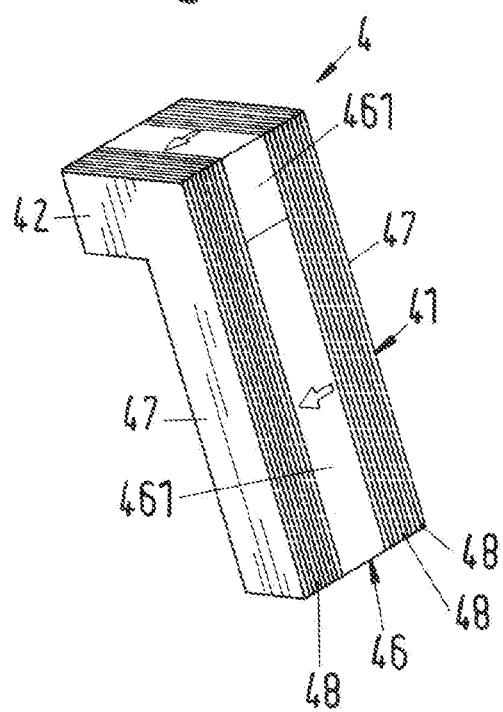

ELECTROMAGNETIC ROTARY DRIVE AND ROTATIONAL DEVICE

CROSS-REFERENCE TO RELATED APPLICATION

This application claims priority to European Application No. 16165393.6, filed Apr. 14, 2016, the contents of which are hereby incorporated herein by reference.

BACKGROUND

Field of the Invention

The invention relates to an electromagnetic rotary drive and to a rotational device.

Background of the Invention

Electromagnetic rotary drives are known that are configured as so-called temple motors. Two embodiments of a temple motor can be seen in respective perspective representations in FIGS. 1 and 2 that are known from the prior art. For better understanding, FIG. 3 shows a section through the temple motor of FIG. 2 in an axial direction. To indicate that the representations in FIGS. 1 to 3 are apparatuses from the prior art, the reference numerals are here respectively provided with an inverted comma or dash. The temple motor is characterized as a whole by the reference numeral 1'.

What is characteristic about a temple motor is that the stator 2' has a plurality of coil cores 4' of which each comprises a bar-shaped longitudinal limb 41' that extends in parallel with the axial direction A'. That direction is in this respect meant by the axial direction A' that is defined by the desired axis of rotation of the rotor 3', that is the axis of rotation about which the rotor 3' rotates in the operating state when it is in a centered and non-tilted position with respect to the stator 2' in the radial plane that is disposed perpendicular to the axial direction. Only the respective magnetically effective core 31' of the rotor 3' that is respectively configured as a disk-shaped permanent magnet is shown of the rotor 3' in FIGS. 1 to 3. The magnetization of the permanent magnet is respectively illustrated by the arrow without a reference numeral.

SUMMARY

Electromagnetic rotary drives are furthermore known which are configured and operated in accordance with the principle of a bearingless motor. The term bearingless motor in this respect means an electromagnetic rotary drive in which the rotor is supported completely magnetically with respect to the stator, with no separate magnetic bearings being provided. For this purpose, the stator is configured as a bearing and drive stator; it is therefore both the stator of the electric drive and the stator of the magnetic support. A magnetic rotational field can be produced using the electrical windings which, on the one hand, exerts a torque onto the rotor which effects its rotation and which, on the other hand, exerts a shear force, which can be set as desired, onto the rotor so that the rotor's radial position can be actively controlled or regulated. The absence of a separate magnetic bearing with a complete magnetic support of the rotor is the property which gives the bearingless motor its name.

The bearingless motor has become sufficiently well-known to the skilled person in the meantime and is used for a number of different applications. Some fundamental descriptions can be found, for example, in EP-A-0 860 046 and EP-A-0 819 330.

Due to the absence of mechanical bearings, the bearingless motor is in particular suitable for pumping, mixing or stirring apparatus with which very sensitive substances are conveyed, for example blood pumps, or on which very high demands are made with respect to purity, for example in the pharmaceutical industry or in the biotechnological industry, or with which abrasive substances are conveyed which would very quickly destroy mechanical bearings, for example pumps or mixers for slurry in the semiconductor industry. Bearingless motors are also used in semiconductor production for supporting and rotating wafers, for example when they are coated or treated with photoresist or other substances.

A further advantage of the principle of the bearingless motor in pumping, stirring or mixing applications results from the design of the rotor as an integrated rotor which is both the rotor of the electromagnetic drive and the rotor of the pump, of the stirrer or of the mixer. In addition to the contactless magnetic support, the advantage results here of a very compact and space-saving configuration.

In addition, the principle of the bearingless motor also allows designs in which the rotor can be very easily separated from the stator. This is a very big advantage since the rotor can thus be designed as a single-use part for single use, for example. Such single-use applications today frequently replace processes in which all those components which come into contact with the substances to be treated in the process previously had to be cleaned and sterilized in a complex and/or expensive manner, for example by steam sterilization, due to the very high purity demands. In the configuration for single use, those components which come into contact with the substances to be treated are only used exactly once and are then replaced with new, that is unused, single-use parts in the next application.

The pharmaceutical industry and the biotechnological industry can be named as examples here. Solutions and suspensions are frequently prepared here which require a careful blending or conveying of the substances.

In the pharmaceutical industry, for example in the production of pharmaceutically active substances, very high demands are made on cleanliness; the components which come into contact with the substances often even have to be sterile. Similar demands also result in biotechnology, for example in the preparation, treatment or cultivation of biological substances, cells or microorganisms, where an extremely high degree of purity has to be ensured in order not to endanger the usability of the product produced. Bioreactors can be named as a further example here in which, for example, biological substitutes for tissue or special cells or other very sensitive substances are cultivated. Pumping, stirring or mixing apparatus are also required here in order, for example, to ensure a continuous blending of the nutrient fluid or to ensure its continuous circulation in the mixing tank. A very high purity has to be ensured in this respect to protect substances or the produced products from contamination.

In such applications, the pumping, stirring or mixing apparatus is then composed of a single-use apparatus and of a reusable apparatus. In this respect, the single-use apparatus comprises those components which come into contact with the substances and which are configured as single-use parts for single use. This is, for example, the pumping or mixing tank with the rotor which is provided therein and which then, for example, comprises an impeller for conveying the substances. The reusable apparatus comprises those components which are used permanently, that is multiple times, for example the stator. Such an apparatus is disclosed, for example, in EP-B-2 065 085.

In the configuration as a single-use part, the pumping or mixing tank is frequently designed as a flexible plastic pouch or as a plastic sack with a rotor contained therein. These pouches are frequently already sterilized during manufacture or after the packaging and storing and are supplied to the customer in sterile form in the packaging.

It is an important criterion for the manufacture or design of single-use parts for single use that they can be assembled in as simple a manner as possible with the reusable apparatus or its components. It is desirable that this assembly can take place with as little effort as possible, with little work, fast and preferably without tools.

Another aspect is that these single-use parts can be manufactured as economically and inexpensively as possible. In this respect value is in particular also placed on reasonably priced, simple starting materials such as commercial plastics. An environmentally aware handling and a responsible use of the available resources are also major aspects in the design of disposable parts.

Such configurations are also known in which the total pumping, stirring or mixing apparatus is configured for single use.

A particularly advantageous embodiment that is known per is to configure the initially described temple motor as a bearingless motor—irrespectively of whether it comprises components for single use or not.

In the embodiments of the temple motor 1' shown in FIGS. 1 to 3, the coil cores 4'-here, for example, six coil cores 4'—are arranged with the bar-shaped longitudinal limbs 41' in a circular manner and equidistantly around the rotor 3' (internal rotor). In an embodiment as an outer rotor, the rotor is e.g. of ring shape and the coil cores are arranged disposed inwardly with respect to the rotor. The plurality of bar-shaped longitudinal limbs 41' that extend in the axial direction A' and that are reminiscent of the columns of a temple has given the temple motor its name.

Every bar-shaped longitudinal limb 41' extends from a first end, at the bottom in accordance with the illustration, in the axial direction A' up to a second end, at the top in accordance with the illustration. The first ends are connected by a reflux 5' in the radial direction, the reflux comprising a plurality of segments that are each arranged between two adjacent coil cores 4'. The permanent magnetic rotor 3' is arranged between the second ends of the longitudinal limbs 41' and rotates about the axial direction A' in the operating state, wherein the rotor 3' is contactlessly magnetically driven and contactlessly magnetically supported with respect to the stator 2', and wherein the radial position of the rotor 3' is regulated such that it is located in a centered position between the second ends of the longitudinal limbs 41'.

The longitudinal limbs 41' bear windings to generate the electromagnetic rotational fields required for the magnetic drive and for the magnetic support of the rotor 3'. In the embodiments shown in FIGS. 1 to 3, the windings are configured, for example, such that a discrete coil 61' is wound around each longitudinal limb 41', that is the coil axis of each coil 61' respectively extends in the axial direction A'. It is typical for the temple motor in this respect that the coil axes of the coils 61' extend in parallel with the desired axis of rotation and that the coils 61' or the windings are not arranged in the magnetic rotor plane C'. The magnetic rotor plane C' is the magnetic center plane of the magnetically effective core 31' of the rotor 3'. It is that plane perpendicular to the axial direction A' in which the rotor 3' or the magnetically effective core 31' of the rotor 3' is supported in the operating state. As a rule and in particular in the embodiment of the magnetically effective core 31' of the rotor 3' as a disk shown in FIGS. 1 to 3, the magnetic rotor plane C' is the geometrical center plane of the magnetically effective core 31' of the rotor 3' that lies perpendicular to the axial direction A'. As FIGS. 1 to 3 show, the coils 61' are arranged beneath the magnetic rotor plane C' and preferably beneath the magnetically effective core 31' of the rotor 3'.

FIGS. 2 and 3 show a frequently implemented embodiment of the temple motor. In this embodiment, each coil core 4' comprises, in addition to the longitudinal limb 41', a transverse limb 42' that is respectively provided at the second end of the longitudinal limb 41' and that extends in the radial direction, that is substantially at a right angle to the longitudinal limb 41'. In this embodiment, the coil cores 4' each have the shape of an L, with the transverse limbs 42' forming the short limb of the L. The rotor 3' is then arranged between the transverse limbs 42'.

One of the advantages of the embodiment as a temple motor is that no windings or winding heads of the stator are present in the magnetic rotor plane C'. This makes it possible, for example in an application of the temple motor in a centrifugal pump, that the outlet of the centrifugal pump can be provided in the plane in which the impeller of the pump rotor rotates, that is the outlet lies at the same level with respect to the axial direction A' as the vanes of the pump rotor, without the windings of the stator interfering in this respect. This central, i.e. middle, arrangement of the pump outlet is particularly favorable under hydrodynamic aspects and specifically with respect to the passive support and stabilization of the rotor against tilts.

Starting from this prior art, it is an object of the invention to provide a different electromagnetic rotary drive which is configured as a temple motor and which can be used for a plurality of applications. The rotary drive should furthermore also be able to be configured for applications using components for single use. In addition, it is an object of the invention to provide a stator for such a rotary drive and to provide a rotational apparatus for conveying, pumping, mixing or stirring that comprises such a rotary drive.

The subjects of the invention satisfying this object are described herein.

In accordance with the invention, an electromagnetic rotary drive is therefore provided that is configured as a temple motor, having a rotor that is contactlessly magnetically drivable, that is configured as coil-free and free of permanent magnets and that comprises a magnetically effective core, and having a stator by which the rotor is contactlessly magnetically drivable about a desired axis of rotation in the operating state, wherein the stator has a plurality of coil cores of which each comprises a bar-shaped longitudinal limb that extends from a first end in a direction in parallel with the desired axis of rotation up to a second end, wherein all the first ends are connected by a reflux, and wherein a plurality of windings are provided for generating an electromagnetic rotational field of which each surrounds one of the longitudinal limbs, and wherein the coil cores comprise a plurality of permanent magnets by which a permanent magnetic pre-magnetization flux can be generated.

It is possible to generate the total magnetic flux in the stator due to the specific embodiment of the stator of the temple motor that comprises permanent magnets in the stator. It in particular hereby becomes possible that the rotor does not contribute to the generation of the magnetic flux, but rather only has to conduct or guide it. It is thus possible to dispense with permanent magnets or magnetically very hard materials for flux generation in the rotor.

The rotor can be produced particularly simply, economically and inexpensively due to the complete omission of permanent magnets in the rotor that contribute to the drive flux or control flux, which in particular also represents a huge advantage for an embodiment as a single-use rotor. Depending on the configuration, different jackets, gaps and walls, in particular a jacket of the magnetically effective core of the rotor, the fluid gap or a separating can which surrounds the stator, are accommodated in the region between the stator and the magnetically effective core of the rotor. In order to accommodate all these elements, a spacing of at least 3 millimeters, better of 4 to 6 millimeters, is preferred between the stator and the magnetically effective core of the rotor. Since the rotor of the rotary drive in accordance with the invention does not have any permanent magnets and thus cannot contribute to the magnetomotive force, the total magnetomotive force has to be produced in the stator. For a spacing of, for example, 3 millimeters between the stator and the magnetically effective core of the rotor, a magnetomotive force of around 5000 amperes is necessary to be able to support and drive the rotor in a reliably magnetic manner. If the stator is excited as customary solely by windings, that is electromagnetically, such a high magnetomotive force is impossible to realize in the mostly tight construction space of the stator with reasonable dimensions. In accordance with the invention, a plurality of permanent magnets are therefore attached in the stator that generate a pre-magnetization flux. However, since neither a rotating field for generating a toque nor a regulable magnetic flux for the active magnetic support of the rotor can be generated with a constant magnetic flux, windings are additionally attached in the stator by which electromagnetic magnetic fluxes are produced which are thus variable and regulable.

It is customary in accordance with today's prior art in particular to use metals of rare earths or compounds or alloys of these metals as permanent magnets in the rotor because very strong permanent magnetic fields can be generated using them due to their magnetic properties. Known and frequently used examples of these rare earths are neodymium and samarium. However, such metals represent a substantial cost factor due to their comparatively small occurrence and due to their complex and/or expensive mining and processing. In addition, the waste disposal of such permanent magnets after a single use, for example, is frequently also associated with problems or a high effort under technical environmental aspects, whereby additional costs arise. It is therefore advantageous under economic, cost and environmental aspects, in particular also in single-use applications, that the invention makes it possible in particular to be able to dispense with such permanent magnet materials consisting of or comprising rare earths in the rotors.

The stator is particularly preferably configured as a bearing and drive stator by which the rotor is contactlessly magnetically supportable with respect to the stator in the operating state. This embodiment in accordance with the principle of a bearingless motor allows a particularly compact embodiment because only a single stator is provided by which both the drive function and the bearing function for the rotor can be implemented.

In a preferred embodiment, each coil core comprises a transverse limb that is arranged at the second end of the longitudinal limb and that extends in a radial direction that is perpendicular to an axial direction defined by the desired axis of rotation. Respective end faces that are disposed opposite the magnetically effective core of the rotor can be formed at the coil cores by these transverse limbs. A particularly favorable conducting of the magnetic flux from the stator into the rotor or vice versa is possible by these end faces of the transverse limbs.

A preferred measure comprises the fact that each coil core comprises a permanent magnetic portion that extends from the first end up to the second end of the longitudinal limb and comprises two permanent magnet-free portions that each extend from the first end up to the second end, wherein the permanent magnetic portion is arranged between the two permanent magnet-free portions. It is possible by this embodiment that the electromagnetic flux paths are guided such that they do not lead through the permanent magnets. Most permanent magnets, in particular rare earth magnets, but also ferrite magnets, have a relative permeability which is only insignificantly above zero. If the electromagnetic flux paths were therefore to lead through the permanent magnet or magnets, the electromagnetically effective air gap would thus increase by the extent of the permanent magnets located in the flux path and would additionally increase the magnetomotive force requirement. It is therefore an advantage if the permanent magnetically excited fluxes and the electromagnetically excited fluxes can be guided so that they superpose one another in the magnetic air gap between the stator and the rotor, but are conducted separately in the region of the permanent magnets. The electromagnetically excited fluxes should preferably be conducted, where possible, through soft magnetic material such as iron or silicon iron except for the region of the air gaps between the rotor and the stator. The air gap fluxes can be modulated by the superposition of the permanent magnetically excited fluxes and of the electromagnetically excited fluxes in the region of the air gaps between the rotor and the stator such that both a regulation of the radial rotor position and the formation of tangential force components, which effect a torque, are made possible.

It is furthermore advantageous if the permanent magnetic portion and the two permanent magnetic-free portions of the coil core each extend through the transverse limb, and wherein the permanent magnetic portion is arranged between the two permanent magnet-free portions in the transverse limb. It is namely hereby particularly easily possible to guide the permanent magnetically excited flux and the electromagnetically excited flux in the stator separately from one another in the sense that the electromagnetically excited flux in this stator does not have to be guided through permanent magnets.

In accordance with a preferred embodiment, the permanent magnetic portion of the coil core has substantially the same cross-sectional surface in a section in the axial direction as one of the permanent magnet-free portions in a section in an axial direction. This measure allows a simple and inexpensive design of the stator in which the permanent magnetic flux can be guided in the stator in a simple manner substantially separate from the electromagnetically excited flux.

A further advantageous measure comprises the permanent magnetic portions each being polarized perpendicular to the radial direction and perpendicular to the axial direction, with the permanent magnets of adjacent coil cores each being polarized in opposite directions. This measure allows a particularly easy and simple regulation of the drive and of the support of the rotor.

In order in particular to minimize eddy current losses in the stator, it is advantageous if the permanent magnet-free portions of the coil cores are each manufactured in bundled laminate form from elements, with the elements being stacked in the peripheral direction of the rotor.

It is preferred for technical regulation reasons if the stator has an even number of coil cores, preferably six or eight or twelve coil cores.

In accordance with a preferred embodiment, the end faces of the transverse limbs of the coil cores facing the rotor have a level in the axial direction that is respectively larger than the axial height of the magnetically effective core of the rotor. A greater or better passively magnetic stabilization of the rotor with respect to tilts with respect to the desired axis of rotation in particular results from this.

In a preferred embodiment, the windings comprise drive coils for generating an electromagnetic drive field for the rotor as well as control coils separate therefrom for setting a transverse force in the radial direction acting on the rotor. In this embodiment, two separate winding systems are thus provided, namely the drive coils by which an electromagnetic rotational field can be generated that effects a torque on the rotor and thus effects its rotation and the control coils by which an additional rotational field can be generated by which the transverse force acting on the rotor, that is a force in the radial direction, can be set. In this respect, the drive coils can be provided on the same coil cores as the control coils or there are coil cores on which only drive coils or only control coils are provided or mixed forms of these two variants are implemented. Either only control coils or only drive coils or both control and drive coils are provided on an individual coil core. This can naturally vary from coil core to coil core within the stator, i.e. the stator can comprise both coil cores that only bear drive coils or control coils and coil cores that bear drive coils and control coils. Viewed from an apparatus aspect, the division into drive coils and control coils separate therefrom has the advantage that a respective separate bipolar power amplifier does not have to be provided for each individual coil to control this coil.

In a preferred embodiment, the magnetically effective core of the rotor is of disk shape or ring shape. The rotor preferably has a radially outer limiting surface that has the same spacing from all the coil cores in the radial direction in a centered state of the rotor. The sensor system required for the control and regulation of the rotor position can be simplified by this measure because the desired spacing of the rotor from the coil cores is a constant value viewed over the periphery of the rotor.

An advantageous measure with respect to the embodiment of the rotor comprises the rotor being configured with flux barriers for the magnetic flux. It is hereby possible that the magnetic anisotropy of the rotor can be set practically as desired and can thus be optimized in a simple manner for the respective application.

A stator is furthermore provided by the invention for an electromagnetic rotary drive that is configured as a temple motor, wherein a rotor can be contactlessly magnetically driven about a desired axis of rotation by the stator in the operating state, wherein the stator has a plurality of coil cores of which each comprises a bar-shaped longitudinal limb that extends from a first end in a direction in parallel with the desired axis of rotation up to a second end, wherein all the first ends are connected by a reflux, and wherein a plurality of windings for generating an electromagnetic rotational field are provided of which windings each surrounds one of the longitudinal limbs, and wherein the coil cores comprise a plurality of permanent magnets by which a permanent magnetic pre-magnetization flux can be generated, wherein each coil core comprises a permanent magnetic portion that extends from the first end up to the second end of the longitudinal limb and comprises two permanent magnet-free portions that each extend from the first end up to the second end, wherein the permanent magnetic portion is arranged between the two permanent magnet-free portions.

It is possible to generate a large portion of the magnetic flux or even the total magnetic flux in the stator by the specific embodiment of the stator for a temple motor that comprises permanent magnets in the stator. It is in particular advantageous in this respect that—as already explained above—the permanent magnets already generate a constant pre-magnetization flux in the stator such that a sufficiently high magnetomotive force is also generated together with the electromagnetically generated flux with a very compact construction of the stator to drive the rotor contactlessly magnetically or to support it contactlessly magnetically. The specific embodiment of the stator with the coil cores that each have a permanent magnetic portion that is arranged between two permanent magnet-free portions makes it possible that the electromagnetic flux paths are guided in the stator such that they do not lead through the permanent magnets. The permanent magnetically excited fluxes and the electromagnetically excited fluxes can thus be guided such that they are superposed on one another in the magnetic air gap between the stator and the rotor, but are guided separately in the region of the permanent magnets of the stator. The electromagnetically excited fluxes should preferably be conducted, where possible, through soft magnetic material such as iron or silicon iron except for in the region of the air gaps between the rotor and the stator.

In a particularly preferred embodiment, the stator is configured as a bearing and drive stator by which the rotor is contactlessly magnetically supportable with respect to the stator in the operating state.

The stator in accordance with the invention is suitable both for temple motors in which the rotor is designed free of coils and free of permanent magnets and for temple motors in which the rotor comprises permanent magnets and/or coils.

A rotational apparatus for conveying, pumping, mixing or stirring fluids is furthermore proposed that comprises an electromagnetic rotary drive or stator that is configured in accordance with the invention.

The rotational apparatus in accordance with the invention can in particular also be configured such that it comprises components for single use. In this embodiment, the rotational apparatus preferably has a single-use apparatus that is configured for single use and a reusable apparatus that is configured for multiple use, wherein the single-use apparatus comprises at least the rotor that has a plurality of vanes for conveying, pumping, mixing or stirring the fluid or fluids, and wherein the reusable apparatus comprises a support tank for receiving the rotor and comprises the stator by which the rotor can be contactlessly magnetically driven and supported in the operating state, wherein the stator comprises at least one permanent magnet for generating a permanent magnetic pre-magnetization flux and comprises at least one winding for generating an electromagnetic flux, and wherein the permanent magnetic pre-magnetization flux and the electromagnetic flux together drive and support the rotor.

Further advantageous measures and embodiments of the invention result from the dependent claims.

BRIEF DESCRIPTION OF THE DRAWINGS

The invention will be explained in more detail hereinafter with reference to the drawings.

FIG. 3 is a section through the temple motor of FIG. 2 in an axial direction;

FIG. 4 is a perspective representation of a first embodiment of an electromagnetic rotary drive in accordance with the invention;

FIG. 19 is a section through the sixth embodiment of FIG. 18 in an axial direction;

FIGS. 20 to 23 are different variants for the embodiment of the coil cores, each in a perspective representation;

DETAILED DESCRIPTION OF THE EMBODIMENTS

Figure 1:
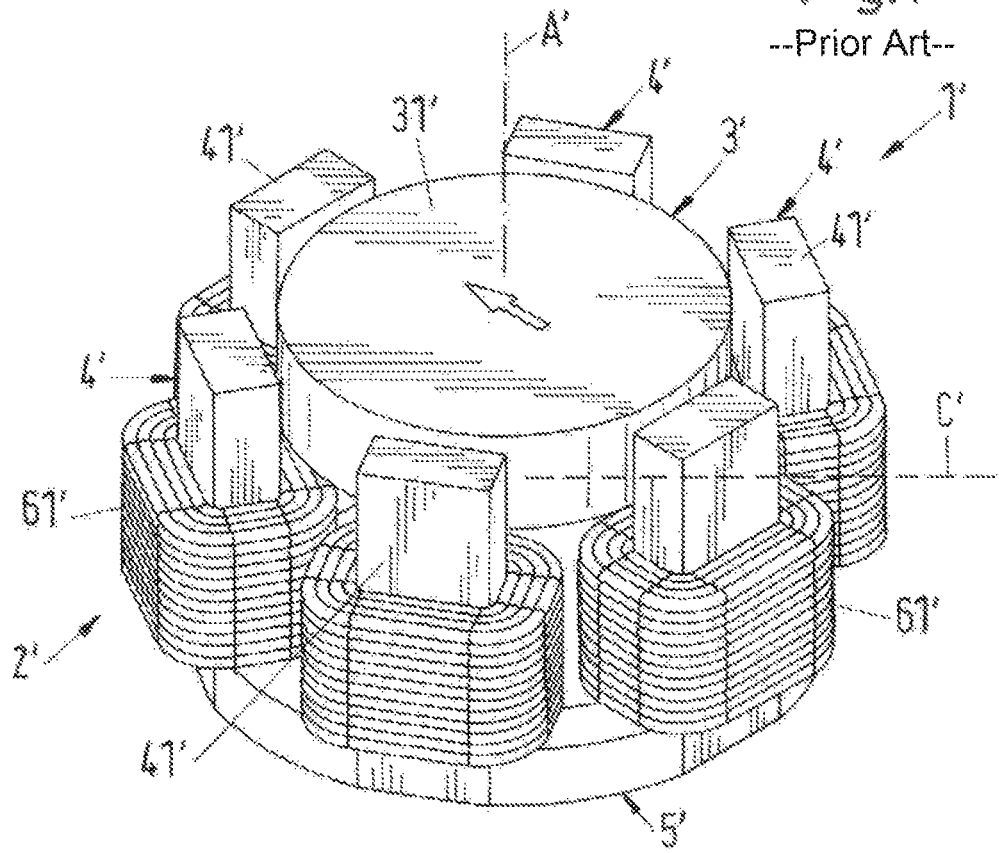
FIG. 1 is a perspective representation of a temple motor in accordance with the prior art.
Figure 2:
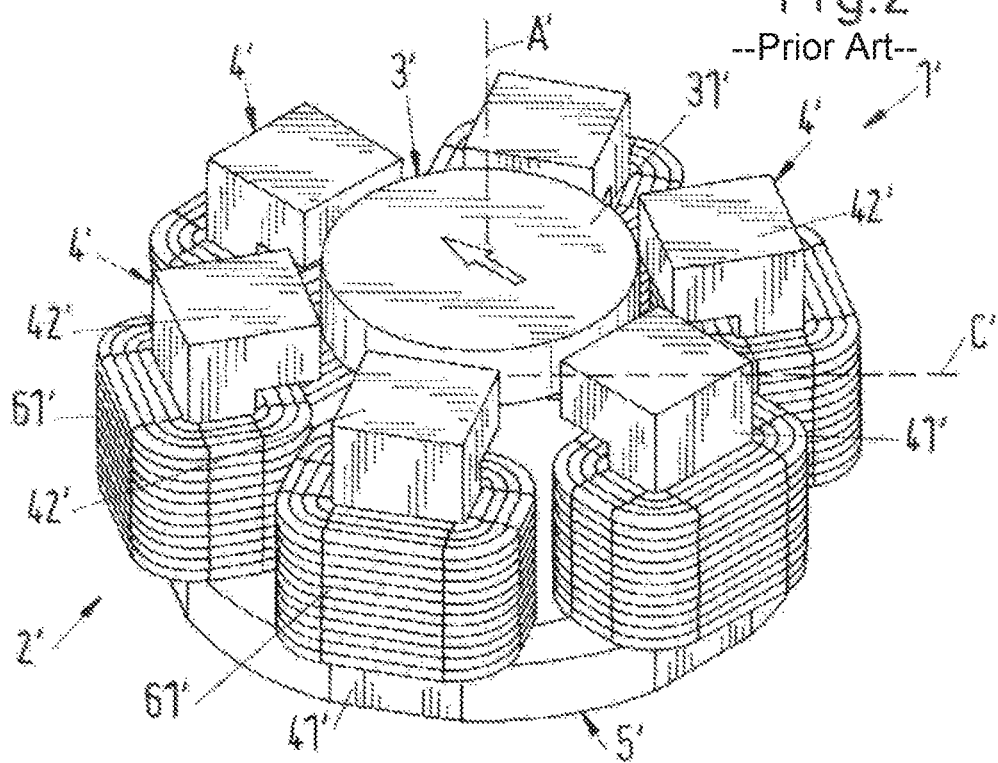
FIG. 2 is a perspective representation of another temple motor in accordance with the prior art.

As already mentioned, two temple motors that are known from the prior art are shown in FIGS. 1 to 3.

FIG. 4 shows a perspective representation of a first embodiment of an electromagnetic rotary drive in accordance with the invention that is designated as a whole by the reference numeral 1. The rotary drive 1 is configured as a temple motor and comprises a stator 2 and a rotor 3 that is contactlessly magnetically supported in the stator 2 and that is configured free of coils and free of permanent magnets. The rotor 3 is configured as a reluctance rotor and comprises a magnetically effective core 31 that is formed in cross shape with four pronounced rotor teeth 32 in the first embodiment. In the operating state, the rotor 3 can be contactlessly magnetically driven about a desired axis of rotation by the stator 2. That axis is called the desired axis of rotation about which the rotor 3 rotates in the operating state when the rotor 3 is in a centered and non-tilted position with respect to the stator 2. This desired axis of rotation defines an axial direction A. The desired axis of rotation A fixing the axial direction A typically coincides with the central axis of the stator 2.

Since it is sufficient for the understanding of the invention, only the respective magnetically effective core 31 of the rotor 3 is shown in the embodiments and variants of the electromagnetic rotary drive 1 described in the following. It is understood that the rotor 3 can naturally also comprise still further components such as jackets or encapsulations that are preferably manufactured from a plastic or such as vanes for mixing, stirring or pumping a fluid or such as other components.

A direction that stands perpendicular on the axial direction A is called a radial direction in the following. Furthermore, the magnetic center plane of the magnetically effective core 31 of the rotor 3 is called the magnetic rotor plane C. It is that plane perpendicular to the axial direction A in which the rotor 3 or the magnetically effective core 31 of the rotor 3 is supported in the operating state when the rotor 3 is not tilted. As a rule, the magnetic rotor plane C is the geometrical center plane of the magnetically effective core 31 of the rotor 3 that is disposed perpendicular to the axial direction A. That plane in which the rotor 3 is supported in the operating state is also called the radial plane. The radial plane defines the x-y plane of a Cartesian coordinate system whose z axis extends in the axial direction A. If the rotor 3 is therefore not tilted, the radial plane coincides with the magnetic rotor plane C.

What is characteristic in a design as a temple motor is that the stator 2 comprises a plurality of separate coil cores 4 of which each comprises a bar-shaped longitudinal limb 41 that extends from a first end 43 in the axial direction A up to a second end 44, with all the first ends 43—they are the lower ends in accordance with the representation in FIG. 4—being connected to one another by a reflux 5. In this respect, the reflux 5 comprises a plurality of segments 51 of which each connects the respective first end 43 of a coil core 4 to the first end 43 of the adjacent coil core 4. As FIG. 4 also shows, the individual coil cores 4 are preferably arranged such that they surround the rotor 3 in circular form in an embodiment as an internal rotor and are arranged equidistant on this circle. In operation, the rotor 3 is contactlessly magnetically supported between the second ends 44 of the coil cores 4.

It is the longitudinal limbs 41 of the coil cores 4 that are aligned in parallel with one another, that all extend in parallel with the axial direction A and that surround the rotor 3 (or, in an embodiment as an external rotor, are surrounded by the rotor 3) that have given the temple motor its name because these parallel longitudinal limbs 41 are reminiscent of the columns of a temple.

The stator 2 furthermore comprises a plurality of windings 6 for generating an electromagnetic rotational field. The windings 6 are here configured as individual coils 61 of which each surrounds one of the longitudinal limbs 41. This means that the axes of the coils 61 each extend in parallel with the axial direction A. In the first embodiment shown in FIG. 4, each longitudinal limb 41 supports exactly one coil 61.

It is therefore a further feature of the temple motor 1 that the coils 61 of the stator 2 are arranged outside the magnetic rotor plane C, beneath the magnetic rotor plane C in accordance with the representation. The coils 61 are preferably arranged completely beneath the magnetically effective core 31. The coils 61 are therefore not arranged in the plane in which the rotor 3 is driven and supported in the operating state. Unlike other electromagnetic rotary drives in which the coils of the stator are arranged such that the coil axes each lie in the magnetic rotor plane, that is in the plane in which the rotor is driven and supported, in the temple motor 1, the coils 61 of the stator 2 are arranged such that the axes of the coils 61 stand perpendicular on the magnetic rotor plane C.

Within the framework of the present invention, an embodiment as a temple motor or a temple motor 1 is to be understood as such an electromagnetic rotary drive 1 that has a plurality of coil cores 4 of which each comprises a longitudinal limb 41 that respectively extends in parallel with the axial direction A, wherein the first ends 43 of all coil cores 4 are connected to one another via the reflux 5, and wherein the windings 6, 61 of the stator 2 are each arranged around the longitudinal limbs 41 such that the respective coil axes of the individual coils 61 are aligned in parallel with the axial direction A. In a preferred embodiment, the electromagnetic rotary drive configured as a temple motor 1 is configured in accordance with the principle of a bearingless motor. The temple motor 1 is in this case therefore a specific embodiment of a bearingless motor.

Even if the embodiment of the temple motor 1 in accordance with the principle of a bearingless motor is preferred, the invention is not restricted to this embodiment. Embodiments are by all means also possible in which the bearing function of the rotor is implemented by other measures, for example by one or more separate magnetic bearing units or by other bearings, in particular mechanical bearings.

In a bearingless motor, the rotor 3 is contactlessly magnetically drivable and is contactlessly magnetically supportable with respect to the stator 2. For this purpose, the stator 2 is designed as a bearing and drive stator by which the rotor 3 can be driven contactlessly magnetically about the desired axis of rotation in the operating state—that is it can be set into rotation—and can be supported contactlessly magnetically with respect to the stator 2.

The bearingless motor has in the meantime become sufficiently well-known to the skilled person that a detailed description of its function is no longer necessary. The term bearingless motor means that the rotor 3 is supported completely magnetically, with no separate magnetic bearings being provided. The stator 2 is configured for this purpose as a bearing and drive stator; it is therefore both the stator of the electric drive and the stator of the magnetic support. The stator 2 in this respect comprises the windings 6 by which a magnetic rotational field can be generated which, on the one hand, exerts a torque on the rotor 3 which effects its rotation and which, on the other hand, exerts a shear force which can be set as desired on the rotor 3 so that its radial position—that is its position in the radial plane—can be actively controlled or regulated. At least three degrees of freedom of the rotor 3 can thus be actively regulated. The rotor 3 is at least passively magnetically stabilized, that is cannot be controlled, by reluctance forces with respect to its axial deflection in the axial direction A. The rotor 3 can also likewise be stabilized—depending on the embodiment—passively magnetically with respect to the remaining two degrees of freedom, namely tilts with respect to the radial plane perpendicular to the desired axis of rotation.

An electromagnetic drive and bearing apparatus is known from the prior art, for example from US-A-2009/121571, in which the stator of the drive and the stator of the magnetic bearing are joined together to form a construction unit. The stator here comprises a bearing unit that consists of an upper and a lower bearing plane and comprises a drive unit that is arranged between these bearing planes. This apparatus therefore also shows a bearing unit that can be separated from the drive unit and that only serves for the magnetic support. Such apparatus are, however, not to be understood as bearingless motors in the sense of the present application because actually separate bearing units are present here that implement the support of the rotor separately from the drive function. In a bearingless motor in the sense of the present invention, it is not possible to divide the stator into a bearing unit and into a drive unit. It is actually this property that gives the bearingless motor its name.

With a bearingless motor, unlike with classical magnetic bearings, the magnetic support and the drive of the motor is implemented via electromagnetic rotational fields whose sum, on the one hand, generates a drive torque on the rotor 3 as well as a transverse force that can be set as desired and with which the radial position of the rotor 3 can be regulated. These rotational fields can be generated either separately—that is using different coils—or the rotational fields can be generated by superposition by calculation of the required currents and then with the aid of a single coil system.

The rotor 3 of the rotary drive 1 in accordance with the invention is configured as coil-free, i.e. no windings are provided on the rotor 3. The rotor 3 comprises a magnetically effective core 31 which can be surrounded by a plastic jacket in dependence on the configuration. Examples for the embodiment of the rotor will be explained further below.

In the rotary drive 1 in accordance with the invention, the rotor 3 or the magnetically effective core 31 of the rotor 3 does not have any permanent magnets, it is therefore free of permanent magnets. This measure allows a particularly inexpensive embodiment of the rotor 3—for example also as a single-use part—since in particular no rare earths such as neodymium or samarium or compounds or alloys thereof are necessary for the manufacture of the rotor 3 which are frequently used for the manufacture of permanent magnets. The dispensing with of these permanent magnets in the rotor also signifies a large advantage under environmental aspects.

Those ferromagnetic or ferrimagnetic materials which are hard magnetic, that is which have a high coercive field strength, are typically called permanent magnets. The coercive field strength is that magnetic field strength which is required to demagnetize a material. Within this application, a permanent magnet is understood as a material which has a coercive field strength, more precisely a coercive field strength of the magnetic polarization, which amounts to more than 10,000 A/m.

If the rotor 3 is therefore free of permanent magnets, this means that the magnetically effective core 31 of the rotor 3 only comprises materials whose coercive field strength amounts to at most 10,000 A/m.

The designation that the rotor 3 is "free of permanent magnets" should be understood within the framework of this application that the rotor 3 does not comprise any permanent magnets which make a substantial contribution to the drive field for driving the rotation of the rotor 3. It is naturally possible that other magnets or permanent magnets are disposed at the rotor 3 which, for example, only serve for the detection of the angular position of the rotor or which otherwise satisfy a purpose which has nothing to do with the generation of the drive flux for the rotor. The designation "free of permanent magnets" therefore only relates to the drive of the rotor 3.

The designation "free of permanent magnets" with respect to the rotor is therefore to be understood within the framework of this application such that the rotor 3 is free of permanent magnets that make a contribution to the drive of the rotor or such that the rotor 3 is free of permanent magnets that contribute to the drive flux for the drive of the rotor 3.

The magnetically effective core 31 of the rotor is preferably produced from a soft magnetic material, for example from iron, nickel iron or silicon iron. In this respect, the magnetically effective core 31 can e.g. be manufactured by casting, stamping, pressing of soft magnetic powder with subsequent sintering, forging, shaping or assembling of parts such as metal sheets.

In the embodiment shown in FIG. 4 with the disk-shaped, or alternatively ring-shaped, magnetically effective core 31 of the rotor 3, the rotor 3 is actively magnetically, i.e. controllably, supported with respect to three degrees of freedom. They are the two degrees of freedom of the radial position of the rotor 3 in the radial plane and the degree of freedom of rotation. The rotor is purely passively magnetically stabilized, that is not controllably stabilized, via reluctance forces with respect to the other three degrees of freedom. They are the two degrees of freedom of the tilts of the rotor 3 with respect to the radial plane and the axial position of the rotor 3, that is its position with respect to the axial direction A. In the first embodiment of the rotary drive 1 in accordance with the invention shown in FIG. 4, it is a configuration as an internal rotor, that is the rotor 3 is arranged within the stator 2. In this first embodiment, the stator 2 comprises a total of six coil cores 4 of which each comprises a bar-shaped longitudinal limb 41 that extends in parallel with the axial direction. The six coil cores 4 are arranged in the form of a circle around the rotor 3, with the coil cores 4 being distributed equidistantly over the periphery of this circle. The first ends 43 of the bar shape longitudinal limbs 41 that are at the bottom in accordance with the representation are connected to one another by the reflux 5, wherein the reflux 5 comprises a plurality of segments 51 of which each respectively connects two adjacent first ends 43 to one another. The longitudinal limbs 41 have a rectangular cross-section perpendicular to the axial direction A. The stator 2 furthermore comprises a plurality of windings 6 for generating electromagnetic rotational fields by which the rotor 3 can be contactlessly magnetically driven and can be contactlessly magnetically supported with respect to the stator 2. In the first embodiment, a total of six individual coils 61 are provided as windings 6, wherein a respective coil 61 is provided at each of the longitudinal limbs 41. Each coil 61 is arranged around the respective longitudinal limb 41 such that the coil axis is respectively disposed in parallel with the axial direction A and thus perpendicular to the magnetic rotor plane C.

The reflux 5 or its segments 51 and the longitudinal limbs 41 of the coil cores 4 are each produced from a soft magnetic material because they serve as flux conducting elements for conducting the magnetic flux. Suitable soft magnetic materials are, for example, ferromagnetic or ferrimagnetic materials, that is in particular iron, nickel-iron or silicon iron. In this respect, an embodiment as a metal sheet stator packet is preferred in which the individual longitudinal limbs 41 and the segments 51 are configured in bundled laminate form, that is they consist of a plurality of thin elements that are stacked. Specific embodiments of the longitudinal limbs will be explained further below in connection with FIGS. 20 to 23.

The rotor 3 is configured as a reluctance rotor and comprises the magnetically effective core 31, that is here configured as a disk-shaped cross having four pronounced rotor teeth 32 and is supported in the operating state between the second ends 44—that is the upper ends in accordance with the representation—of the longitudinal limbs 41 of the coil cores 4.

In accordance with the invention, the coil cores 4 comprise a plurality of permanent magnets 45 for generating a permanent magnetic pre-magnetization that contribute to generating the magnetic drive flux by which the rotation of the rotor 3 is driven about the desired axis of rotation.

In the first embodiment, a total of six permanent magnets 45 are provided for this purpose, wherein a respective permanent magnet 45 is disposed at the second end of each longitudinal limb 41, said permanent magnet being respectively arranged disposed radially inwardly at the longitudinal limb 41 of the coil core 4, that is at the side of the longitudinal limb 41 facing the rotor 3. Overall, each coil core 4 thus has an L-shaped cross-sectional surface in a section in the axial direction A, wherein the respective longitudinal limbs 41 form the long limb of the L and the permanent magnets 45 form the short limb of the L that is oriented toward the rotor 3. The permanent magnets 45 are here each configured in substantially parallelepiped form, with their radially outwardly disposed boundary surface respectively being congruent with the second ends of the longitudinal limbs 41.

The permanent magnets 45 are each magnetized in the radial direction as the arrows without reference numerals in FIG. 4 indicate. In this respect, permanent magnets 45 adjacent in the peripheral direction are each polarized in opposite directions, i.e. a permanent magnet 45 whose magnetization is inwardly directed in the radial direction has a respective two permanent magnets 45 as neighbors in the peripheral direction whose magnetization is respectively outwardly directed in the radial direction.

In the operating state, electromagnetic rotational fields are generated by the coils 61 in the manner known from a bearingless motor and a tangential force on the rotor 3 can be generated by them, on the one hand, that effects a torque that drives the rotation of the rotor 3 and with which, on the other hand, a transverse force can be exerted on the rotor 3 in the radial direction that can be set as desired and by which the position of the rotor 3 can be actively magnetically regulated in the radial plane. The permanent magnets 45 in this respect generate a permanent magnetic pre-magnetization flux, wherein the permanent magnetic flux and the electromagnetic flux together drive the rotor 3.

The great advantage of the permanent magnetic pre-magnetization flux is—as already explained above—that the total magnetic flux to drive and support the rotor 3 does not have to be generated in an electromagnetic manner.

In the temple motor 1, the longitudinal limbs 41 in this respect serve as flux guiding elements that are oriented in the axial direction and that guide the magnetic flux, and in particular also the electromagnetic flux generated by the coils 61, in the magnetic rotor plane C in which the rotor 3 is driven and supported.

The power electronics required for the control of the coils 61 and the corresponding control and regulation devices are sufficiently known to the skilled person and do not therefore need to be explained in more detail here. The embodiment or the arrangement of the positional sensor system by which the radial position and the angular position of the rotor 3 are detected will be looked at further below in connection with FIGS. 42 to 47.

It is understood that the first embodiment can also be configured as an external rotor in a variant in which the then preferably ring-shaped magnetic core 31 of the rotor 3 surrounds the second ends 44 of the longitudinal limbs 41. The permanent magnets 45 are then naturally arranged in accordingly the same manner at the radially outwardly disposed surfaces of the second ends 44 of the longitudinal limbs 41 so that they in turn face the rotor 3.

Figure 5:
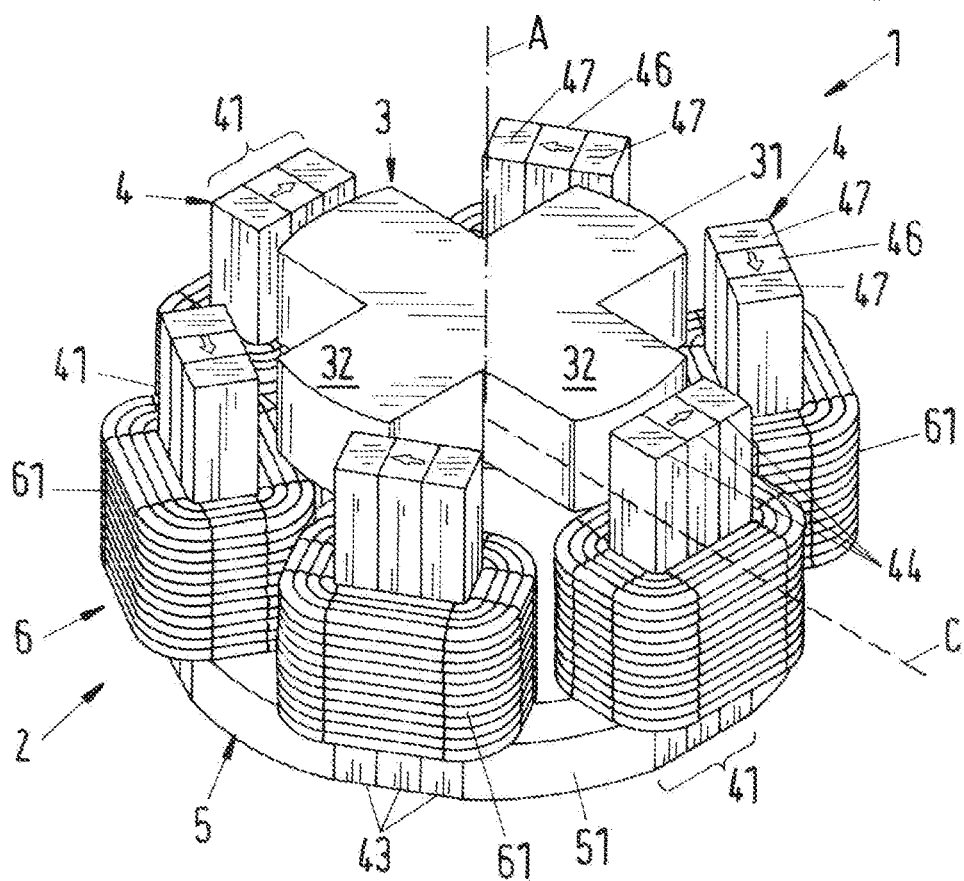
FIG. 5 is a perspective representation of a second embodiment of an electromagnetic rotary drive in accordance with the invention.
Figure 6:
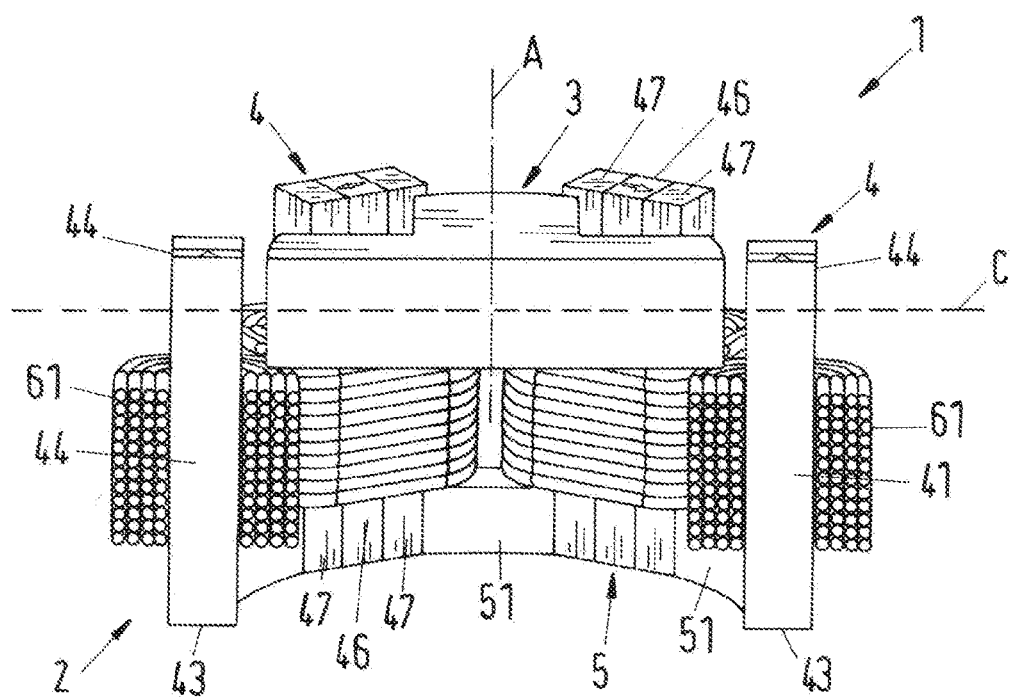
FIG. 6 is a section through the second embodiment of FIG. 5 in an axial direction.

FIG. 5 shows a second embodiment of a rotary drive 1 in accordance with the invention in a perspective representation. FIG. 6 additionally shows a section through this second embodiment in the axial direction A. In the following, only the differences from the above-described first embodiment will be looked at. The reference numerals in particular have the same meaning as has already been explained in connection with the first embodiment. It is understood that all the above explanations also apply in the same manner or in accordingly the same manner to the second embodiment.

The second embodiment mainly differs from the first embodiment by the design and the arrangement of the permanent magnets 45 in the stator 2. In the second embodiment, each coil core 4 as a permanent magnet comprises a permanent magnetic portion 46 that respectively extends from the first end 43 of the longitudinal limb 41 of the respective coil core 4 in the axial direction A up to the second end 44 of the longitudinal limb 41. In addition, each longitudinal limb 41 comprises two permanent magnet-free portions 47 that each extend from the first end 43 up to the second end 44 of the respective longitudinal limb 41. The permanent magnetic portion 46 is in this process respectively arranged between the two permanent magnet-free portions 47 of the longitudinal limb 41. Viewed in the peripheral direction of the stator 2, each longitudinal limb 41 of each coil core 4 therefore comprises the bar-shaped permanent magnetic portion 46 that is arranged between the two likewise bar-shaped permanent magnet-free portions 47 In this respect, the length of the permanent magnetic portion 46 in the axial direction A is the same size as the length of the two permanent magnet-free portions 47 adjacent to it in the axial direction A. The permanent magnetic portion 46 also has the same extent with respect to the radial direction as the two permanent magnet-free portions 47 adjacent to it such that the permanent magnet-free portions 47 are completely separated from one another by the permanent magnetic portion 46 disposed therebetween. The cross-sectional surfaces of the two permanent magnet-free portions 47 and of the permanent magnetic portion 46 are identical in an axial section perpendicular to the peripheral direction of the stator 2 such that, in a section perpendicular to the axial direction A and in parallel with the radial plane, or in parallel with the magnetic center plane C of the rotor 3, every coil core 4 has a rectangular cross-sectional surface that is formed by the two permanent magnet-free portions 47 and the permanent magnetic portion 46 arranged therebetween. Each coil core 4 thus comprises three bar-shaped components arranged in parallel with one another and each extending in the axial direction A, namely the two permanent magnet-free portions 47 and the permanent magnetic portion 46 arranged between them.

This arrangement has the advantage, as will be described further below, that in particular the electromagnetically generated flux can only be guided within the stator 2 through the permanent magnet-free portions 47 serving as flux conducting elements and the reflux 5, that is only through soft magnetic material. It can thus be avoided that the electromagnetically generated flux in the stator 2 has to be guided through the permanent magnetic portions 46 that represent a very high resistance for the electromagnetically generated flux.

As the arrows without reference numerals in the permanent magnetic portions 46 show in FIGS. 5 and 6, the permanent magnetic portions 46 are each polarized or magnetized in the peripheral direction of the stator 2, i.e. every permanent magnetic portion 46 has a magnetization that is oriented perpendicular to the radial direction and perpendicular to the axial direction A. The permanent magnetic portions 46 of adjacent coil cores 4 are in this respect each magnetized in the reverse direction, that is each permanent magnetic port 46 of a coil core 4 is surrounded by two permanent magnetic portions 46 of adjacent coil cores 4 viewed in the peripheral direction that are each magnetized in the opposite direction to itself.

A total of six coil cores 4 are also provided in the second embodiment and surround the rotor 3 in a circular form and equidistantly. The number of six coil cores 4 is to be understood as exemplary in this respect. A different number of coil cores 4 can naturally also be provided, for example eight or twelve or four coil cores 4, wherein an even number of coil cores 4 is preferred for technical regulation reasons. A number of six or eight or twelve coil cores 4 has proven advantageous for many applications.

Figure 7:
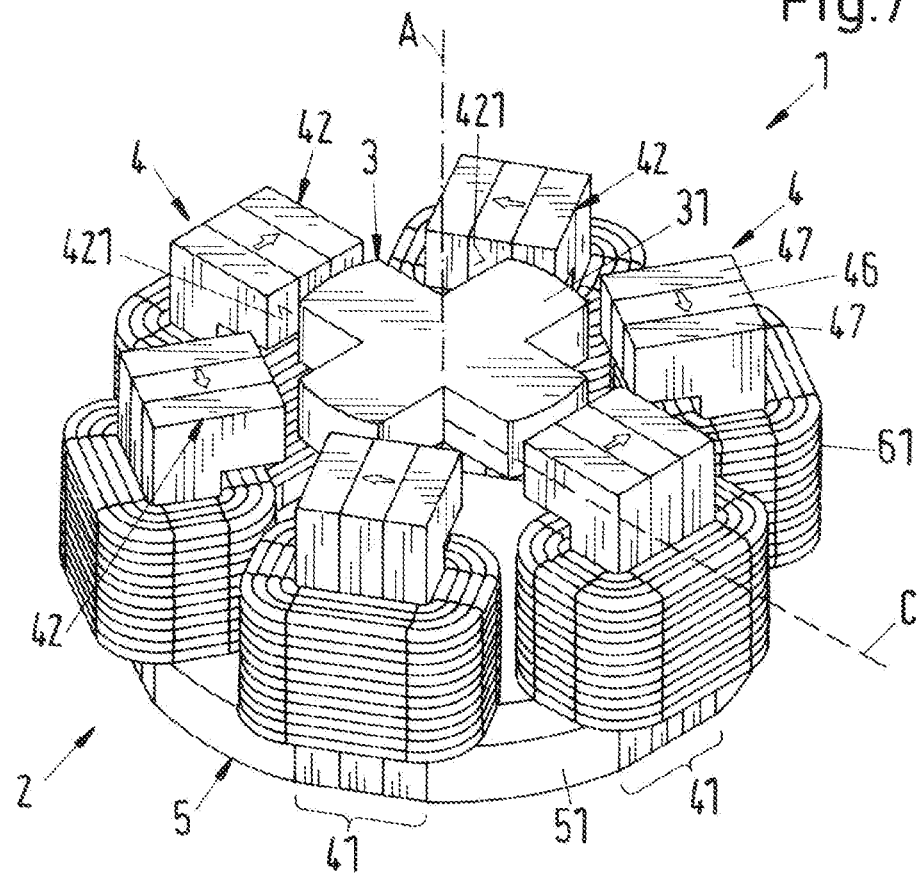
FIG. 7 is a perspective representation of a third embodiment of an electromagnetic rotary drive in accordance with the invention.
Figure 8:
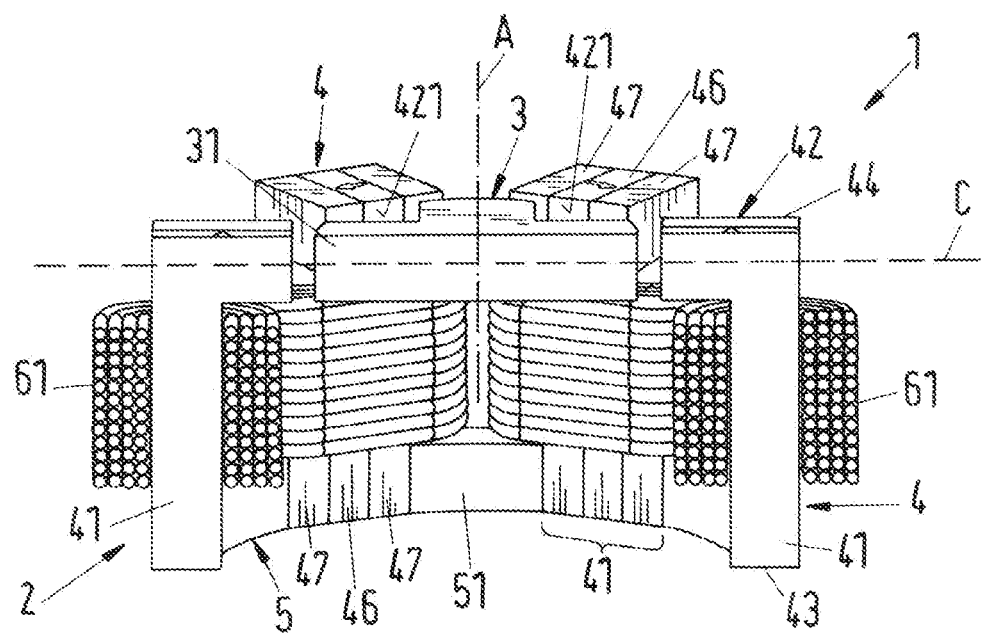
FIG. 8 is a section through the third embodiment of FIG. 7 in an axial direction.

FIG. 7 shows a preferred third embodiment of the rotary drive 1 in accordance with the invention in a perspective representation. For better understanding, FIG. 8 shows a section through this third embodiment in the axial direction. In the following, only the differences from the above-described embodiments will be looked at. The reference numerals in particular have the same meaning as has already been explained in connection with the embodiments described above. It is understood that all the above explanations also apply in the same manner or in accordingly the same manner to the third embodiment.

In the third embodiment, each coil core 4 comprises a transverse limb 42 that is arranged at the second end 44 of the respective longitudinal limb 41 and that extends in the radial direction, that is perpendicular to the axial direction A and thus perpendicular to the respective longitudinal limb 41. In the embodiment of the electromagnetic rotary drive 1 shown in FIGS. 7 and 8 as an internal rotor, the transverse limbs 42 extend inwardly, that is toward the rotor 3, in the radial direction. It is understood that in an embodiment of the rotary drive 1 as an external rotor (see e.g. FIG. 18), the transverse limbs 42 each extend outwardly, that is again toward the rotor 3, in the radial direction.

Each coil core 4 thus has an L-shaped embodiment, wherein the longitudinal limbs 41 form the long limb of the L that extends in the axial direction A and the transverse limbs 42 that extend perpendicular to the longitudinal limbs 41 toward the rotor 3 in the radial direction form the short limb of the L.

As already described in the second embodiment, each coil core 4 also comprises the two permanent magnet-free portions 47 that include the permanent magnetic portion 46 between them in the third embodiment. In this respect, both each of the permanent magnet-free portions 47 and each of the permanent magnetic portions 46 have an L-shaped configuration, wherein the two boundary surfaces of the two permanent magnet-free portions 47 that are adjacent to the permanent magnetic portion 46 are each configured as congruent with the boundary surfaces of the permanent magnetic portion 46 contacting them. The two permanent magnet-free portions 47 of each coil core 4 are thus here also completely separated from one another by the respective permanent magnetic portion 46 disposed between them.

This means that the permanent magnet portions 46 and the two permanent magnet-free portions 47 of each coil core each also extend through the transverse limb 42 and the permanent magnetic portion 46 is also arranged between the two permanent magnet-free portions 47 in the transverse limb 42.

Each transverse limb 42 thus has a radially inwardly disposed (or radially outwardly disposed in an embodiment as an external rotor) end face 421 that faces the rotor 3. The center line of this end face 421 that is in parallel with the radial plane is in this respect disposed in the magnetic rotor plane C, i.e. in that plane in which the rotor 3 is supported in the operating state.

As the arrows without reference numerals in the permanent magnetic portions 46 show in FIGS. 7 and 8, the permanent magnetic portions 46 are each also polarized or magnetized in the peripheral direction of the stator 2, i.e. every permanent magnetic portion 46 has a magnetization that is oriented perpendicular to the radial direction and perpendicular to the axial direction A in the third embodiment. The permanent magnetic portions 46 of adjacent coil cores 4 are in this respect each magnetized in the reverse direction, that is each permanent magnetic port 46 of a coil core 4 is surrounded by two permanent magnetic portions 46 of adjacent coil cores 4 viewed in the peripheral direction that are each magnetized in the opposite direction to itself.

The design in accordance with the third embodiment makes it possible in a particular easy manner to guide the permanent magnetic flux in the stator 2 separately from the electromagnetic flux in the sense that the electromagnetic flux does not have to be guided by the permanent magnetic portions 46 and that at the same time a superposition of these two magnetic fluxes is possible in the gap between the rotor 3 and the stator 2. This will be explained in the following with respect to FIG. 9 that shows a plan view of the third embodiment from the axial direction.

Figure 9:
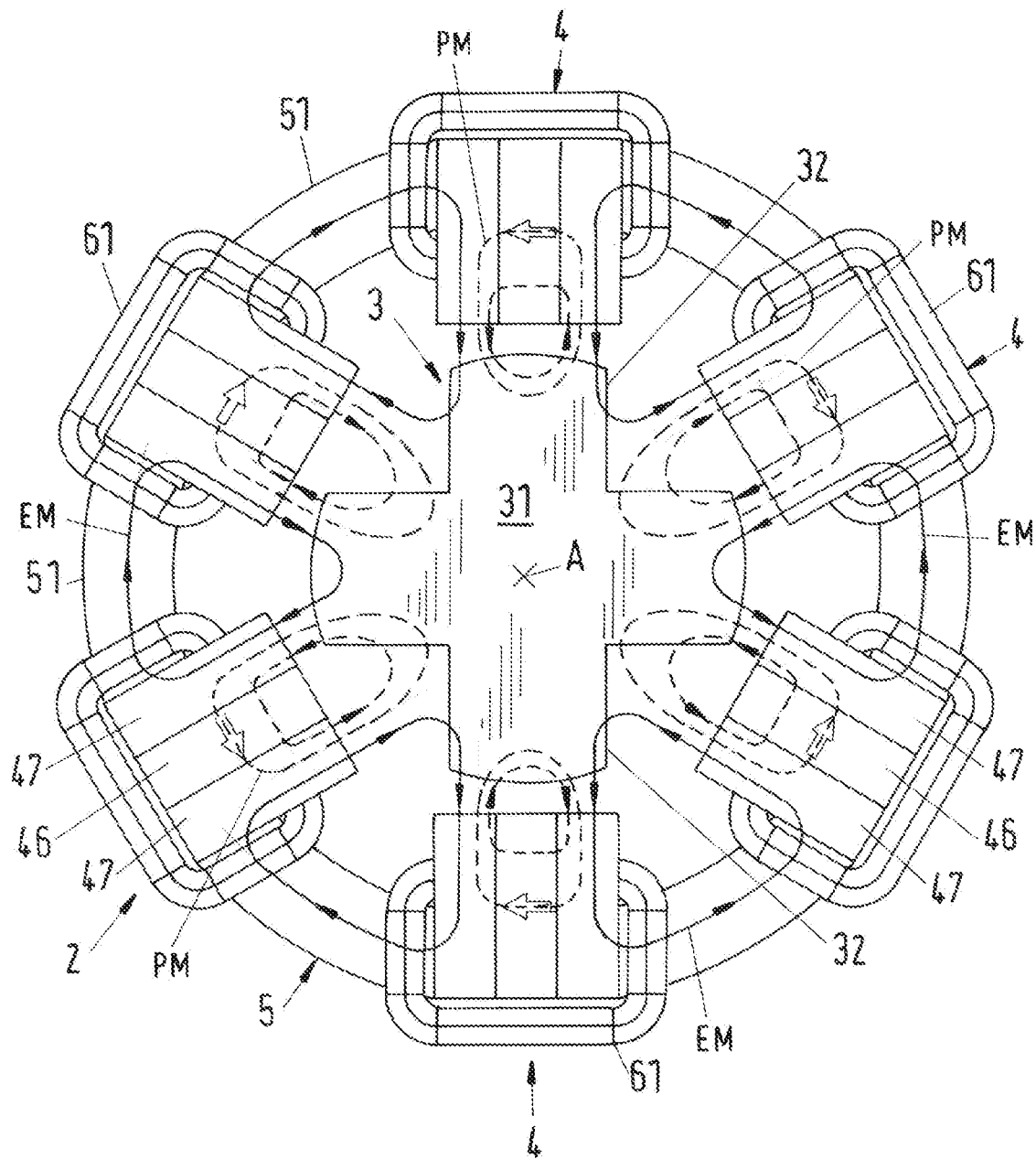
FIG. 9 is a plan view of the third embodiment of FIG. 7 with the extent of magnetic flux lines.

In FIG. 9, the extent of the permanent magnetic flux generated by the permanent magnetic portions 46 is shown schematically by the field lines provided with the reference symbol PM and shown in dashed form. The permanent magnetic flux PM extends in each case from the permanent magnetic portion 46 into the one of the adjacent permanent magnet-free portions 47, is guided by it toward the magnetic core 31 of the rotor 3 in the radial direction, passes through the air gap between the coil core 4 and the magnetically effective core 31 of the rotor 3, is guided back by it into the air gap, then moves to the other one of the adjacent permanent magnet-free portions 47 that guides the permanent magnetic flux PM radially outwardly and then guides it back into the permanent magnetic portion 46, whereby the flux line terminates.

The electromagnetic flux generated by the windings 6 or by the coils 61 is shown schematically in FIG. 9 by the field lines provided with the reference symbol EM and shown by solid lines. The electromagnetic flux EM generated by current application by a coil 61 arranged on the longitudinal limb 41 of an individual coil core 4 is guided by the two soft magnetic permanent magnet-free portions 47 of this coil core 4 inwardly in the radial direction toward the magnetic core 31 of the rotor 3, passes through the air gap between this coil core 4 and the magnetically effective core 31 of the rotor 3, is guided back by it into the air gap, then moves to the two permanent magnet-free portions 47 of the two adjacent coil cores 4 of the individual coil core 4 that are arranged adjacent to the permanent magnet-free portions 47 of the individual coil core 4, is first guided radially outwardly by these two permanent magnet-free portions 47 and is then guided in the axial direction to the reflux 5, whereby the field line terminates.

It can be ensured in this manner that the electromagnetic flux EM in the stator 2 is only guided by soft magnetic material, namely by the permanent magnet-free portions 47 of the coil cores 4 and by the reflux 5, but not by the hard magnetic material from which the permanent magnetic portions 46 of the coil cores 4 are produced. A particularly efficient utilization of the energy of the electromagnetic flux EX results in an advantageous manner from this for the support and for the drive of the rotor 3.

Figure 10:
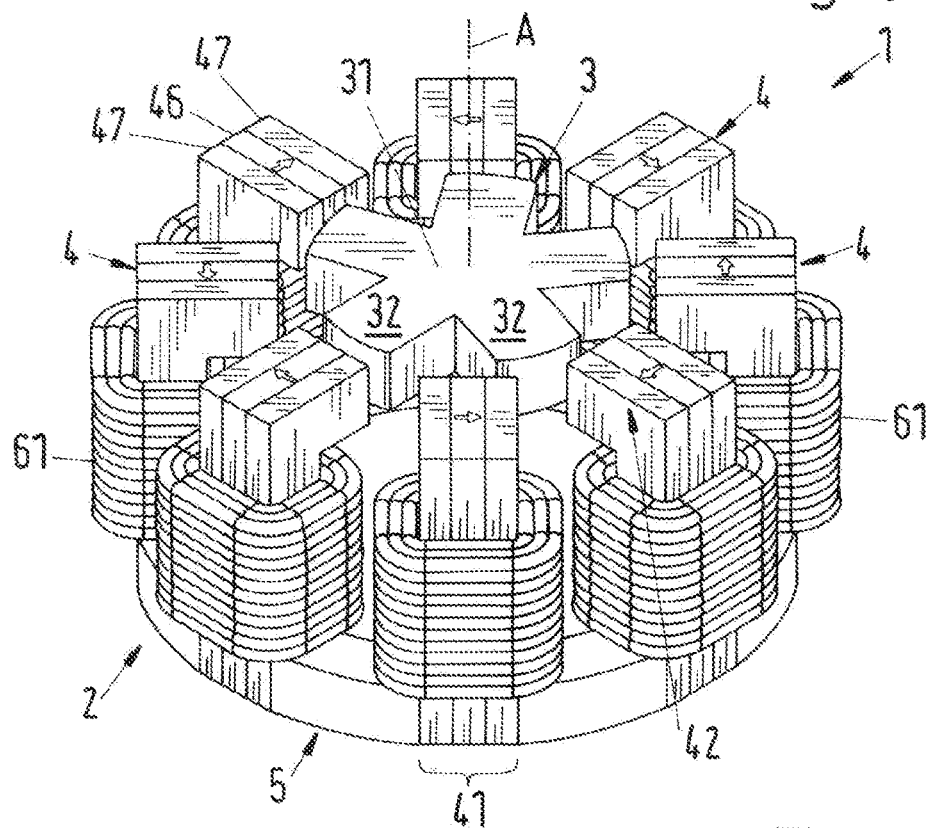
FIG. 10 is a variant of the third embodiment in a representation analog to FIG. 7.
Figure 11:
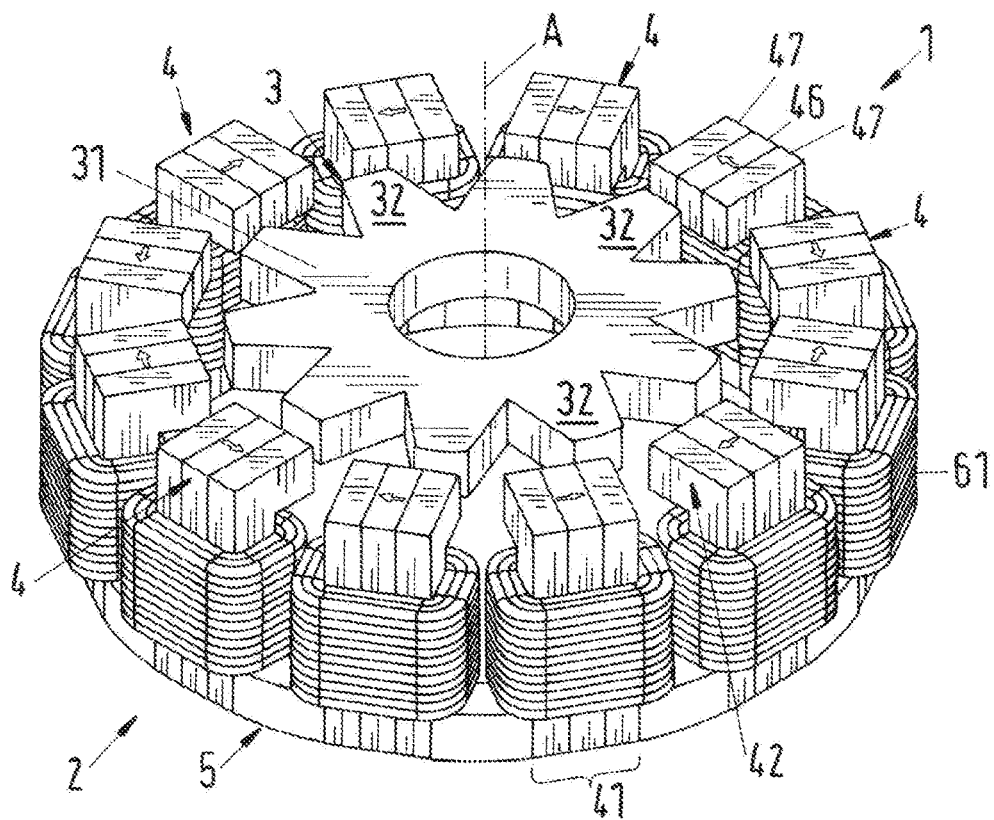
FIG. 11 is a further variant of the third embodiment in a representation analog to FIG. 7.

Two variants of the third embodiment are each shown in a perspective representation in a representation analog to FIG. 7 in FIGS. 10 and 11. In the variant shown in FIG. 10, the stator 2 has a total of eight coil cores 4 that are all configured the same and as described above. Exactly one coil 61 is again arranged on each longitudinal limb 41. The magnetically effective core 31 of the rotor 3 is of disk shape and start shape having five pronounced rotor teeth 32. In the variant shown in FIG. 11, the stator 2 has a total of twelve coil cores 4 that are all configured the same and as described above. Exactly one coil 61 is again arranged on each longitudinal limb 41. The magnetically effective core 31 of the rotor 3 is of ring shape with a central hole. It is in turn of star shape and has ten pronounced rotor teeth 32.

It is understood that the rotary drive 1 in accordance with the invention can also still be configured in a large number of different variants with respect to the number of coil cores 4 and with respect to the number of rotor teeth 32, wherein an even number of coil cores 4 is preferred for reasons of technical regulation. It is not a problem for the skilled person to select a designed number of coil cores 4 in dependence on the application and to select an embodiment of the magnetically effective core 31 of the rotor 3 adapted thereto, e.g. a respective suitable number of rotor teeth 32.

Figure 12:
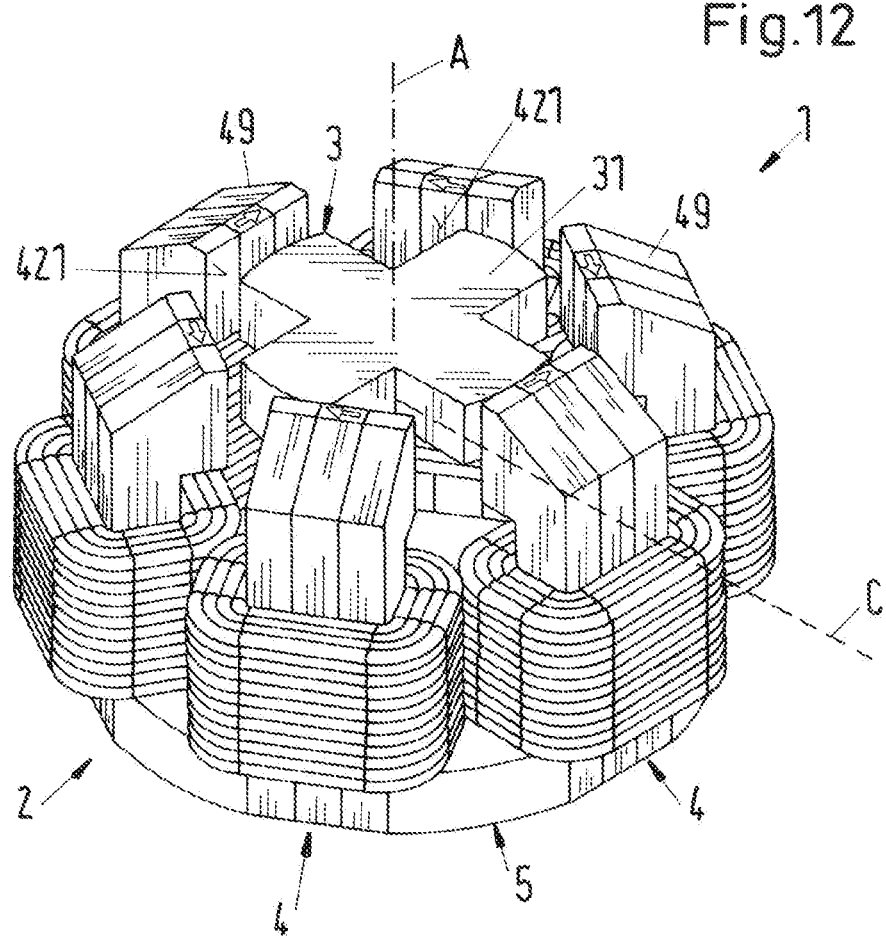
FIG. 12 is a perspective representation of a fourth embodiment of an electromagnetic rotary drive in accordance with the invention.
Figure 13:
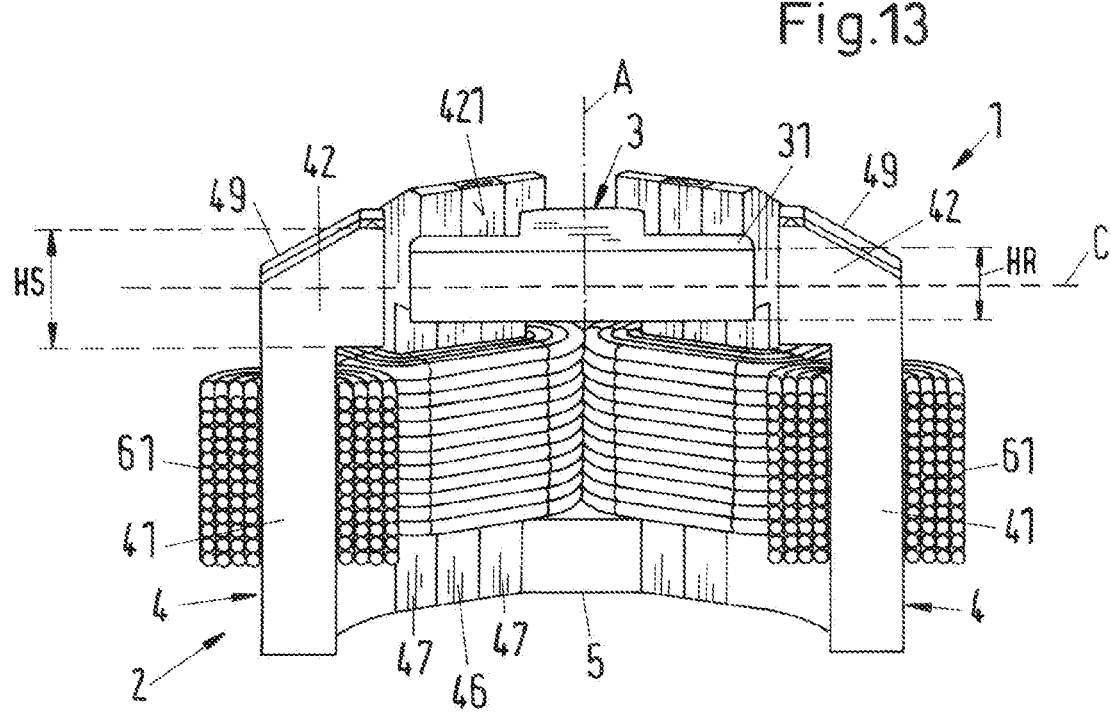
FIG. 13 is a section through the fourth embodiment of FIG. 12 in an axial direction.

FIG. 12 shows a fourth embodiment of a rotary drive 1 in accordance with the invention in a perspective representation. For better understanding, FIG. 13 shows a section through this fourth embodiment in the axial direction. In the following, only the differences from the above-described embodiments will be looked at. The reference numerals in particular have the same meaning as has already been explained in connection with the embodiments described above. It is understood that all the above explanations also apply in the same manner or in accordingly the same manner to the fourth embodiment.

In the fourth embodiment, the stator 2 has a total of six coil cores 4 that are again substantially of L shape, that is with the longitudinal limb 41 extending in the axial direction A and with the transverse limb 42 directed toward the rotor 3. In the fourth embodiment, however, the radially outwardly disposed transition from the longitudinal limb 41 to the transverse limb 42 in each coil core 4 includes a chamfer 49 such that the axial height of the transverse limb 42 increases in the radial direction viewed toward the rotor 3.

Otherwise, each coil core 4 is in turn configured with the two substantially L-shaped permanent magnet-free portions 47 and the substantially L-shaped permanent magnetic portion 46 disposed therebetween, wherein the mutually abutting boundary surfaces of the permanent magnetic portion 46 and of the two permanent magnet-free portions 47 are congruent.

In the fourth embodiment, the end face 421 of the transverse limb 42 facing the rotor 3 in each coil core 4 is designed, viewed in the axial direction, with a height HS that is larger than the axial height HR of the magnetically effective core 31 of the rotor 3 such that each of these end faces 421 projects upwardly and downwardly over the outer surface of the rotor 3 facing it with respect to the axial direction A. This can be recognized particularly well in FIG. 13.

This embodiment with HS greater than HR is in particular especially advantageous with respect to the passive magnetic stabilization of the rotor 3 against tilts and against deflections with respect to the axial direction A. Since the end faces 421 have a greater extent in the axial direction A than the magnetically effective portion 31 of the rotor 3, the rotor 3 is considerably better passively magnetically stabilized against tilts with respect to the axial direction A or against displacements in the axial direction A.

Classically in a bearingless motor, that is also in the specific embodiment as a temple motor 1, the magnetic drive and bearing function is generated by the superposition of two magnetic rotational fields that are typically called the drive field and the control field. These two rotational fields generated by the windings 6 or coils 61 of the stator 2 as a rule have a pole pair number that is different from one. In this respect, tangential forces are generated on the rotor 3 by the drive field that act in the radial plane and that effect a torque, which effects the rotation of the rotor 3 about the axial direction A. A transverse force can additionally be generated on the rotor 4 in the radial plane by the superposition of the drive field and of the control field that can be set as desired and by which the position of the rotor 3 in the radial plane can be regulated.

It is, on the one hand, possible for the generation of the drive field and control field to use two different winding systems, namely one for generating the drive field and one for generating the control field. The coils for generating the drive field are then typically called drive coils and the coils for generating the control field are called control coils. The current that is imparted into these coils is then called the drive current or control current. On the other hand, it is, however, also possible to generate the drive and support function by only one single winding system such that there is no distinction between drive coils and control coils. This can be implemented such that the respective values for the drive and control current determined by the control device are added or superposed by calculation—that is e.g. with the aid of software—and the total current resulting from this is imparted into the respective coils. In this case, it is naturally no longer possible to distinguish between control coils and drive coils. In the four embodiments described up to now, the last-named variant is implemented, that is there is no distinction between the drive coils and the control coils, but there is rather only one winding system in whose coils 61 the sum of drive current and control current determined by calculation is imparted. It is, however, naturally also possible to configure these first four embodiments and the further embodiments and all the described variants with two separate winding systems, namely in each case with separate drive coils and separate control coils. Respective variants for designing the winding system will now be explained with respect to FIGS. 14 to 16.

Figure 14:
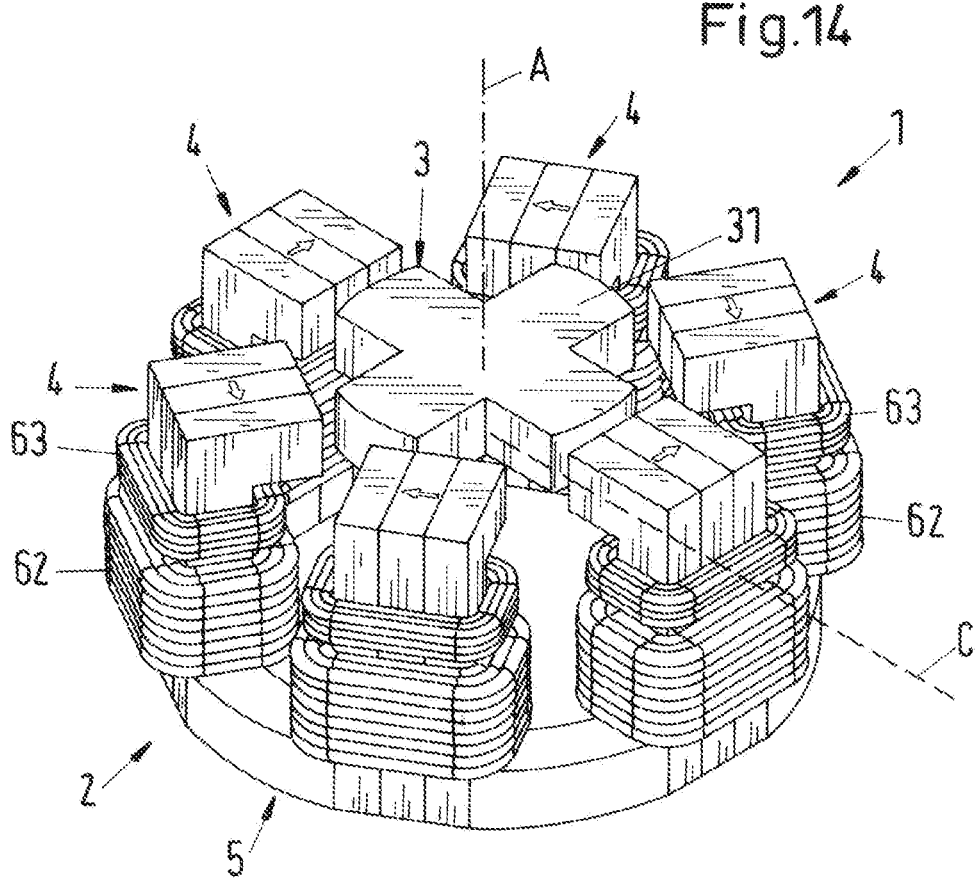
FIG. 14 is a first variant for the embodiment of the windings in a representation analog to FIG. 7.
Figure 15:
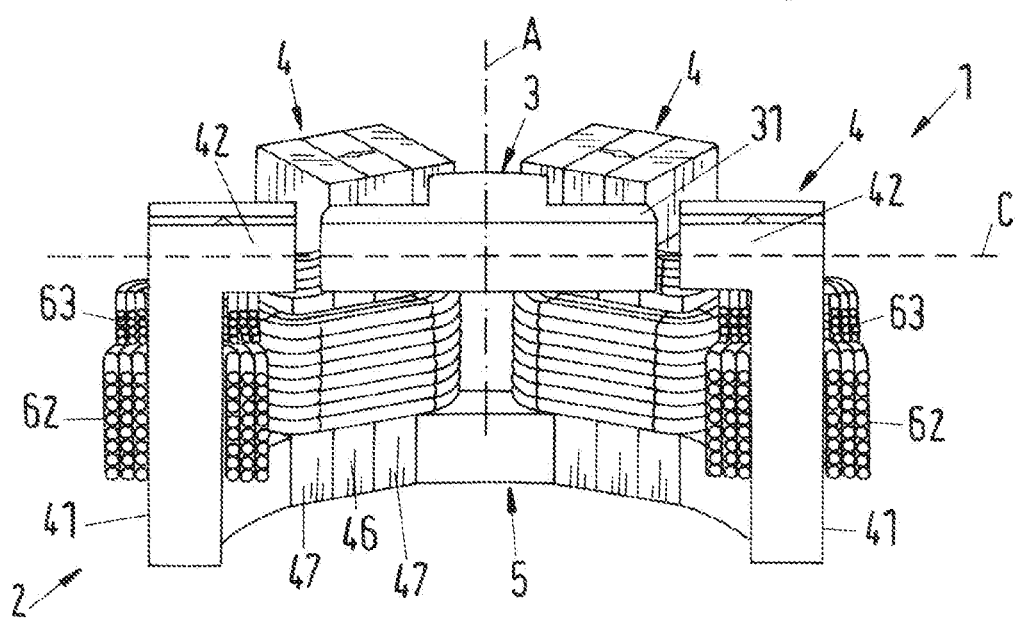
FIG. 15 is a section through the variant shown in FIG. 14 in an axial direction.

A variant is shown in a representation corresponding to FIG. 7 in FIG. 14 in which a respective drive coil 62 and a respective control coil 63 is arranged on the longitudinal limb 41 of each coil core 4. For better understanding, FIG. 15 shows a section through this variant, with the section being made in the axial direction A. The drive coil 62 and the control coil 63 on each longitudinal limb 41 are arranged coaxially and adjacent to one another with respect to the axial direction A. In accordance with the representation, the control coil 63 is respectively arranged above the drive coil 62 on the longitudinal limb 41 of the respective coil 4. It is also preferred here in this respect if both the drive coil 62 and the control coil 63 are disposed completely beneath the magnetically effective core 31 of the rotor 3 with respect to the axial direction A.

Figure 16:
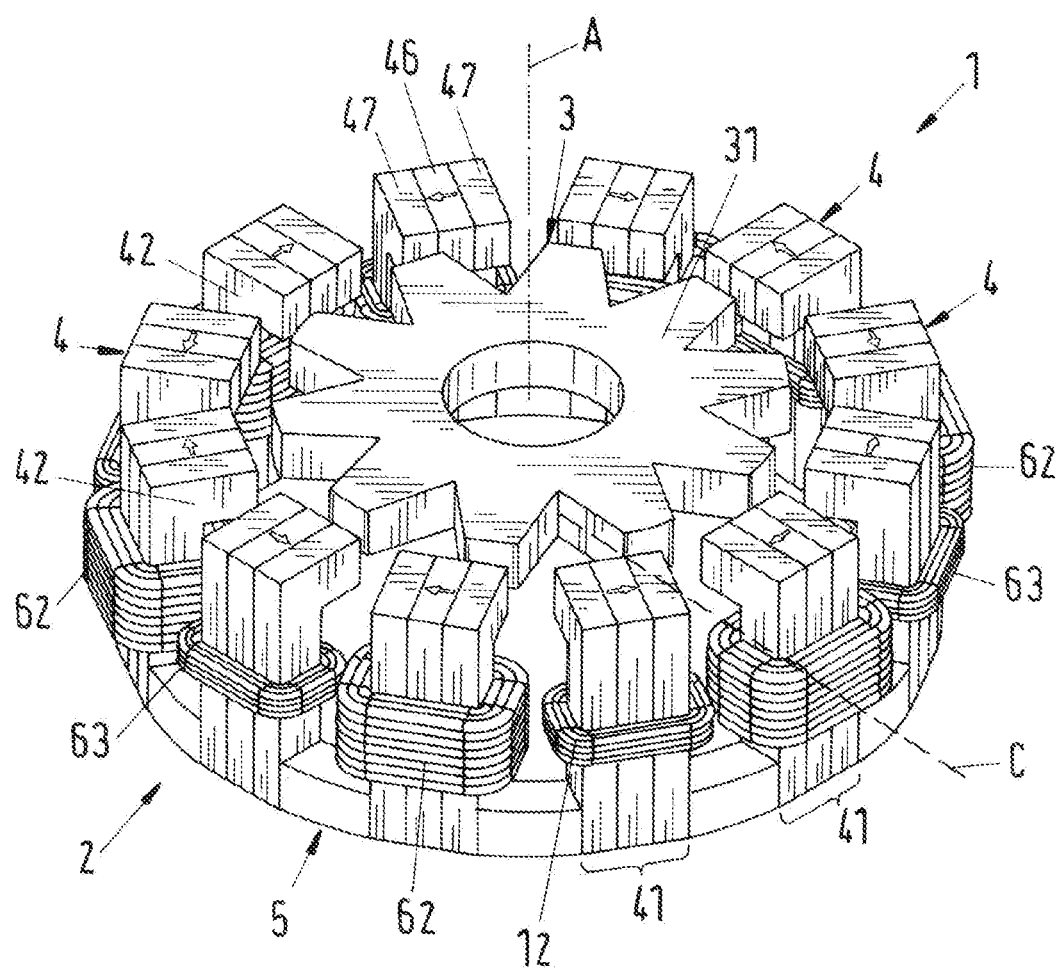
FIG. 16 is a second variant for the embodiment of the windings in a representation analog to FIG. 11.

A variant is shown in FIG. 16 in a representation corresponding to FIG. 11 in which only one respective coil is arranged on each longitudinal limb 41, that is either a drive coil 62 or a control coil 63. It is preferred in this respect if a control coil 63 and a drive coil 62 is always provided alternately on adjacent coil cores, viewed in the peripheral direction of the stator 2, i.e. each coil core 4 that only has one drive core 62 has two coil cores 4 that are directly adjacent in the peripheral direction and that each only has one control coil 63 and vice versa.

As already mentioned, these different winding concepts, that is the concept having separate drive coils 62 and control coils 63 and the concept having only one type of coil 61 can be applied to all embodiments of the rotary drive 1 in accordance with the invention.

The coils 61 or the drive coils 62 and the control coils 63 are controlled in a manner known per se to generate the electromagnetic rotational field for the operation of the temple motor 1. An adjustment device, not shown, is present for this purpose that comprises an amplifier unit and that is controlled by a control and regulation device. There are a plurality of variants for the configuration of the amplifier unit. If only one type of coil 61 is used, that is no separate drive coils and control coils, a respective separate power amplifier should preferably be provided for each of the coils 61 and the coil current or the coil voltage for this coil 61 can be regulated thereby independently of the coil currents or of the coil voltages of the other coils 61.

In the following, reference will be made with exemplary character to the case that the respective coil current is regulated as a variable. It is naturally also possible, in particular with a higher number of coils, for example twelve coils or more, to combine different coils 61 to a respective group of coils that then belong to the same electrical phase and are correspondingly controlled by the same power amplifier. The coils 61 of a group are then connected after one another in series, for example, such that the same coil current is imparted into each coil of the same group.

It is therefore possible both that each of the coils 61 is respectively designed as exactly one discrete coil that per se forms an electrical phase and that a plurality of discrete coils are combined to a group that then belong to the same electrical phase.

If, for example, six coils 61 are provided—as shown in FIG. 5—that each belong to a separate electrical phase, a total of six power amplifiers is provided in the amplifier unit. In this respect, in accordance with a preferred variant, each power amplifier is designed as a bipolar power amplifier in a known manner as an H bridge circuit. The name "bipolar power amplifier" means that both the phase currents and the phase voltages can each adopt a positive and a negative sign.

Another variant for the power amplifiers of the amplifier unit for a separate regulation of the coil currents (or coil voltages) in the coils 61 or in the groups of coils 61 is that each power amplifier is a respective bridge branch of the amplifier unit. A respective one bridge branch of the amplifier unit is provided as a separate bipolar power amplifier for each of the coils 61 or for each of the separate electrical phases. Each coil 61 or each group is, on the one hand, connected to the bipolar power amplifier supplying it. On the other hand, each coil 61 or each group of coils 61 is connected to a common neutral point that is at a center point potential. The neutral point is preferably configured as a loadable neutral point, that is it is connected to a loadable potential so that, apart from the six coil currents, an additional current can flow off over the neutral point or can flow into it. This means that the usual neutral point condition that the sum of the coil currents at the neutral point always has to be zero is no longer necessary with this circuit. This has the consequence that each coil current can also be regulated completely independently of the other coil currents in this variant.

In accordance with another preferred variant, the coils 61 or the groups of coils 61 are supplied using conventional A.C. controllers, wherein an A.C. controller typically has three electrical phases. It is thus possible in the variant shown in FIG. 7, for example, to supply six separate coils using two independent A.C. controllers of which each supplies three coils 61. In this respect, the two A.C. controllers are separate from one another, i.e. in particular their neutral points, are separate from one another or independent of one another. The same naturally also applies analogously to groups of coils 61.

It is also in particular advantageously possible in the embodiment having separate drive coils 62 and separate control coils 63 to provide the respective phase currents in the drive coils 62 and control coils 63 using conventional A.C. controllers, wherein an A.C. controller can typically supply three electrical phases.

Figure 17:
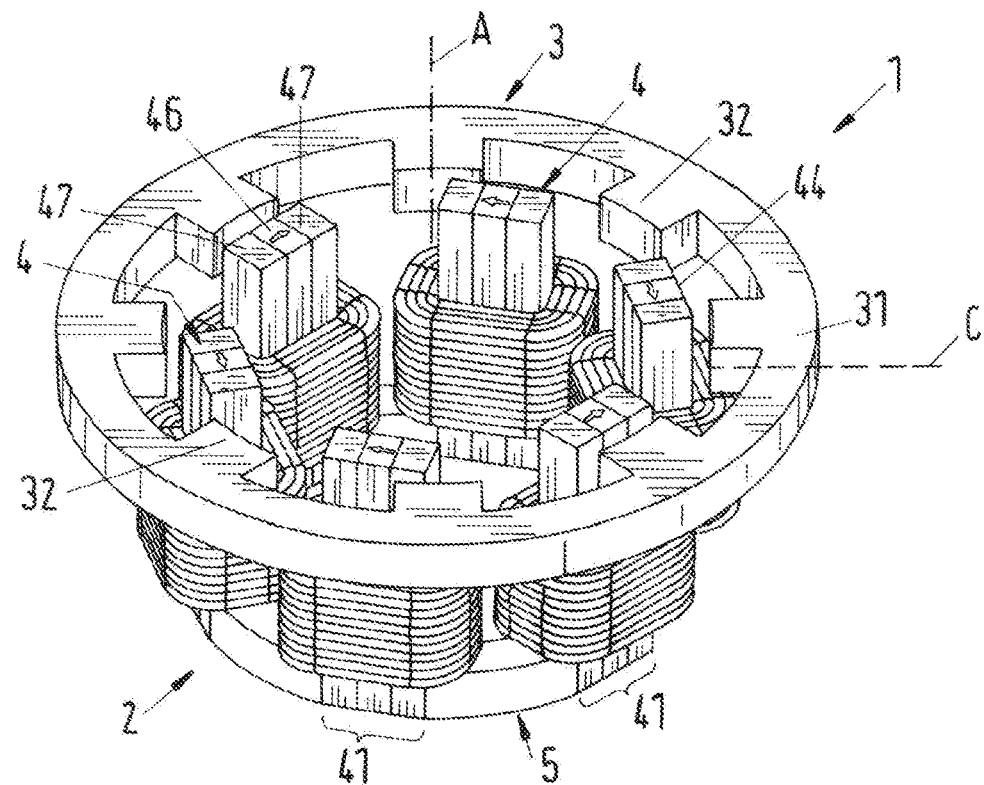
FIG. 17 is a perspective representation of a fifth embodiment of an electromagnetic rotary drive in accordance with the invention.

As already mentioned, the electromagnetic rotary drive 1 in accordance with the invention can also be configured as an external rotor, that is with an inwardly disposed stator 2 and with a rotor 3 radially outwardly surrounding the stator. FIG. 17 shows in a perspective representation a fifth embodiment of an electromagnetic rotary drive 1 in accordance with the invention that is configured as an external rotor.

In the following, only the differences from the above-described embodiments will be looked at. The reference numerals in particular have the same meaning as has already been explained in connection with the embodiments described above. It is understood that all the above explanations also apply in the same manner or in accordingly the same manner to the fifth embodiment.

The fifth embodiment corresponds to the embodiment shown in FIG. 5 with respect to the configuration of the stator 2. The rotor 3 is here arranged as an external rotor, that is such that it surrounds the second ends 44 of the longitudinal limbs 41 of the coil cores 4 disposed outwardly with respect to the radial direction. For this purpose, the magnetic core 31 is of ring shape with a plurality of pronounced rotor teeth 32—eight here—that each extend inwardly with respect to the radial direction, that is face the second ends 44 of the longitudinal limbs 41 of the coil cores 4.

Figure 18:
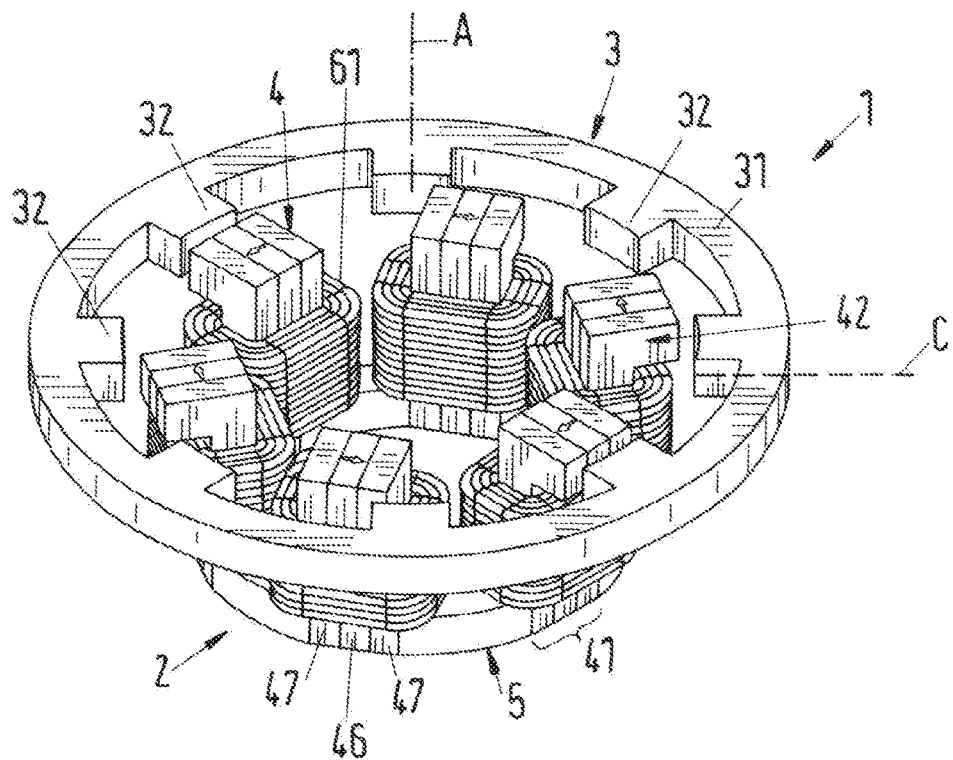
FIG. 18 is a perspective representation of a sixth embodiment of an electromagnetic rotary drive in accordance with the invention.

FIG. 18 shows a perspective representation of a sixth embodiment of a rotary drive in accordance with the invention that is likewise configured as an external rotor and that otherwise corresponds to the embodiment shown in FIG. 7. For better understanding, FIG. 19 shows a section through the sixth embodiment in the axial direction.

In the following, only the differences from the above-described embodiments will be looked at. The reference numerals in particular have the same meaning as has already been explained in connection with the embodiments described above. It is understood that all the above explanations also apply in the same manner or in accordingly the same manner to the sixth embodiment.

The configuration of the stator 2 of the sixth embodiment largely corresponds to the configuration explained in connection with FIG. 7. Each coil core 4 here also comprises two respective L-shaped permanent magnet-free portions 47 and one L-shaped permanent magnetic portion 46 that is arranged between the two permanent magnet-free portions 47.

Since it is an external rotor, the transverse limbs 42 are, however, here respectively aligned outwardly in the radial direction, that is toward the rotor 3. The rotor 3 has the magnetic core 31 that is of ring shape and has a plurality of pronounced rotor teeth 32—eight here—that each extend inwardly with respect to the radial direction, that is that face the transverse limbs 42 of the coil cores 4.

In the following, different variants for the preferred configuration of the coil cores 4 having the longitudinal limbs 41 will be explained with reference to FIGS. 20 to 23, in which configuration each coil core 4 has the two permanent magnet-free portions 47 and the permanent magnetic portion 46 arranged therebetween. These explanations apply in accordingly the same manner both to those coil cores 4 that do not have any transverse limbs 42 (see e.g. FIG. 5) and to those coil cores 4 that have both a longitudinal limb 41 and a transverse limb 42 in which therefore the permanent magnet-free portions 47 and the permanent magnetic portion 46 are each of L shape.

As already mentioned, the permanent magnet-free portions 47 of the coil core 4 are produced from a soft magnetic material that easily conducts the magnetic flux. Preferred soft magnetic materials comprise iron, nickel iron or silicon iron.

The permanent magnet-free portions 47 of each coil core 4 are preferably configured in bundled laminate form. This can be recognized in each of the FIGS. 20 to 23 that each show a variant for the configuration of the coil core 4 in a perspective representation. In the configuration in bundled laminate form, each permanent magnet-free stator part 47 is made up of a plurality of thin elements 48 that are stacked on one another in parallel with one another. All the elements 48 are of identical configuration, that is here are each of L shape and also have the same thickness. As can be recognized in FIGS. 20 to 23, the elements 48 that form the permanent magnet-free portion 47 are stacked in the peripheral direction of the rotor 3 or of the stator 2. A plurality of congruent, parallel elements 48 therefore form the permanent magnet-free portion 47. So that the individual elements 48 remain together, they can be adhesively bonded or molded with a plastic. This molding can naturally comprise the total coil core 4. Eddy currents in the permanent magnet-free portions 47 can be effectively suppressed or reduced by this configuration in bundled laminate form.

In the variant shown in FIG. 20, the permanent magnetic portion 46 arranged between the two permanent magnet-free portions 47 and of L shape is in one piece. Its magnetization is indicated by the arrow without reference numerals.

In the variant in accordance with FIG. 21, the permanent magnetic portion 46 is composed of two bar-shaped segments 461 of which the one has its longitudinal extent in the axial direction A and the other has its longitudinal extent in the radial direction.

Figure 22:
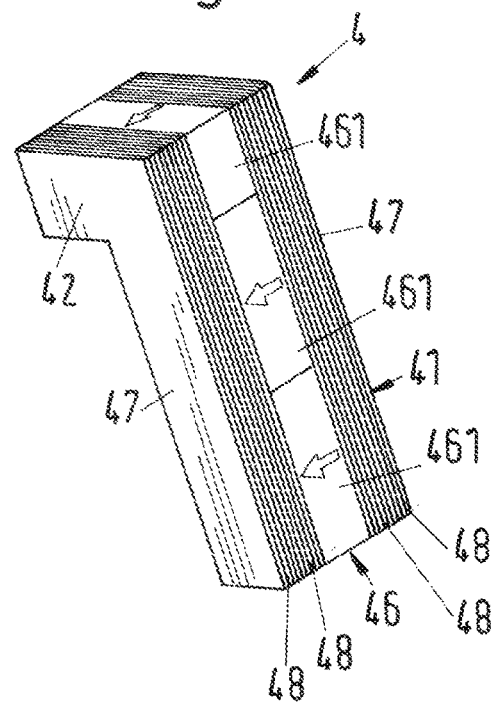

In the variant in accordance with FIG. 22, the permanent magnetic portion 46 is composed of three bar-shaped or parallelepiped-shaped segments 461 of which two have their longitudinal extent in the axial direction A and the third has its longitudinal extent in the radial direction.

Figure 23:
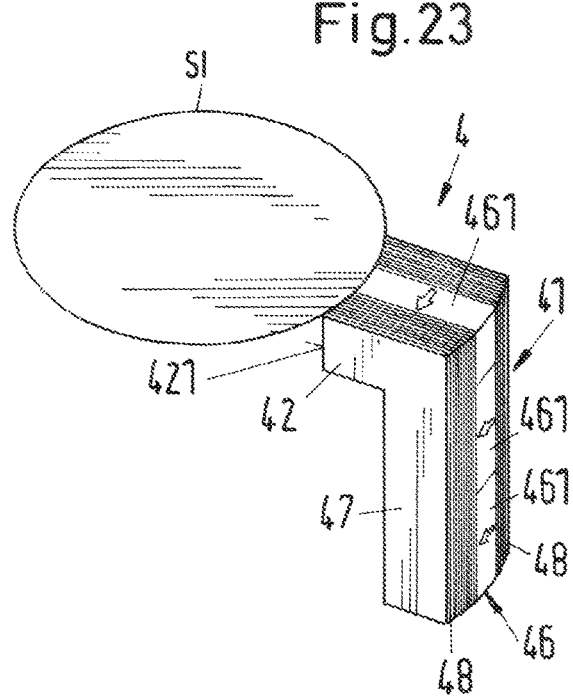

FIG. 23 illustrates a measure that is advantageous in a number of applications with respect to the configuration of the L-shaped coil cores 4. In this variant, the end face 421 of the transverse limb 41 facing the rotor 3 is curved, and is indeed curved such that it follows the curvature of the radial outer side of the rotor 3. If the curvature of the end face 421 is adapted to the rotor 3, it follows that, e.g. with a disk-shaped rotor 3, that the air gap between the coil core 4 and the rotor 3 has an extent in the radial direction that is constant viewed over the total end face 421. A spatially very homogeneous magnetic flux can be realized in this air gap. Such a configuration can be implemented, for example, in that the individual elements are successively slightly displaced with respect to one another with respect to the radial direction to achieve the curvature of the end face 421. In FIG. 23, the inner circle that bounds the coil cores 4 in a radially inwardly disposed manner is indicated by the circle having the reference symbol SI. The individual elements 48 of the permanent magnet-free portions 47 are then each displaced in the radial direction with respect to one another such that their ends forming the respective end faces 421 follow the contour of the inner circle SI.

It is understood that in a configuration as an internal rotor such as is indicated in FIG. 23 the end face 421 is concavely arched in the peripheral direction, while it is convexly arched in a configuration as an external rotor.

In the following, different additional variants for the configuration of the rotor 3, more exactly for the configuration of the magnetically effective core 31 of the rotor 3, will now be explained, with reference being made to the configuration as an internal rotor. The rotor 3 is coil-free and free of permanent magnets as a reluctance rotor. The magnetically effective core 31 of the rotor 3 or all of its parts is/are preferably produced from a soft magnetic material, for example from iron, nickel iron or silicon iron. In this respect, the magnetically effective core 31 can e.g. be manufactured by casting, stamping, pressing of soft magnetic powder with subsequent sintering, forging, shaping or assembling of parts such as metal sheets. The rotor 3 can therefore in particular also be configured in bundled laminate form, in an analog manner such as explained with respect to the coil cores 4, that is from a plurality of thin elements that are then stacked in parallel with one another and that are, for example, fixed by a plastic jacket or by a molding in plastic. Unlike the coil cores 4, in a configuration in bundled laminate form of the magnetically effective core 31 of the rotor 3, the individual elements are preferably stacked in the axial direction A. It is naturally also possible to stack the individual elements in the radial direction in the configuration in bundled laminate form such that the boundary surfaces extend in parallel with the axial direction A between adjacent elements.

First, some variants and measures for the configuration of the magnetically effective core 31 of the rotor 3 will be explained in which the anisotropy in the rotor magnetization required for a reluctance rotor is implemented by the geometric configuration of the magnetically effective core 31 of the rotor 3, that is, for example, by pronounced rotor teeth 32. It is understood that the respective number of rotor teeth 32 is to be understood by way of example. The skilled person can determine an optimum number of rotor teeth without problems in dependence on the application and in particular in dependence on the configuration of the stator 2, especially in dependence on the number of coil cores 4. The measures explained in connection with the individual variants can naturally also be combined with one another or can be combined with the already described configurations of the rotor 3.

In the variants for the configuration of the magnetically effective core 31 of the rotor 3 described in the following, the magnetically effective core 31 is always of disk shape or ring shape with respect to the axial direction A, wherein the axial height HR of the magnetic core 31 (cf. FIG. 13) is preferably at most as large as the height HS in the axial direction A of the end faces 421 of the coil cores 4 facing it.

Figure 24:
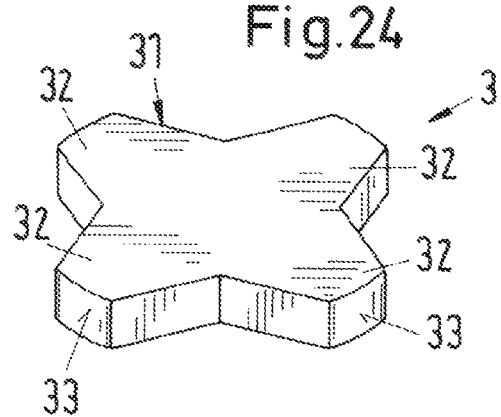
FIGS. 24 to 28 are different variants for the embodiment of the rotor, each in a perspective representation.

In the representation shown in a perspective representation in FIG. 24, the magnetic core 31 of the rotor 3 is substantially of cross shape and has four pronounced ring teeth 32. In this respect, each rotor tooth 32 is trapezoidal such that it tapers toward the stator 2 in the radial direction. The radially outwardly disposed boundary surfaces 33 of each rotor tooth 32 are each curved—convexly here. Together with a curved configuration of the end faces 421 of the coil cores 4 as shown in FIG. 23, the air gap between the radially outwardly disposed boundary surfaces 33 of the rotor tooth 32 and the end faces 421 thus has a constant radial extent viewed in the peripheral direction, which leads to an advantageous very homogeneous flux distribution in this air gap.

Figure 25:
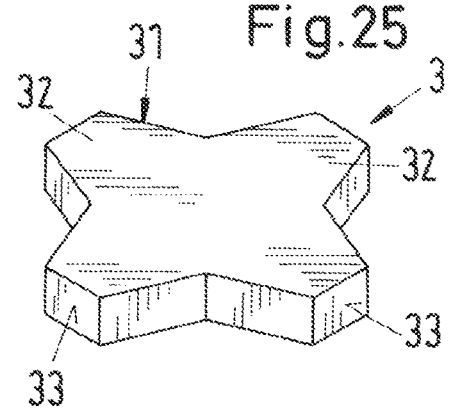

The variant of the magnetic core 31 shown in a perspective representation in FIG. 25 substantially corresponds to that shown in FIG. 24, but the radially inwardly disposed boundary surface 33 of each rotor tooth 23 are of planar configuration, that is are not curved, in the variant in accordance with FIG. 25. This configuration is in particular preferred when the end faces 421 of the coil cores 4 are also planar, that is are not curved.

Figure 26:
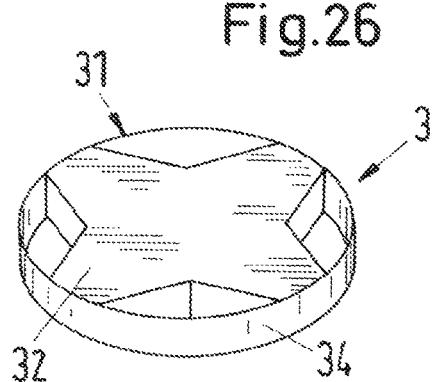

The variant of the magnetic core 31 shown in a perspective representation in FIG. 26 largely corresponds to that shown in FIG. 25. However, the magnetic core 31 in the variant in accordance with FIG. 26 additionally comprises a closed, radially outwardly disposed ring 34, for example an iron bridge, that extends over the total periphery of the magnetically effective core 31 and bounds it with respect to the radial direction. The ring 34 therefore forms the radially outer boundary surface of the magnetically effective core 31. The measure of the radially outwardly disposed ring 34 is in particular advantageous with respect to the sensor system with which the radial position of the rotor 3 and its rotational position are determined. It is namely ensured by the radially outwardly disposed ring 34 that the desired spacing of the magnetically effective core 31 of the rotor 3 from the stator 3 is a constant value viewed over the total periphery of the magnetic core 31. The desired spacing is in this respect the radial spacing between the rotor 3 and the stator 2 when the rotor 3 is in the centered and non-tilted position in the radial plane. The uniformity of the desired spacing over the peripheral direction of the rotor 3—that is along the ring 34—in particular allows a simpler metrological detection of the radial position of the rotor 3 in the operating state because the desired spacing of the magnetic core 31 is of an equal amount and is constant for all coil cores 4 independently of the then current angular position of the rotor 3.

Figure 27:
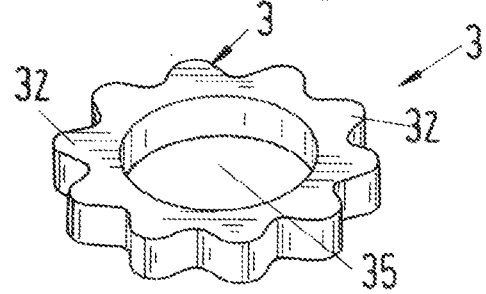

FIG. 27 shows a variant in a perspective representation in which the magnetically effective core 31 of the rotor 3 is substantially of ring shape and has a plurality of pronounced rotor teeth 32. The magnetically effective core 31 therefore has a circular hole 35 at its center. Designing the magnetic core 31 in ring shape, that is with the hole 35, allows the mass of the magnetically effective core 31 to be reduced in comparison with a disk-shaped configuration, that is without a hole 35. The total rotor 3 can thus also be configured with a lower weight, which is an advantage for some applications. In addition, soft magnetic material can be saved, whereby the material costs in the manufacture of the rotor 3 are reduced. The magnetically effective rotor 31 in turn has a plurality of pronounced rotor teeth 32—ten here. In this respect, the rotor teeth 32 are rounded at their radially outwardly disposed ends and the transition region between two adjacent rotor teeth 32 is also rounded. These rounded portions can be designed such that they at least approximately follow a harmonious function such as a sine function overall viewed in the peripheral direction of the magnetically effective core 31.

Figure 28:
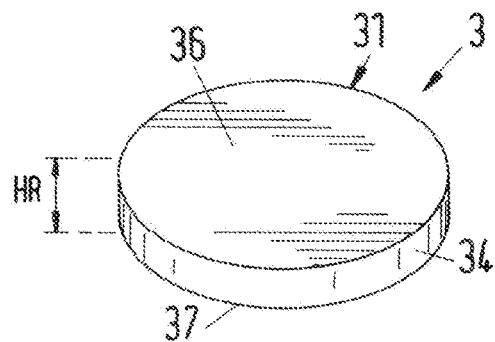

FIG. 28 shows a variant in a perspective representation in which the magnetically effective core 31 of the rotor 3 comprises two circular cover disks, namely a lower cover disk 37 and an upper cover disk 36 that bound the magnetically effective core 31 upwardly and downwardly in the axial direction A. In addition, the radially outwardly disposed ring 34 is provided that bounds the magnetically effective core 31 with respect to the radial direction.

A magnetically effective core 31 that is configured in accordance in with FIG. 28 can be manufactured, for example, in that the variant of FIG. 26 additionally includes the upper cover disk 36 and the lower cover disk 37. The two cover disks 36 and 37 are preferably also composed of a soft magnetic material such as iron. This encapsulation by the radially outwardly disposed rings 34 and of the two cover disks 36, 37 provides the magnetically effective core 31 with the outer shape of a circular disk overall or of a circular cylinder of the height HR and thus a particularly symmetrical outer form. This is advantageous in a number of cases with respect to the sensor system for the detection of the radial position and of the angular position. This has already been explained in connection with FIG. 26 with respect to the ring 34. The cover plates 36, 37 also provide the magnetically effective core 31 with an outer shape that is as homogeneous and as symmetrical as possible viewed in the axial direction A. This is in particular advantageous when the sensor system comprises position sensors that are arranged outside the magnetic rotor plane C with respect to the axial direction A, for example above or below the magnetically effective core 31. Such sensors can, for example, measure in the axial stray field of the magnetically effective core 31 of the rotor 3 by which the magnetic field is meant that is generated outside the air gap between the magnetically effective core 31 of the rotor 3 and the coil cores 4.

In addition, the disk-shaped outer design of the magnetically effective core 31 has the advantage that the magnetic core 31 can be joined in a particularly simple manner to other components to form the rotor 3, for example to plastic jackets, vanes, mixing elements, etc.

Figure 29:
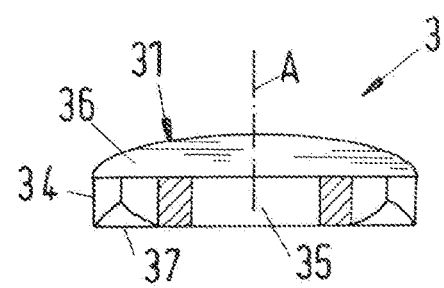
FIG. 29 is a section through a variant for the embodiment of the rotor in an axial direction.

It is understood that this encapsulation by the ring 34 and the two cover disks 36 and 37 can also be used as an additional measure in all other embodiments of the magnetically effective core 31 of the rotor. FIG. 29 shows as an example the magnetically effective core 31 of the variant of FIG. 27 in a section in the axial direction A in which the radially outwardly disposed ring 34 and the two cover disks 36 and 37 are additionally provided.

Figure 30:
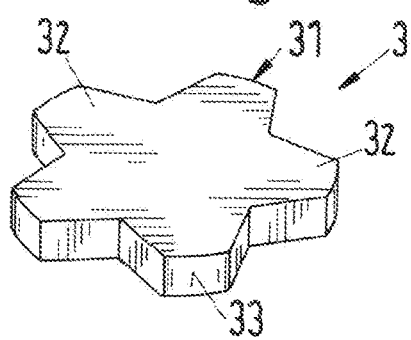
FIGS. 30 to 34 are different variants for the embodiment of the rotor, each in a perspective representation.

FIG. 30 shows a variant in a perspective representation in which the magnetically effective core 31 of the rotor 3 is designed in a similar manner to the variant in accordance with FIG. 24; however, the magnetically effective core 31 has six pronounced rotor teeth 32 in the variant in accordance with FIG. 30.

Figure 31:
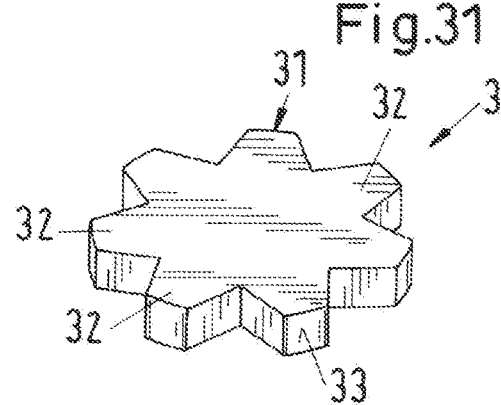

FIG. 31 shows a variant in a perspective representation in which the magnetically effective core 31 of the rotor 3 is designed in a similar manner to the variant in accordance with FIG. 25; however, the magnetically effective core 31 has seven pronounced rotor teeth 32 in the variant in accordance with FIG. 31.

Figure 32:
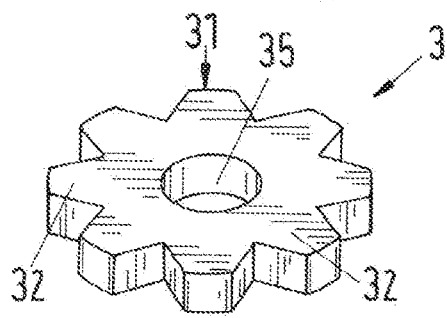

FIG. 32 shows a variant in a perspective representation in which the magnetically effective core 31 of the rotor 3 is designed in a similar manner to the variant in accordance with FIG. 31; however, the magnetically effective core 31 in the variant in accordance with FIG. 32 has eight pronounced rotor teeth 32 and the circular hole 35 in the center of the magnetically effective core 31 is additionally provided such that it is configured substantially in ring shape.

Figure 33:
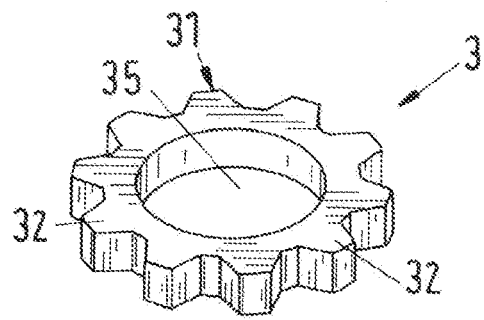

FIG. 33 shows a variant in a perspective representation in which the magnetically effective core 31 of the rotor 3 is designed in a similar manner to the variant in accordance with FIG. 32; however, the magnetically effective core 31 has ten pronounced rotor teeth 32 in the variant in accordance with FIG. 33 and the diameter of the hole 35 is larger in the radial direction.

Figure 34:
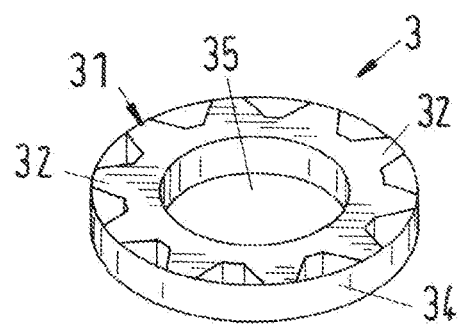

FIG. 34 shows a variant in a perspective representation in which the magnetically effective core 31 of the rotor 3 is designed in a similar manner to the variant in accordance with FIG. 33; however, the magnetically effective core 31 in the variant in accordance with FIG. 34 additionally has the radially outwardly disposed ring 34 that was explained in connection with FIG. 26.

It is understood that many other variants for the design of the magnetically effective core 31 of the rotor 3 are possible; for example by a corresponding combination of the described variants or by varying the number of rotor teeth 32 or their geometrical shape. It is, for example, known to the skilled person that the cogging can be considerably reduced by a larger number of rotor teeth 32 or by variations of their geometries.

Another possibility for the design of the magnetically effective core 31 of the rotor 3 comprises providing the magnetically effective core 31 with flux barriers in a manner known per se. In this respect, the magnetically effective core 31 is designed in disk shape or in ring shape with respect to its outer geometrical shape, for example as a circular cylindrical disk having the height HR in the axial direction (disk-shaped) or as such a disk with a center hole 35 (ring-shaped). The magnetic anisotropy of the magnetically effective core 31 of the rotor 3 is achieved in this embodiment in that flux barriers are added into the magnetically effective core 31. The flux barriers are recesses, for example slits or barrier surfaces, in the ferromagnetic or ferrimagnetic structure of the magnetically effective core 31 that can be filled with air or with another non-soft magnetic material, in particular with a plastic. Since the magnetic flux undergoes a very high magnetic resistance through the non-soft magnetic material, that is e.g. air or plastic, while the soft magnetic material can be considered as a magnetic conductor, any desired magnetic anisotropy can be imposed on the magnetically effective core 31 by a suitable arrangement and configuration of these flux barriers. The flux guidance can in particular be optimized for the demands of both the drive and of the magnetic support using such flux barriers. Pronounced rotor teeth 31 can in particular also be simulated by a corresponding arrangement using such flux barriers, i.e. the magnetically effective core 31 then has substantially the same magnetic anisotropy as can be realized by the geometrical shaping of rotor teeth 32.

The cogging can thus, for example, be greatly reduced with respect to the cruciform magnetically effective core 31 shown in FIG. 5. In principle, rotors 3 of any desired pole number can be implemented using the flux barriers that are optimized both with respect to the magnetic drive and to the passively magnetic stabilization of the tilt and of the axial position of the rotor and to the actively magnetic stabilization of the position of the rotor 3 in the radial plane.

Different variants of how the magnetically effective core 31 of the rotor 3 can be configured with flux barriers will now be explained by way of example with reference to FIGS. 35 to 41.

Figure 35:
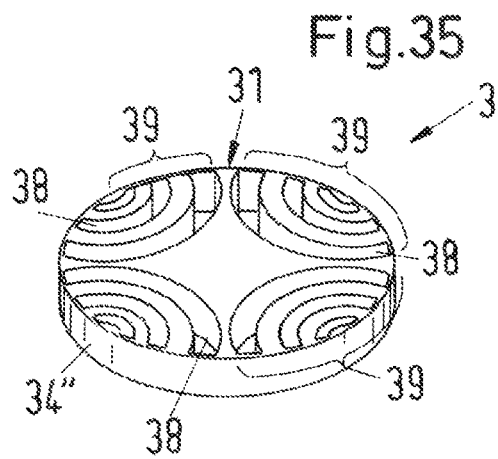
FIGS. 35 to 41 are different variants for the embodiment of the rotor with flux barriers, each in a perspective representation.

FIG. 35 shows in a perspective representation the magnetically effective core 31 of the rotor 3 with a plurality of flux barriers 38 with which a magnetic effect of four pole pairs is imparted to the magnetically effective core 31. A total of four groups 39 of flux barriers 38 is provided. With adjacent groups 39 being respectively arranged offset by 90° with respect to one another with regard to the peripheral direction such that the groups are diametrically opposed pair-wise. Each group 39 comprises a plurality of flux barriers 38 that are designed as quadrant-shaped concentric gaps and that each extend completely through the magnetically effective core 31 in the axial direction A. Each of these quadrant-shaped gaps starts and ends at the radially outwardly disposed boundary surface 34" of the magnetically effective core 31. In this respect, the radially outwardly disposed boundary surface 34" is a contiguous surface that is not penetrated by the gaps. The same advantage thus results with regard to the sensor system as has already been explained in connection with FIG. 26 for the ring 34. The gaps forming the flux barriers 38 can be configured as air gaps or they can be filled with a magnetically poorly conducting material, in particular with a plastic.

Figure 36:
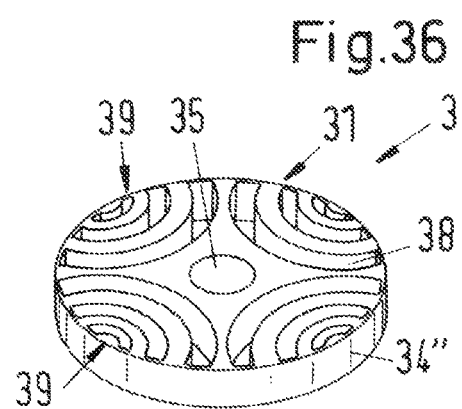

FIG. 36 shows a variant in a perspective representation in which the magnetically effective core 31 of the rotor 3 is designed in a similar manner to the variant in accordance with FIG. 35; however, the magnetically effective core 31 additionally has the central hole 35, that is it is configured in ring shape, in the variant in accordance with FIG. 36.

Figure 37:
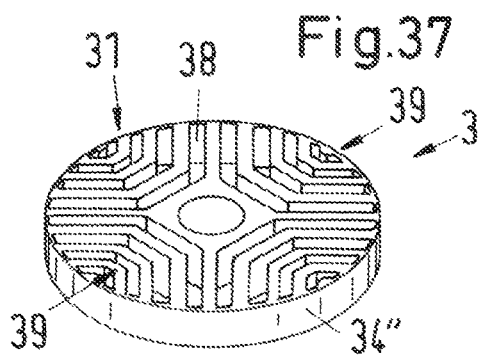

FIG. 37 shows a variant in a perspective representation in which the magnetically effective core 31 of the rotor 3 is configured in a similar manner to the variant in accordance with FIG. 36; however, the individual gaps of the flux barriers 38 in the variant in accordance with FIG. 37 are not of quadrant shape, but are rather substantially trapezoidal. Each gap comprises two parts of which each extends radially inwardly from the boundary surface 34", with the two parts extending at a right angle to one another. The radially inwardly disposed ends of these two parts are then connected to one another such that the substantially trapezoidal configuration results.

Figure 38:
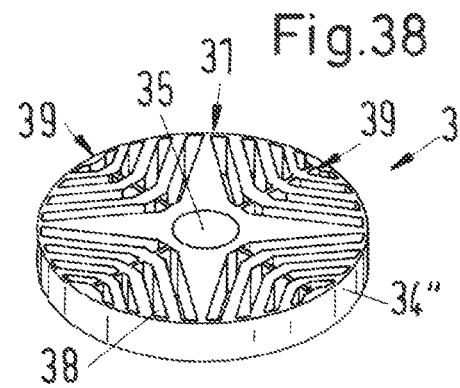

FIG. 38 shows a variant in a perspective representation in which the magnetically effective core 31 of the rotor 3 is configured in a similar manner to the variant in accordance with FIG. 37; however, the individual gaps of the flux barriers 38 are approximately triangular in the variant in accordance with FIG. 38. Each gap in turn comprises the two parts that each extend inwardly from the boundary surface 34" The two parts, however, now no longer extend in the radial direction, but rather toward one another such that their radially inwardly disposed ends meet or almost meet.

Figure 39:
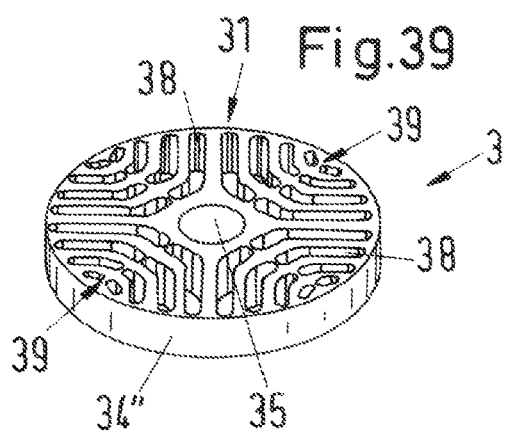

FIG. 39 shows a variant in a perspective representation in which the magnetically effective core 31 of the rotor 3 is configured in a similar manner to the variant in accordance with FIG. 37. The individual gaps of the flux barriers 38 are again substantially trapezoidal, with each gap comprising the two parts of which each extends radially inwardly from the boundary surface 34"; however, in the variant in accordance with FIG. 39, the connection between the radially inwardly disposed ends of these two parts is no longer continuous, but is rather interrupted by a web.

Figure 40:
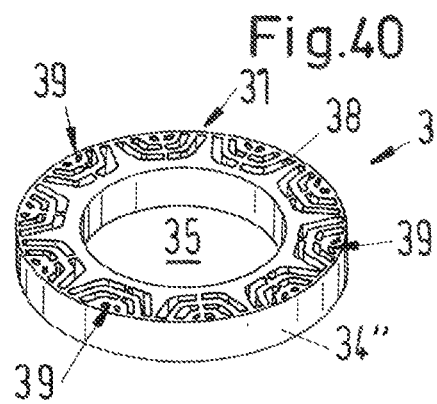

FIG. 40 shows a variant in a perspective representation in which the magnetically effective core 31 of the rotor 3 is configured in a similar manner to the variant in accordance with FIG. 39; however, in the variant in accordance with FIG. 40, a total of ten groups 39 of flux barriers 38 is provided by which a magnetic effect of ten pole pairs is imparted to the magnetically effective core 31. In addition, the diameter of the central hole 35 is configured as larger in the radial direction.

Figure 41:
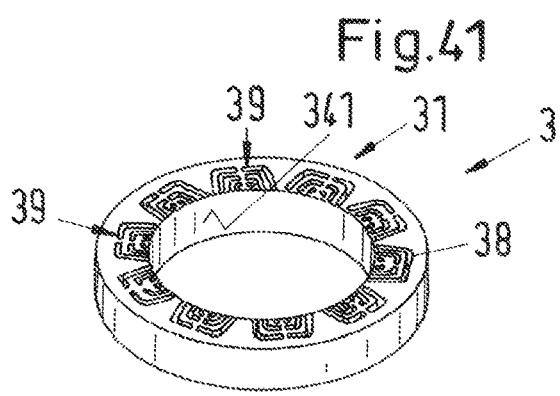

FIG. 41 shows a variant in a perspective representation in which the magnetically effective core 31 of the rotor 3 is configured for an external rotor. The configuration of the flux barriers 38 is designed in accordingly the same manner as in the variant in accordance with FIG. 40; however, its arrangement in FIG. 41 is now designed for an external rotor. That is, the two parts of the radially inwardly disposed boundary surface 341 of the magnetically effective core 31 now extend outwardly viewed in the radial direction in the respective substantially trapezoidal gaps of the flux barriers 38. A magnetic effect of ten pole pairs is also imparted to the magnetically effective core 31 in the external rotor variant in accordance with FIG. 41.

A number of methods are known per se for the manufacture of the magnetically effective core having the flux barriers 38. It is thus possible, for example, to generate the flux barriers 38 in a disk-shaped or ring-shaped base body by stamping or by cutting or by another stock-removing method. In a bundled laminate embodiment of the magnetically effective core 31, the individual elements can, for example, be provided with corresponding recesses or gaps by cutting or stamping before they are stacked such that the desired arrangement and configuration of the flux barriers 38 results after the stacking of the elements.

Embodiments of the position sensor system and arrangements of the position sensors will now be explained in the following, wherein reference is made with an exemplary character to the configuration of the stator 2 in accordance with FIG. 7 and to the configuration of the rotor 3 in accordance with FIG. 7. It is understood that the following explanations are not restricted to this configuration of the stator 2 and of the rotor 3, but rather also apply in accordingly the same manner to all other configurations of the stator 2, of the rotor 3 and of their combinations.

The radial rotor position and the angle of rotation must be known or must be metrologically determined for the regulation and for the control of a bearingless motor and thus also for the specific configuration as a temple motor 1. In this respect, the radial rotor position means the radial position of the rotor 3 in the radial plane. The radial plane is that plane in which the rotor 3 is magnetically supported in the operating state. If the rotor 3 is therefore free of tilts, the radial plane coincides with the magnetic rotor plane C. The angle of rotation of the rotor 3 indicates the relative angular position of the rotor 3 with respect to the stator 2 on its rotation about the axial direction A. This angle of rotation can be measured, for example, in that an x axis of any desired orientation and a y axis perpendicular thereto are fixed in the x-y plane, that is in the radial plane, the axes being in a fixed position with respect to the stator 2. The instantaneous angle of rotation of the rotor 3 can then be determined as an instantaneous angle with respect to this x axis (or naturally also to the y axis).

Figure 42:
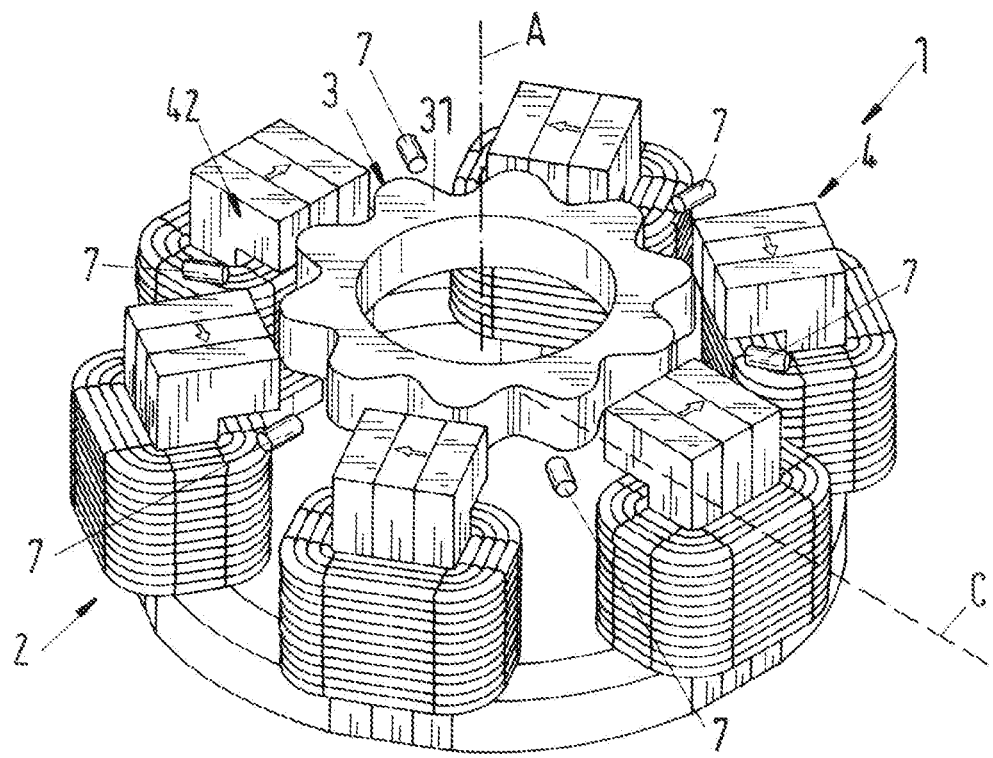
FIGS. 42 to 45 are different variants for the arrangement of sensors, each in a perspective representation.

FIG. 42 shows in a perspective illustration the stator in accordance with FIG. 7 in combination with the magnetically effective core 31 of the rotor 3 in accordance with the variant in FIG. 27.

Furthermore a total of six position sensors 7 are shown in FIG. 42 by which the radial rotor position—that is its position in the radial plane or in the x-y plane—can be determined. The position sensors 7 are magnetic field sensors and are preferably configured as Hall sensors or as GMR sensors. The position sensors are in signal communication with a control and regulation device, not shown, via signal lines, not shown.

It is a customary and known measure to provide a total of four position sensors 7 to determine the position of the rotor 3 in the radial plane. In this respect, the position sensors 7 are disposed diametrically opposite pair-wise. In principle, two position sensors 7 are sufficient to determine the position of the rotor 3 in the x-y plane, namely one per coordinate direction. It is, however, preferred to provide four position sensors 7 in order thus to allow a more accurate determination of the position of the rotor 3 from the difference signal of the position sensors 7 oppositely disposed pair-wise. Since the angle of rotation of the rotor 3 additionally has to be determined, further position sensors 7 are necessary; in the rotor 3 shown in FIG. 42 or in the magnetically effective core 31, a total of at least five position sensors 7 are required in the general case to determine both the rotor position and the angle of rotation. If the magnetically effective core 31 has a radially outwardly disposed ring 34 such as has been discussed in connection with FIG. 26, the number of required position sensors 7 is thus reduced to four.

In the arrangement shown in FIG. 42, a total of six position sensors 7 is provided that are diametrically opposed pair-wise. The position sensor 7 are all arranged in the radial plane in which the rotor 3 is supported, that is in its magnetic center plane C in the non-tilted state of the rotor 3. The position sensors 7 are distributed equidistantly over the peripheral direction. A position sensor 7 is respectively arranged between the transverse limbs 42 of two adjacent coil cores 4.

Both the radial rotor position and the angle of rotation of the rotor 3 can be determined by this arrangement of the position sensors 7 with the aid of the sensor signals. The position sensors 7 can, for example, respectively be eddy current sensors, optical sensors, capacitive sensors or magnetic field sensors such as Hall sensors or GMR sensors.

It can be an advantageous measure with magnetic field sensors to arrange a small permanent magnet (not shown) behind the sensor if the magnetic field or the stray field is not sufficient for a sufficiently exact measurement at the site of the position sensor 7.

Figure 43:
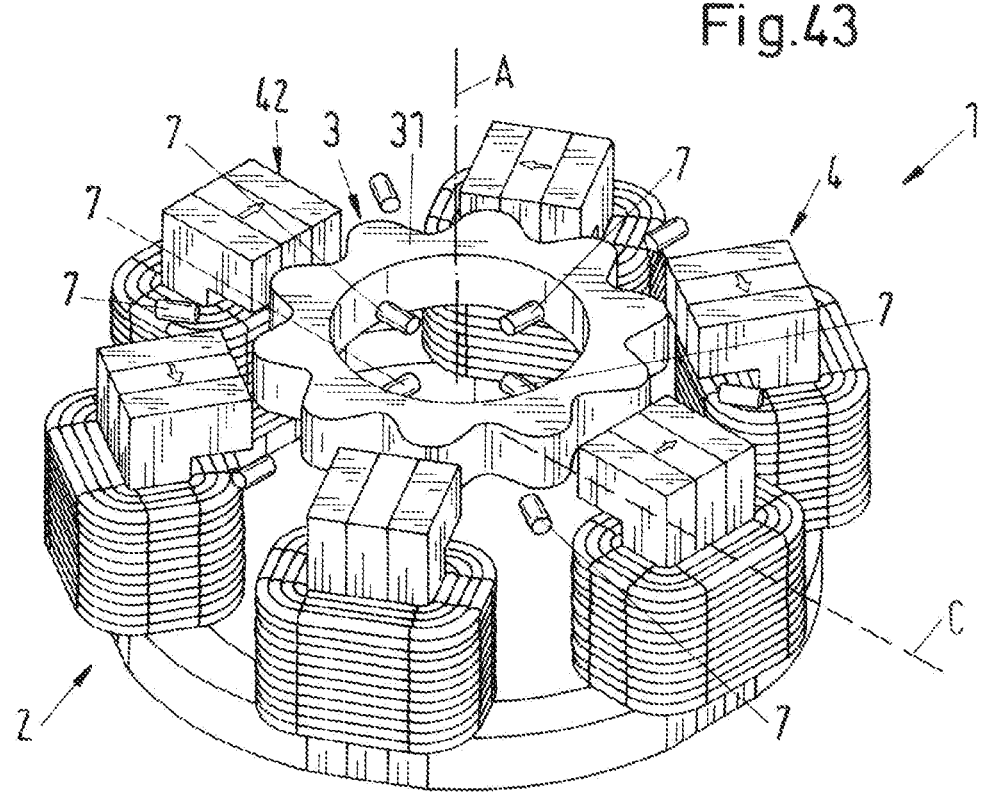

A further variant for the arrangement of the position sensors 7 is shown in a perspective representation in FIG. 43. In addition to the variant shown in FIG. 42, a plurality of position sensors 7—four here—are arranged radially inwardly with respect to the ring-shaped magnetically effective core 31 of the rotor 3 in the radial plane that coincides with the magnetic rotor plane C with a non-tilted rotor in the variant in accordance with FIG. 43. The four position sensors 7 arranged radially inwardly disposed with respect to the magnetic core 31 are preferably also arranged diametrically opposite pair-wise and are distributed equidistantly over the peripheral direction. In order to reliably determine both the radial rotor position and the angle of rotation of the rotor with this arrangement, at least two position sensors 7 should be disposed radially inwardly disposed and two position sensors 7 radially outwardly disposed with respect to the magnetically effective core 31.

Figure 44:
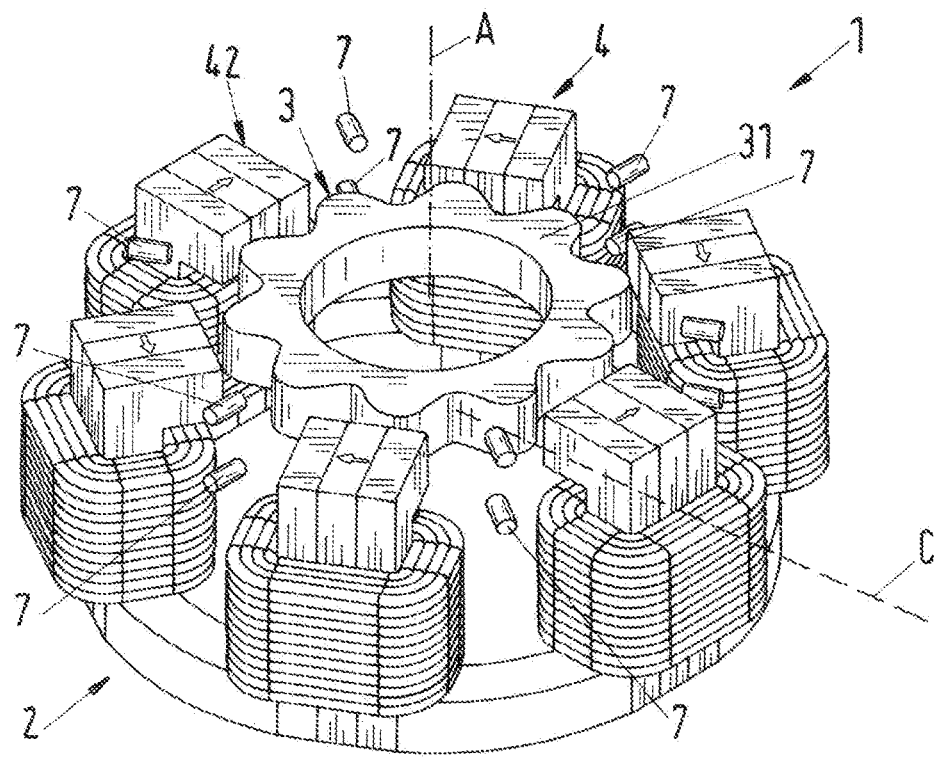

A further variant for the arrangement of the position sensors 7 is shown in a perspective representation in FIG. 44. In addition to the variant shown in FIG. 42, a plurality of further position sensors 7—six here—are provided in the variant in accordance with FIG. 44 that are preferably arranged diametrically opposite one another pair-wise and that are equidistantly distributed over the peripheral direction and that are all arranged outside, that is beneath in accordance with the representation, the radial plane and thus the magnetic rotor plane C. Each of these further position sensors 7 is arranged with respect to its radial placement at the same point as one of the position sensors 7 that are arranged in the radial plane, that is at the same radial position only beneath with respect to the axial direction A. This arrangement has the advantage that the position of the magnetically effective core can additionally also be determined with respect to the axial direction. Tilts of the magnetically effective core 31 with respect to the axial direction A can also be detected.

Figure 45:
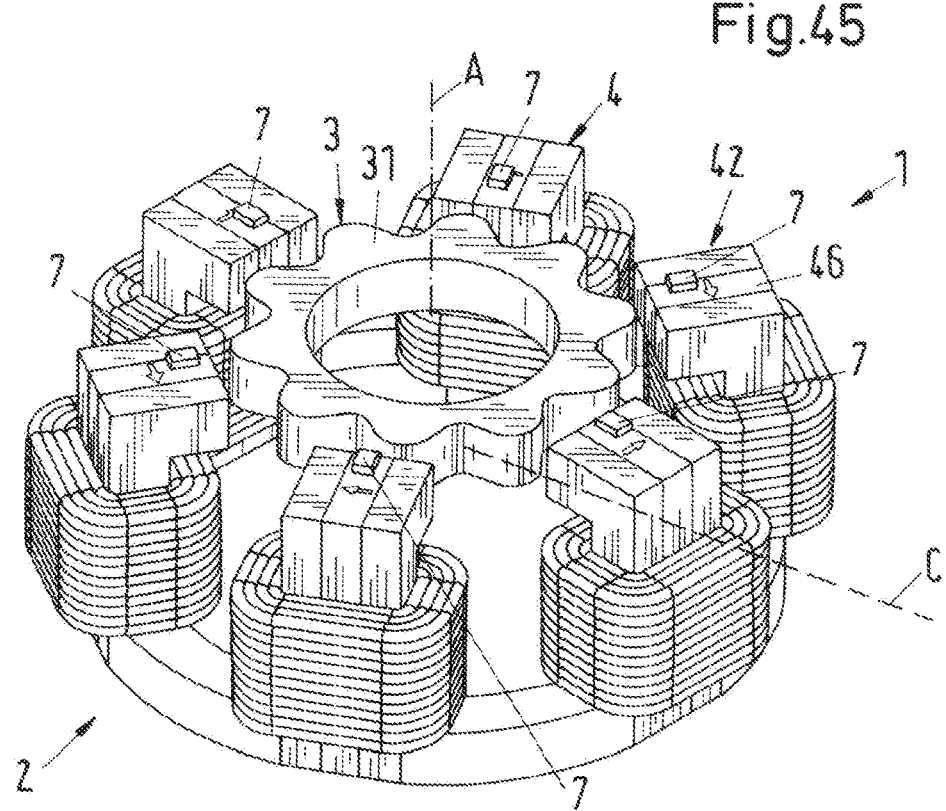
Figure 46:
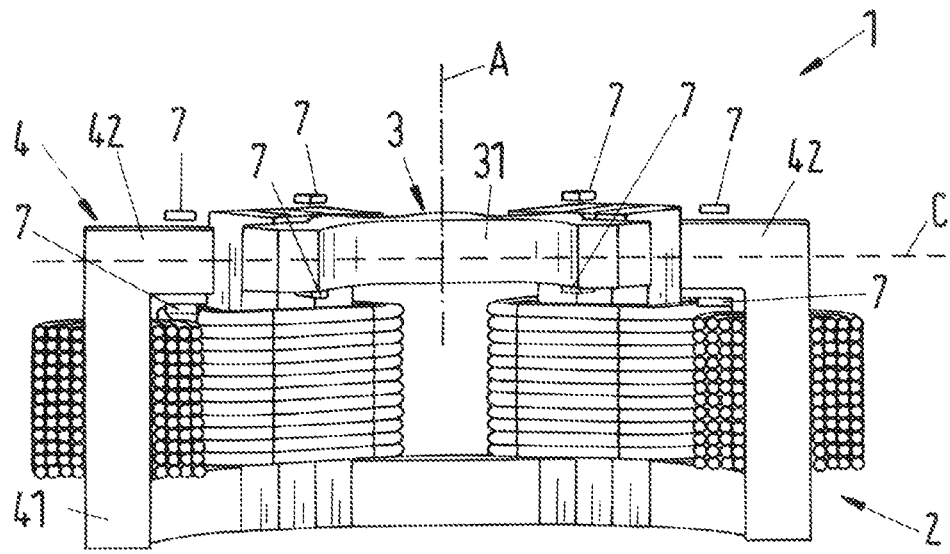
FIG. 46 is a section in an axial direction through the variant for the arrangement of the sensors shown in FIG. 45.

A further variant for the arrangement of the position sensors 7 is shown in a perspective representation in FIG. 45. For better understanding, FIG. 46 shows a section in the axial direction through the variant shown in FIG. 45. In this variant, a total of twelve position sensors 7 is provided that are all arranged outside the radial plane. Exactly two position sensors 7 are provided at each coil core 4 and are arranged above and beneath the transverse limb 42 of the respective coil core 4 with respect to the axial direction A, and indeed such that each position sensor 7 is located above or beneath the permanent magnetic portion 46 of the transverse limb 42. Each position sensor is preferably configured as a Hall sensor or as a magnetic field sensor. It is possible in dependence on the configuration that the magnetic stray field at the site of the position sensors 7 is not sufficient to determine the respective current value of the angle of rotation or of the radial position of the rotor 3. If this stray field is not sufficient, each of the position sensors 7 can respectively be equipped with a small permanent magnet (not shown) that is, for example, adhesively bonded to the respective position sensor 7.

This arrangement of the position sensors 7 above and beneath the transverse limbs 42 is in particular also advantageous under construction aspects. For it is possible to integrate a respective six of the position sensors on a printed circuit board (PCB) and then to arrange one of the printed circuit boards on the transverse limbs 42 and one printed circuit board beneath the transverse limbs 42.

Figure 47:
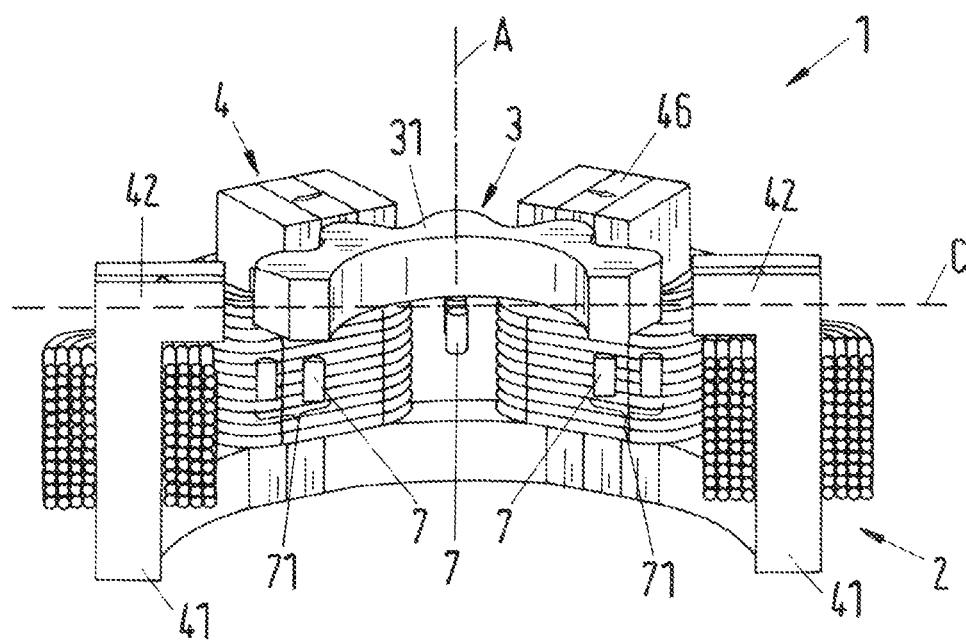
FIG. 47 is a further variant for the arrangement of the sensors in a sectional representation analog to FIG. 46.

A further variant for the arrangement of the position sensors 7 is shown in a section in the axial direction A in FIG. 47. In this arrangement, a total of eight position sensors 7 is present of which only two can be recognized completely and four in section—that is half thereof—in the sectional representation of FIG. 47. Two respective sensors 7 are combined to form a group 71 such that four groups 71 are provided, each having two position sensors 7. All the position sensors 7 are arranged outside the radial plane, namely with respect to the axial direction A beneath the magnetically effective core 31 in the space surrounded by the longitudinal limbs 41. The four groups 71 are arranged diametrically opposite pair-wise and are equidistantly distributed with respect to the peripheral direction. That is, two adjacent groups 71 are each offset by 90° with respect to the peripheral direction. Each group 71 comprises two respective position sensors 7 that are both arranged at the same height with respect to the axial direction A, wherein one of the position sensors 7 is arranged further radially inwardly disposed than the other position sensor 7 of this group 71.

The above-described embodiments and variants of the stator 2 are generally also suitable for other types of rotors, that is also for such rotors that have coils or such rotors that have at least one permanent magnet that contributes to generating the magnetic drive flux. A stator is furthermore proposed by the invention for an electromagnetic rotary drive that is configured as a temple motor, wherein the stator 2 is preferably, but not necessarily, configured as a bearing and drive stator by which a rotor can be driven contactlessly magnetically about a desired axis of rotation and can be contactlessly magnetically supported with respect to the stator 2 in the operating state, wherein the stator is configured as described above. The stator 2 (see e.g. FIG. 7) has a plurality of coil cores 4 of which each comprises a bar-shaped longitudinal limb 41 that extends from a first end 43 in a direction in parallel with the desired axis of rotation up to a second end 44, wherein all the first ends 43 are connected by a reflux 5. A plurality of windings 6, 61 are furthermore provided for generating an electromagnetic rotational field of which each surrounds one of the longitudinal limbs 41. The coil cores 4 comprise a plurality of permanent magnets 46 by which a permanent magnetic drive flux can be generated for driving the rotor 3. Each coil core 4 comprises a permanent magnetic portion 46 that extends from the first end 43 up to the second end 44 of the longitudinal limb 41 and comprises two permanent magnet-free portions 47 that each extend from the first end 43 up to the second end 44. The permanent magnetic portion 46 is arranged between the two permanent magnet-free portions.

The stator 2 in accordance with the invention is suitable both for temple motors in which the rotor is designed free of coils and free of permanent magnets and for temple motors in which the rotor comprises permanent magnets and/or coils.

The stator in accordance with the invention is also suitable for such temple motors that are not configured in accordance with the principle of a bearingless motor, where therefore separate bearings or bearing units, for example magnetic or mechanical ones, are provided for the support of the rotor 3 in addition to the stator 2 generating the drive.

A rotational apparatus for conveying, pumping, mixing or stirring fluids is furthermore proposed by the invention that is characterized in that the rotational apparatus comprises an electromagnetic rotary drive 1 or a stator 2 that is configured in accordance with the invention. The above explanations with respect to the electromagnetic rotary drive 1, to the stator 2 and to the rotor 3 also apply in the same manner or in accordingly the same manner to the rotational machine in accordance with the invention. The reference numerals in particular have the same meaning as has already been explained in connection with the embodiments described above.

Figure 48:
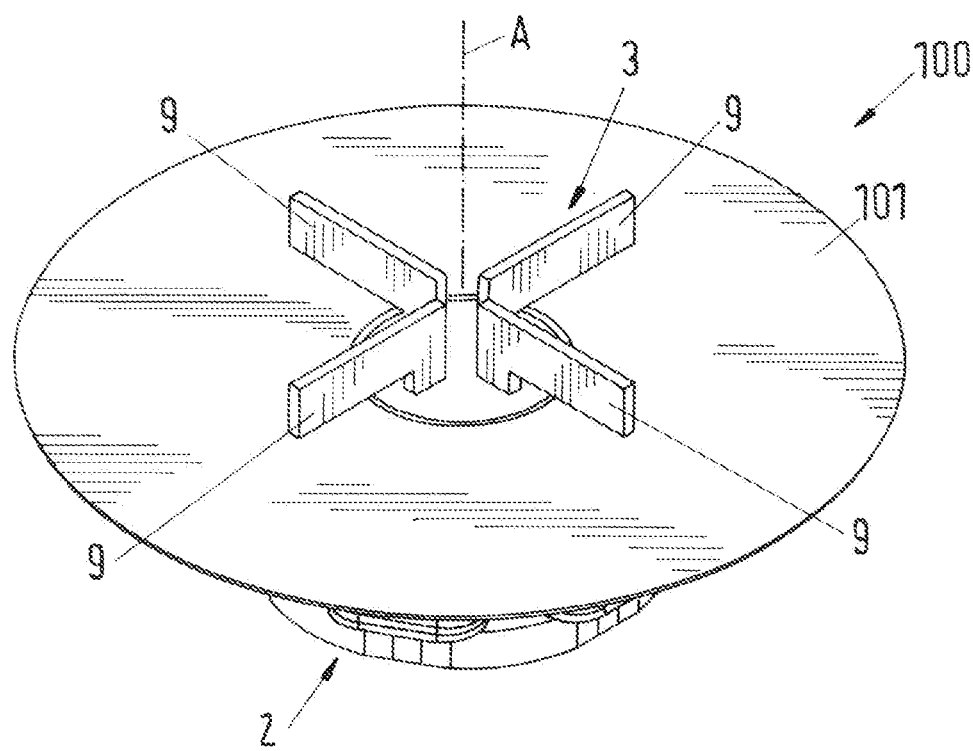
FIG. 48 is a perspective representation of a first embodiment of a rotational apparatus in accordance with the invention that is configured as a mixing apparatus.
Figure 49:
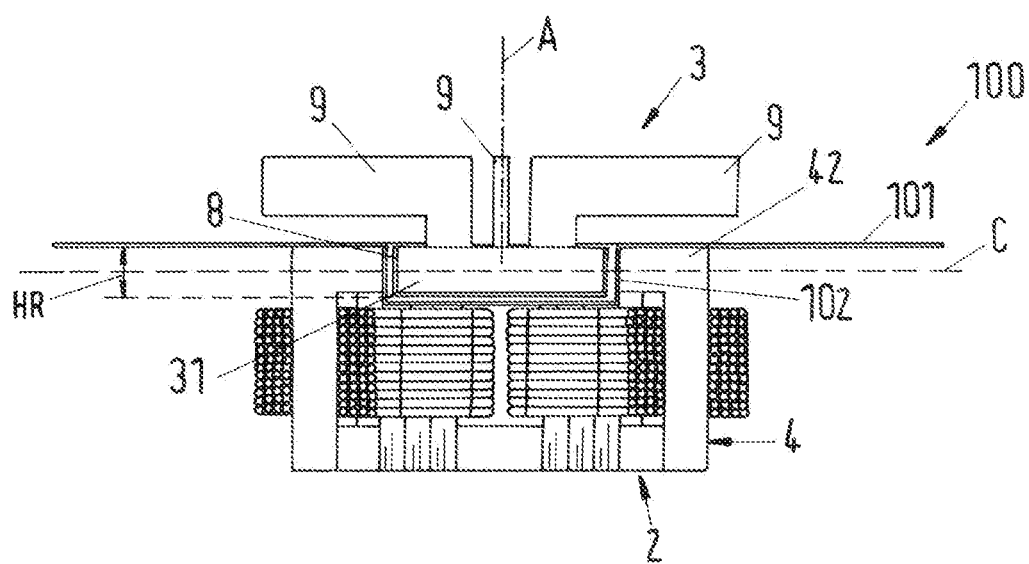
FIG. 49 is a section through the first embodiment of FIG. 48 in an axial direction.

FIG. 48 shows in a perspective representation a first embodiment of a rotational apparatus in accordance with the invention that is configured as a mixing apparatus for mixing or stirring fluids and is designated as a whole by the reference numeral 100. For better understanding, FIG. 49 shows a section through this first embodiment in the axial direction. The mixing apparatus 100 comprises a stator 2 that is configured in accordance with the invention, that is, for example, in accordance with one of the embodiments or variants explained above. The mixing apparatus 100 furthermore comprises a rotor 3 that is, for example, configured in accordance with the preceding explanations and comprises a flange 101 by which the mixing apparatus 100 can be inserted into a mixing tank, not shown. The flange 101 is here configured as a substantially circular disk of stable shape that has a bucket 102 of stable shape at its center to receive the rotor 3 and that is preferably manufactured, including the bucket 102, from a plastic. Examples for suitable plastics will be named further below.

The rotor 3 comprises the magnetically effective core 31 that is enclosed by a jacket 8 that preferably likewise consists of a plastic. The rotor 3 furthermore comprises a plurality of vanes 9—four here—that are arranged at one of the axial boundary surfaces of the magnetically effective core 31 or of its jacket 8. In the representation in accordance with FIGS. 48 and 49, the vanes 9 are arranged at the upper axial boundary surface and are located completely above the magnetic rotary plane C. The vanes 9 are also preferably manufactured from a plastic. The vanes 9 can be manufactured in one piece with the jacket 8 or also as separate components that are then fastened to the jacket 8, for example by welding or adhesive bonding. It is also possible that all the vanes 9 are components of a separate impeller that is then fixed on the magnetically effective core 31 or on its jacket, e.g. by adhesive bonding or welding.

A number of variants are naturally known with respect to the configuration and number of the vanes 9 that will therefore not be looked at in any more detail here.

The bucket 102 serves for the reception of the magnetically effective core 31 and is dimensioned accordingly. The bucket 102 preferably has a circular cross-section perpendicular to the axial direction A, wherein the diameter is dimensioned such that the bucket 102 can be inserted in as exact a fit as possible or with only a very small clearance between the transverse limbs 42 of the coil cores 4 of the stator 2. The depth of the bucket 102 in the axial direction A is dimensioned such that it is somewhat larger than the axial height HR of the magnetically effective core 31 of the rotor 3 such that the rotor 3 can be raised from the base of the bucket 102 by magnetic forces during operation and can rotate freely.

The flange 101 is inserted into a mixing tank, not shown, for the fluids to be mixed or is connected thereto for the operation of the mixing apparatus 100. As a rule, the flange 101 then forms at least one part of the base of the mixing tank. If the mixing tank is configured as a flexible plastic pouch, for example, the flange 101 can be adhesively bonded or welded to the mixing tank with this pouch. If the flange 101 is connected to or inserted into the mixing tank, the bucket 102 forms a sleeve to the outside with respect to the mixing tank. The bucket 102 is inserted into the stator 2 that is typically arranged outside the mixing tank. The rotor 3 is added into the bucket 102 such that the magnetically effective core 31 of the rotor 3 comes to lie completely between the coil cores 4 of the stator 2, more exactly between the transverse limbs 42.

The rotor 3 is then contactlessly magnetically driven to rotate and is contactlessly magnetically supported by the stator 2 in accordance with the principle of a bearingless motor in operation to mix the fluid or fluids in the mixing tank. In this respect, three degrees of freedom of the rotor 3, namely its rotation and its position in the radial plane, can be actively magnetically regulated or controlled by the stator 2, while the rotor 3 is passively magnetically stabilized, i.e. not controllably stabilized, with respect to the three other degrees of freedom, namely its position in the axial direction and tilts with respect to the radial plane. When the rotor 3 is not tilted, the magnetic rotor plane C is identical to the radial plane in which the rotor 3 or its magnetically effective core 31 is supported.

Since the bucket 102 is somewhat deeper with respect to the axial direction A than the axial height HR of the magnetically effective core 31 and additionally has a diameter that is somewhat larger than the magnetically effective core 31, the rotor 3 can rotate contactlessly with respect to the bucket 102 in the operating state. A physical contact between the magnetically effective core 31 or of its jacket 8 and the bucket 102 can be avoided even with slight tilts of the rotor 3 or displacements of its radial and/or axial position.

Figure 50:
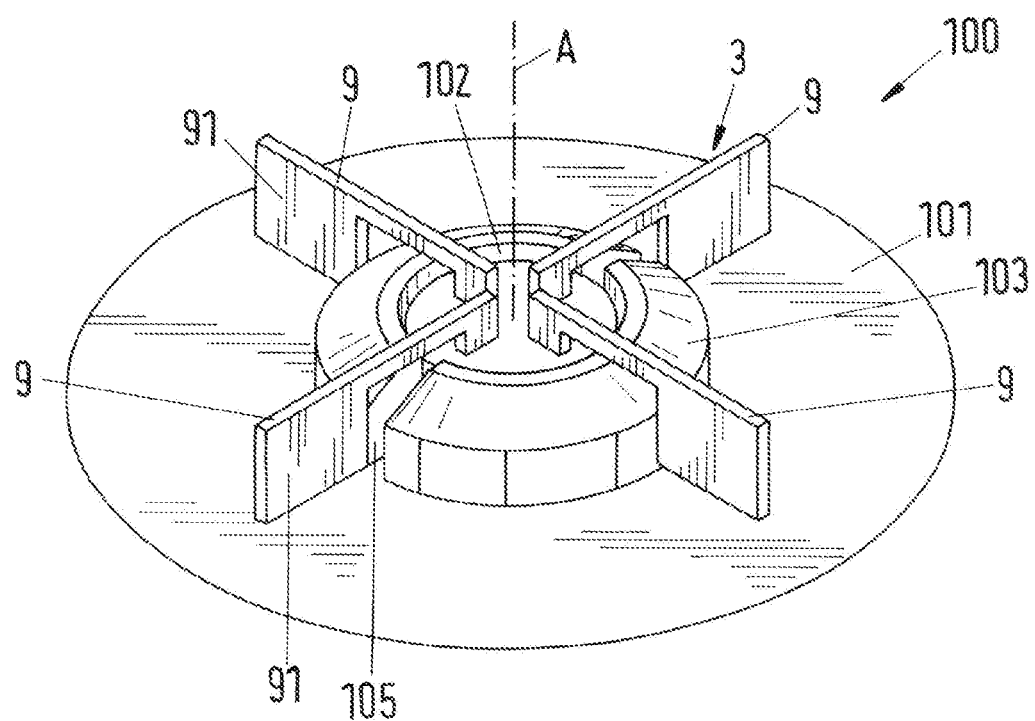
FIG. 50 is a perspective representation of a second embodiment of a rotational apparatus in accordance with the invention that is configured as a mixing apparatus.
Figure 51:
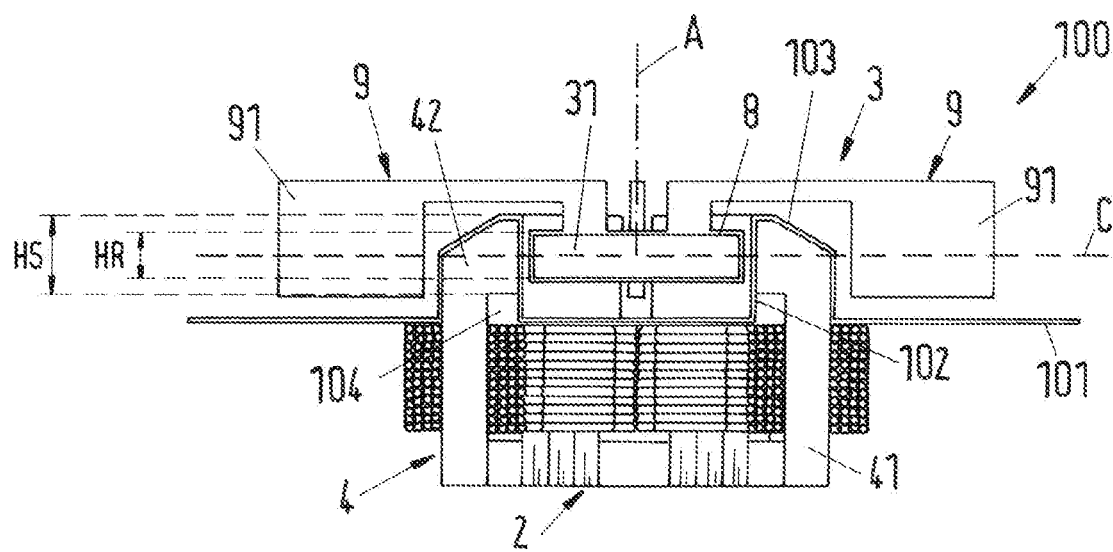
FIG. 51 is a section through the second embodiment of FIG. 50 in an axial direction.

FIG. 50 shows a second embodiment of a rotational apparatus in accordance with the invention in a perspective representation that is likewise configured as a mixing apparatus 100. For better understanding, FIG. 51 shows a section through this second embodiment in the axial direction. Only the differences from the first embodiment of the rotational apparatus will be looked at in the following. The reference numerals in particular have the same meaning as has already been explained in connection with the embodiment described above. It is understood that all the above explanations also apply in the same manner or in accordingly the same manner to the second embodiment.

In the second embodiment, the stator 2 is configured in accordance with the embodiment shown in FIGS. 12 and 13 in which the end faces 421 of the transverse limbs 42 of the coil cores 4 have a height HS in the axial direction A that is respectively larger than the axial height HR of the magnetically effective core 31 of the rotor 3.

The bucket 102 is configured here such that its base lies substantially in the same plane as the remaining portion of the disk-shaped flange 101, which can in particular be easily recognized in FIG. 51. The upper margin of the outer wall of the bucket 102 in accordance with the representation is connected to the remainder of the flange 101 via a connection 103 of stable shape that is configured such that it forms a recess 104 between the bucket 102 and the remainder of the flange 101 that can receive the transverse limbs 42 of the coil cores 4.

The rotor 3 comprises the magnetic core 31 whose jacket 8 as well as a plurality of vanes 9—four vanes 9 here—that are arranged at the axial boundary surface of the magnetically effective core 31 or of its jacket 8 at the top in accordance with the representation. Each vane 9 extends beyond the recess 104 in the radial direction and has a mixing blade 91 that is radially outwardly disposed with respect to the recess 104 and that extends downwardly in accordance with the representation up to just before the flange 101 in the axial direction A. In this embodiment, the vanes 9 are therefore configured such that they, more precisely the mixing blades 91, intersect the magnetic rotor plane C. The center line of each mixing blade 91 that is the center line perpendicular to the axial direction A preferably lies in the magnetic rotor plane C in this respect.

Since this configuration of the stator 2 brings about a particularly high stability of the passive magnetic support, this rotor 3 with the mixing blades 91 can also be supported contactlessly magnetically with respect to the stator 2 in operation.

An opening 105 is preferably provided in the connection 103 through which the fluid or the residues of the fluid can flow out on the emptying of the mixing tank.

Figure 52:
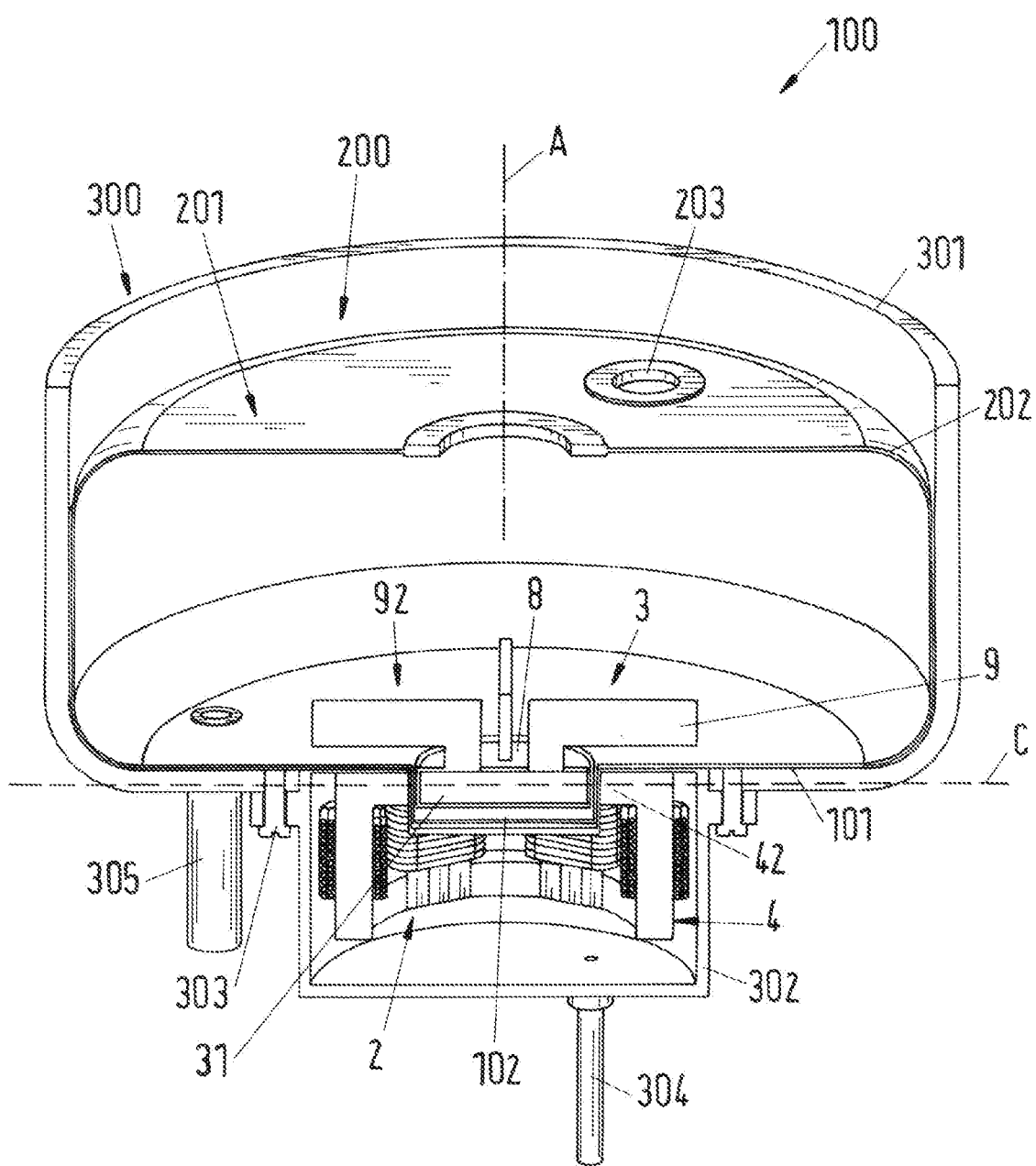
FIG. 52 is a section through a third embodiment of a rotational apparatus in accordance with the invention in an axial direction that comprises a single-use apparatus and a reusable apparatus.

FIG. 52 shows a section in the axial direction A through a third embodiment of a rotational apparatus in accordance with the invention that is configured as a pumping or mixing apparatus 100 for conveying, pumping, mixing or stirring fluids. In the following, only the differences from the above-described embodiments of the rotational apparatus will be looked at. The reference numerals in particular have the same meaning as has already been explained in connection with the embodiments described above. It is understood that all the above explanations also apply in the same manner or in accordingly the same manner to the third embodiment.

In the third embodiment of the rotational apparatus, the stator 2, the rotor 3 and the flange 101 are substantially configured such as is described in connection with FIG. 48 and FIG. 49.

The third embodiment comprises a single-use apparatus 200 that is configured for single use, that is can be used only exactly once in accordance with its intended purpose and then has to be replaced and comprises a reusable apparatus 300 that is configured for multiple use. The single-use apparatus 200 comprises the rotor 3 that has an impeller 92 having the vanes 9 for conveying, pumping, mixing or stirring the fluid or fluids. The reusable apparatus 300 comprises a support tank 301 of stable shape for receiving the rotor 3 and comprises the stator 2 by which the rotor 3 can be contactlessly magnetically drivable and supportable in the operating state, wherein the stator 2 is configured in accordance with the invention.

The single-use apparatus 200 furthermore comprises a flexible mixing tank 201 for receiving the substances to be mixed or conveyed and manufactured from a plastic. The mixing tank 201 preferably comprises a flexible pouch 202, for example a plastic sack or a sack of a synthetic material, which can be folded together so that it takes up as little space as possible during storage. The mixing tank 201 furthermore comprises the flange 101 having the bucket 102 of stable shape at its center. The flange 101 is preferably likewise of stable shape and is connected, for example welded or adhesively bonded, in a fluid-tight manner to the flexible pouch 202 in a manner not shown in any more detail. The rotor 3 is arranged in the mixing tank 201 and is located in the bucket 102 that can then be inserted into the stator 2. The flexible mixing tank 201 of the single-use apparatus 200 is placed into the support tank 301 of the reusable apparatus 300 that supports the mixing tank 201. In this respect, the bucket 102 is inserted into the stator 2 such that the magnetically effective core 31 is arranged completely between the transverse limb 42 of the coil cores 4.

It is understood that the mixing tank 201 and/or the support tank 301 can have further openings, for example for supplying and draining fluids or for receiving sensor or probes, by which properties of the substances located in the mixing tank 201 can be detected. In the configuration in accordance with FIG. 52, for example, an inlet 203 is disposed at the mixing tank 201 through which liquids, gases or other substances can be introduced into the mixing tank 201. An outlet 305 is furthermore provided through which the mixing tank 201 can be emptied or through which substances can be drained out of the mixing tank.

Such configurations of the rotational apparatus with the reusable apparatus 300 and with the single-use apparatus 200 can advantageously be used, for example, in the pharmaceutical industry and in the biotechnological industry. This configuration is specifically suitable for such applications in which a very high degree of purity or sterility of those components is key which come into contact with the substances or fluids to be mixed. This configuration of the rotational apparatus in accordance with the invention can also be formed as a bioreactor or as a fermentor. It is, however, understood, that this configuration can also very generally be a pumping or mixing apparatus with which media or substances can be mixed. These substances can in particular be fluids or solids, preferably powders. Such pumping or mixing apparatus are suitable for mixing liquids among one another and/or for mixing at least one liquid with a powder or other solid and/or for mixing gases with liquids and/or solids.

The support tank 301 has at its base a centrally arranged can 302, which is substantially cylindrical in shape, for receiving the stator 2. The can 302 extends in the direction of its cylinder axis that typically coincides with the axial direction A and is fastened to the base of the support tank 301, for example by screws 303. A feed 304 is disposed at the base of the can 302 and comprises the electrical lines for the supply and regulation of the stator 2. All the electrical connections which are required for the energy supply and the control of the stator 2 as well as for the data exchange between sensors and measuring devices using the control and regulation device, not shown, are combined in this feed 304. The can 302 can be produced from a metallic material or from a plastic.

The assembly of the mixing tank 201 of the single-use apparatus 200 with the rotor 3 contained therein and of the support tank 301 of the reusable apparatus 300 can be carried out extremely simply, fast and in particular without tools. For this purpose, the mixing tank 201, that is typically folded together for storage, together with the rotor 3 located therein is removed from its packaging, is placed into the support tank 301 and the bucket 102 having the rotor 3 disposed therein is placed into the can 302 such that the bucket 102 comes to lie between the transverse limbs 42 of the coil core 4. The rotational apparatus configured as a pumping or mixing apparatus 100 is then already ready for use. After use, the mixing tank 201 with the bucket 102 and the rotor 3 is simply pulled out of the support tank 301. The bucket 102 in this respect simply releases from the can 302. This particularly simple and problem-free connection and separation in particular makes this third embodiment usable for single use, with the mixing tank 201 and the rotor 3 being configured for single use, whereas the support tank 301 and the stator 2 with the can 302 are designed for permanent use or multiple use.

The stator 2 can be molded and thus fixed by a thermally conductive casting compound in the can 302.

Since the bucket 102 of the mixing tank 201 and the flange 101 are preferably configured in a stable shape, but the pouch 202 is flexible, it is advantageous, but not absolutely necessary, to manufacture the bucket 102 and the flange 101 as a separate part that is subsequently connected in a fluid-tight manner to the pouch 202.

It is a further advantageous aspect that the rotor 3 is configured as an integral rotor because it is both the rotor 3 of the electromagnetic drive 1 and the rotor 3 of the magnetic support, that is also the rotor 3 of the mixer. This offers the advantage of a very compact and space-saving design.

When the rotor 3 and the mixing tank 201 are designed for single use, the parts produced from plastic should be manufactured from a commercial plastic which is as inexpensive as possible. A further essential aspect in the configuration for single use is that the single-use parts have to be able to be sterilized for certain areas of application. In this respect, it is particularly advantageous if the single-use parts can be gamma sterilized. In this type of sterilization, the element to be sterilized is acted on by gamma radiation. The advantage of the gamma sterilization, for example in comparison with steam sterilization, in particular lies in the fact that the sterilization can also take place through the packaging. It is in particular a common practice with single-use parts that the parts are brought into their packaging provided for shipping after their manufacture and are then stored for some time before they are delivered to the customer. In such cases, the sterilization takes place through the packaging only shortly before the delivery to the customer, which is not possible with a steam sterilization or with other methods.

It is as a rule not necessary that the single-use parts—such as the mixing tank 201 and the rotor 3—have to be able to be sterilized more than once. This is in particular a great advantage with the gamma sterilization because the application of gamma rays to plastics can result in degradations so that a multiple gamma sterilization can make the plastic unusable.

Since as a rule a sterilization at high temperatures and/or at a high (steam) pressure can be dispensed with for single-use parts, less expensive plastics can be used, for example those which cannot withstand high temperatures or which cannot be exposed to high temperature values and high pressure values a multiple of times.

When taking all these aspects into account, it is therefore preferred in the configuration for single use to use those plastics for the manufacture of the single-use apparatus which can be gamma sterilized at least once. The materials should in this respect be gamma-stable for a dose of at least 40 kGy to allow a single-time gamma sterilization. In addition, no toxic substances should arise in the gamma sterilization. It is additionally preferred for all materials which come into contact with the substances to be mixed to satisfy USP Class VI standards.

The following plastics are, for example, preferred for the manufacture of the flexible pouch 202: Polyethylenes (PE), low density polyethylenes (LDPE), ultra low density polyethylenes (ULDPE), ethylene vinyl acetates (EVA), polyethylene terephthalates (PET), polyvinylchloride (PVC), polypropylenes (PP), polyurethanes (PU), silicones.

The following plastics are, for example, preferred for the manufacture of the bucket 102 and the parts of the rotor 3 comprising plastic, that is the impeller 92, the vanes 9, and the jacket 8: Polyethylenes (PE), polypropylenes (PP), low density polyethylenes (LDPE), ultra low density polyethylenes (ULDPE), ethylene vinyl acetates (EVA), polyethylene terephthalates (PET), polyvinylchloride (PVC), polyvinylidene fluorides (PVDF), acrylonitrile butadiene styrenes (ABS), polyacrylics, polycarbonates (PC).

Less suitable materials or even unsuitable materials for the manufacture of the plastic parts are, for example, the materials polytetrafluroethylenes (PTFE) and perfluoralkoxy polymers (PFA) known under the brand name Teflon. There is namely the risk with these materials on gamma sterilization that hazardous gases arise such as fluorine which can then form toxic or harmful compounds such as hydrofluoric acid (HF). Such materials can naturally be used in such applications in which in especially the rotor 3 is not designed for single use.

The stator 2 and the rotor 3 also together form the electromagnetic rotary drive 1 that is configured as a temple motor and that works, as already explained, in accordance with the principle of a bearingless motor, in the third embodiment. In a bearingless motor, at least three degrees of freedom of the rotor 3, namely its rotation about the desired axis of rotation A and its position in the radial plane, can always be actively magnetically regulated. The degree of freedom of the axial position of the rotor 3 is passively magnetically stabilized, that is no separate axial magnetic bearing or mechanical axial bearing is required. On the one hand, the rotor 3 thereby becomes particularly simple and inexpensive and, on the other hand, the rotor 3 can be simply separated from the stator 2 and from the can 302. Due to the lack of axial bearing components, the rotor 3 together with the bucket 102 can namely simply be separated from the can 302 or from the stator 2.

The magnetically effective core 31 of the rotor 3 is in this respect drawn back as by magnetic spring forces on deflection in the axial direction A by the magnetic fields emanating from the stator 2. These passively magnetic axial restoring forces that stabilize the rotor 3 in its desired position with respect to the axial direction A first increase with the deflection on displacement of the rotor 3 in the axial direction A, reach a maximum on a specific deflection that depends on the geometry of the magnetically effective core 31 of the rotor 3, on the geometry of the end faces 421 of the transverse limbs 42 of the coil cores 4, on the geometry and on the magnetic properties of the permanent magnetic portions 46 and on the air gap between the stator 2 and the rotor 3 and then decrease again. In the configuration of the present invention, the characteristic of the inherent axial passive magnet bearing is selected such that the axial forces which act on the rotor 3 lie beneath the maximum force of the axial passive magnet bearing in the total operating range and such that, in such applications in which the rotor 3 should be able to be simply separated from the stator 2, the maximum force of the axial passive magnet bearing remains small enough for the rotor 3, optionally with the mixing tank 201, to be able to be separated easily and without tools from the stator 2. In this respect, a maximum force of the axial passive magnet bearing of a maximum of 200 Newtons has been found to be still manageable without tools or an auxiliary apparatus for configurations as a pumping or mixing apparatus. With smaller mixing apparatus, a considerably smaller maximum force of the axial passive magnetic bearing is selected to design the insertion and removal in as simple a manner as possible. Values between 10 Newtons and 80 Newtons are typical for mixing apparatus for 50 liters to 1000 liters and for low-viscosity liquids.

A passively magnetic stabilization can likewise be realized for the two remaining degrees of freedom, namely the tilts of the rotor 3 relative to the radial plane, in all embodiments. In such configurations, the regulation of the bearingless motor configured as a temple motor becomes particularly simple and the number of power amplifier channels can also be reduced. This sole passive stabilization of the rotor 3 against tilts, however, only works reliably when certain geometrical conditions are satisfied. If the diameter of the magnetically effective core 31 of the rotor 3 is d and the level of the magnetically effective core 31 in the axial direction is HR, the diameter has to be at least 2.6 times higher than the height HR. The condition $d>2.6*HR$ should thus be satisfied, that is the diameter d should be more than 2.6 times the height HR.

If the rotor 3 is configured as an external rotor (see e.g. FIG. 54), the diameter of the magnetically effective core 31 in this geometrical relationship is to be replaced by the inner diameter of the magnetically effective core 31, i.e. the condition is then that the inner diameter d of the magnetically effective core 31 is at least 2.6 times greater than the height HR. The condition $d>2.6*HR$ should then be satisfied, that is the inner diameter d should be more than 2.6 times the height HR.

For this reason, it is also preferred for the rotational apparatus in accordance with the invention if the rotor 3 is stabilized purely passively magnetically with respect to tilts toward the radial plane (two degrees of freedom), if the diameter of the rotor 3 (or the inner diameter in a configuration as an external rotor) is at least 2.6 times as large as the height HR of the magnetically effective core 31 in the axial direction A.

In embodiments of the invention in which this geometrical condition is no longer satisfied, the rotor 3 can be stabilized or regulated with respect to these tilts by other suitable measures.

Figure 53:
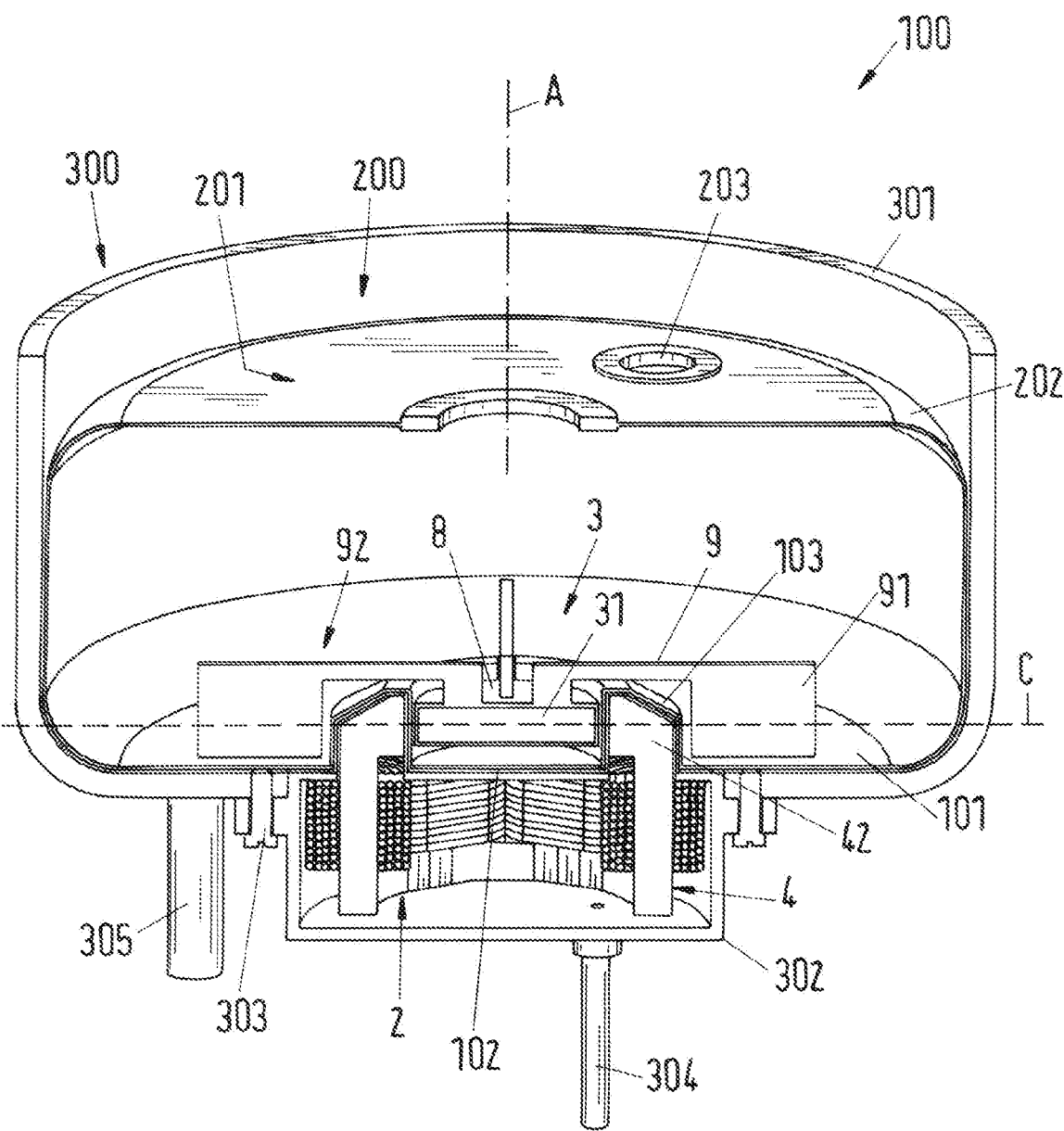
FIG. 53 is a section through a fourth embodiment of a rotational apparatus in accordance with the invention in an axial direction that comprises a single-use apparatus and a reusable apparatus.

FIG. 53 shows a section in the axial direction A through a fourth embodiment of the rotational apparatus in accordance with the invention that is configured as a pumping or mixing apparatus 100 for conveying, pumping, mixing or stirring fluids. In the following, only the differences from the above-described embodiments will be looked at. The reference numerals in particular have the same meaning as has already been explained in connection with the first, second and third embodiments. It is understood that all the above-described variants, embodiments and measures can also be realized in the same manner or in accordingly the same manner in the fourth embodiment.

The fourth embodiment substantially corresponds to the third embodiment, but in the fourth embodiment the stator 2 and the rotor 3 are configured such as is explained in connection with FIGS. 50 and 51.

Figure 54:
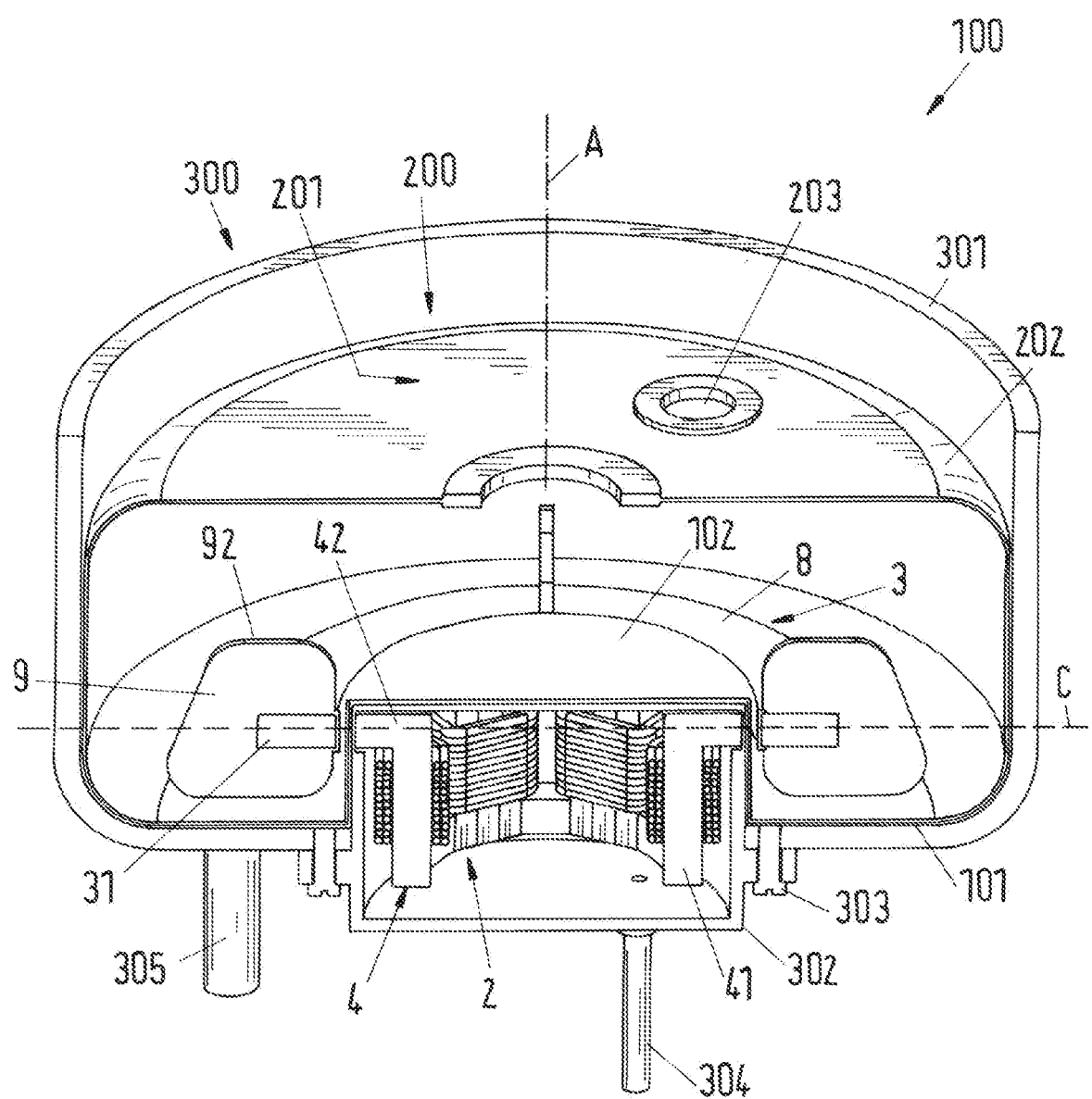
FIG. 54 is a section through a fifth embodiment of a rotational apparatus in accordance with the invention in an axial direction that comprises a single-use apparatus and a reusable apparatus.

FIG. 54 shows a section in the axial direction A through a fifth embodiment of the rotational apparatus 100 in accordance with the invention. In the following, only the differences from the above-described embodiments will be looked at. The reference numerals in particular have the same meaning as has already been explained in connection with the preceding embodiments. It is understood that all the above explanations also apply in the same manner or in accordingly the same manner to the fifth embodiment.

The fifth embodiment is also configured as a pumping or mixing apparatus 100 for conveying, pumping, mixing or stirring fluids. Preferably, but not necessarily, the fifth embodiment also comprises components for single use, that is it comprises the single-use apparatus 200 that is configured for single use and the reusable apparatus 300 that is configured for multiple use. The single-use apparatus 200 comprises the rotor 3 having the impeller 92 and the vanes 9 for conveying, pumping, mixing or stirring the fluid or fluids and comprise the flexible mixing tank 201 having the flexible pouch 202. The reusable apparatus 300 comprises the support tank 301 of stable shape for receiving the mixing tank 201 and comprises the stator 2 by which the rotor 3 can be contactlessly magnetically drivable and supportable in the operating state.

In the fifth embodiment, the rotor 3 is configured as an external rotor, that is the rotor 3 is arranged radially outwardly disposed about the transverse limbs 42 of the coil cores 4 and the transverse limbs 2 extend outwardly in the radial direction and thus toward the rotor 3 such that the end faces 421 of the coil cores 4 are arranged radially outwardly disposed.

The stator 2 is configured, for example, such as is explained in connection with FIGS. 18 and 19. The magnetically effective core 31 of the rotor 3 is also configured, for example, such as shown in FIGS. 18 and 19. The magnetic core 31 is surrounded by the jacket 8 that, as already explained above, is preferably composed of plastic. The magnetically effective core 31 can, for example, be molded with the plastic to form the jacket 8. The rotor 3 furthermore comprises the impeller 92 having a plurality of vanes 9—four here—with which the fluid or the substances are mixed or pumped or stirred. The vanes 9 or the impeller 91 are/is preferably manufactured from plastic and can be manufactured in one piece with the jacket 8 or as separate components that are subsequently fixed to the jacket 8, for example by adhesive bonding or welding. The vanes 9 are preferably configured and arranged such that the magnetic core 31 extends approximately centrally through each vane 9 with respect to the axial direction A. The forces transmitted onto the rotor 3 by the vanes 9 during the operation are hereby imparted both beneath and above the magnetic rotor plane 3, which is advantageous with respect to the magnetic stabilization of the rotor position.

In the embodiment as an external rotor described here, the bucket 102 of stable shape is arranged on the flange 101 such that it is pushed out inwardly with respect to the mixing tank 201, that it projects into the mixing tank 201. The rotor 3 is then arranged such that the magnetic core 31 extends disposed radially outwardly about the bucket 102 and surrounds it. It is possible in this manner to position the stator 2 such that the transverse limbs 42 of the coil cores 4 are disposed in the bucket 102 and the end faces 421 of the transverse limbs 42 are thus arranged disposed opposite the magnetically effective core 31. In this respect, the diameter of the bucket 102 is dimensioned with respect to the radial direction such that the bucket 102 only surrounds the transverse limbs 42 with a very small clearance or with no clearance, but can be separated from the stator 2 without problem. The can 302 that receives the stator 2 overlaps the bucket 102 with respect to the axial direction A, that is it extends into the bucket 102 and ends just above the transverse limbs 42.

Figure 55:
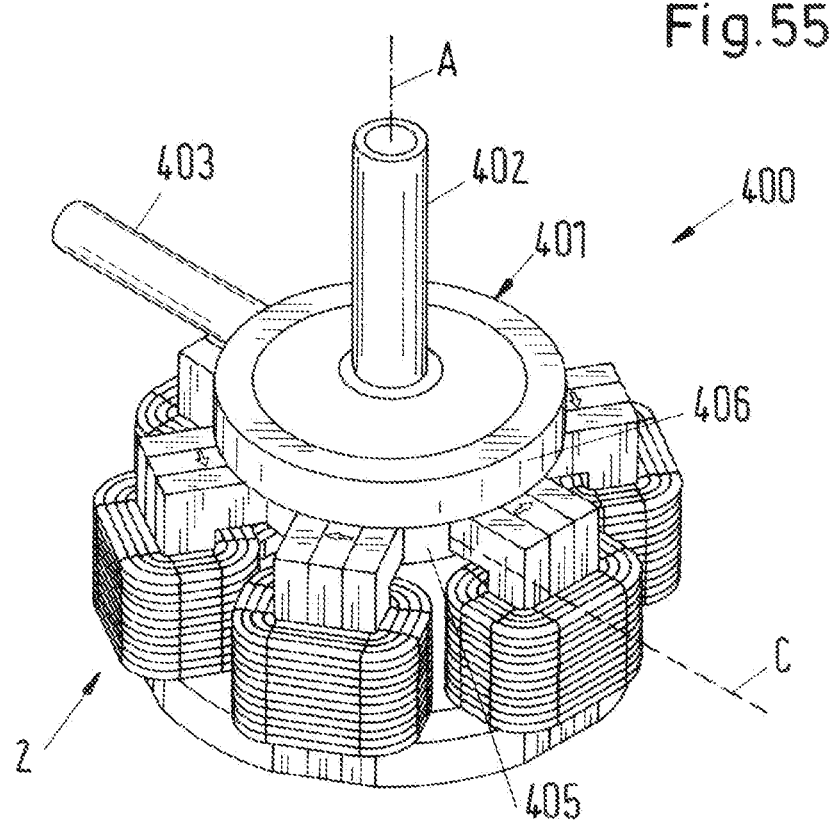
FIG. 55 is a perspective representation of a sixth embodiment of a rotational apparatus in accordance with the invention that is configured as a pumping apparatus.
Figure 56:
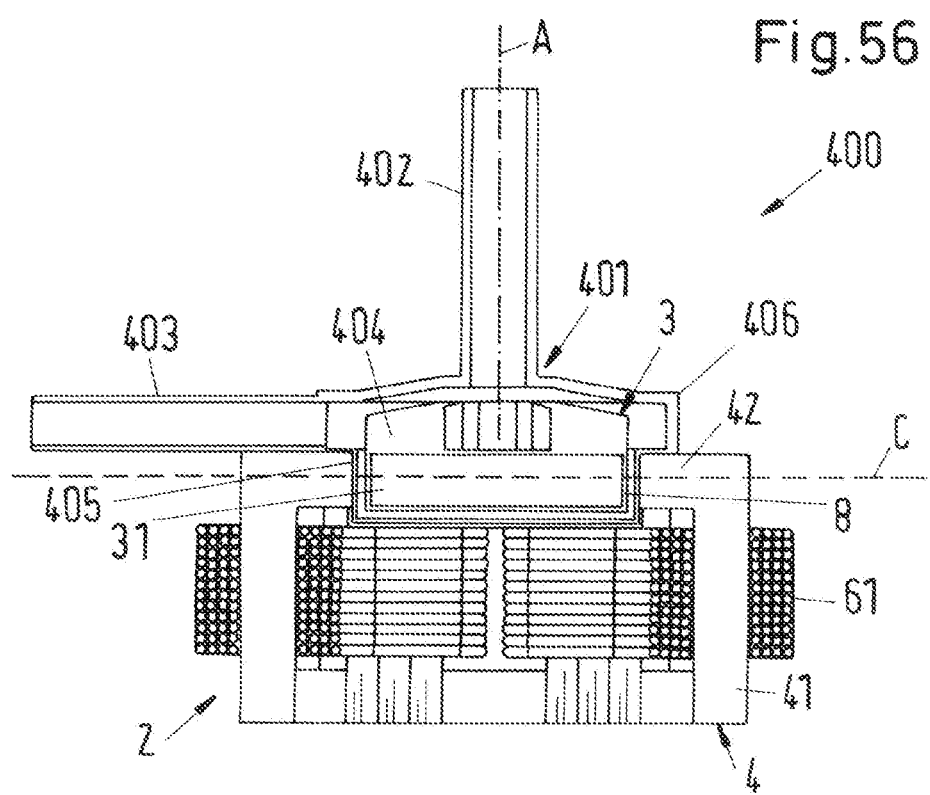
FIG. 56 is a section through the sixth embodiment of FIG. 55 in an axial direction.

FIG. 55 shows a perspective representation of a sixth embodiment of the rotational apparatus in accordance with the invention. For better understanding, FIG. 56 shows a section through the sixth embodiment in the axial direction. In the following, only the differences from the above-described embodiments will be looked at. The reference numerals in particular have the same meaning as has already been explained in connection with the preceding embodiments. It is understood that all the above explanations also apply in the same manner or in accordingly the same manner to the sixth embodiment.

The sixth embodiment is configured as a pumping apparatus 400 for pumping or conveying a fluid and comprises the stator 2 that is, for example, configured such as is explained in connection with FIG. 7 and FIG. 8.

The pumping apparatus 400 furthermore comprises a pump housing 401 that is preferably manufactured from a plastic. The pump housing 401 has an inlet 402 for the fluid to be conveyed that extends in the axial direction A, that is arranged centrally at the middle of the pump housing 401 and that is configured as a cylindrical tube in the axial direction A and has an outlet 403 for the fluid to be conveyed that extends in the radial direction and that is configured as a cylindrical tube. The rotor 3 that is configured as an impeller and that comprises the magnetically effective core 31 and a plurality of vanes 404 to convey the fluid from the inlet 402 to the outlet 403 are disposed in the pump housing 401. The vanes 404 are arranged above the magnetically effective core 31 in accordance with the illustration with respect to the axial direction A. The pumping apparatus 400 is here therefore configured as a centrifugal pump. Other configurations, e.g. as an axial pump or as a helico-axial pump, are naturally also possible.

The magnetically effective core 31 of the rotor 3 is surrounded by the jacket 8 that, exactly like the vanes 404, is preferably produced from plastic. The pump housing 401 comprises a lower portion 405 that surrounds the magnetically effective core 31 of the rotor 3 and comprises an upper portion 406 that is axially adjacent thereto and that surrounds the vanes 404 of the rotor. Both portions 405 and 406 have a substantially circular cross-sectional surface perpendicular to the axial direction, with the lower portion 405 having a smaller diameter than the upper portion 406. The diameter of the lower portion 405 is dimensioned in this respect such that it can be inserted between the transverse limbs 42 of the coil cores 4 with as small a clearance as possible and can be released from the stator 2 again in a simple manner. The diameter of the upper portion 406 is dimensioned such that it overlaps the transverse limbs 42 with respect to the radial direction such that it can lie on the transverse limbs 42.

When the pump housing 401 having the rotor 3 arranged therein is inserted into the stator 2, the transverse limbs 42 of the coil cores 4 surround the lower portion 405 of the pump housing 401 in which the magnetically effective core 31 is located such that the magnetic rotor plane C is disposed in the radial plane and the magnetically effective core 31 lies completely between the end faces 421 of the transverse limbs 42 with respect to the axial direction A. The rotor 3 is thus contactlessly magnetically drivable and contactlessly magnetically supportable with respect to the stator in the operating state.

The upper portion 406 of the pump housing 401 is located directly above the transverse limbs 42 of the coil cores 4 with respect to the axial direction A. The outlet 403 that open into this upper portion 406 is disposed at the same height as the vanes 404 with respect to the axial direction A, which is in particular advantageous with respect to the hydrodynamic forces that act on the rotor 3 in operation. For these hydrodynamic forces are distributed as evenly as possible over the rotor 3. Such a relative arrangement between the outlet 403 and the vanes 404 is in particular possible by the configuration of the rotary drive 1 as a temple motor because here the transverse limbs 42 are free of windings that would make such an arrangement of the outlet 403 at least considerably more difficult.

The rotational apparatus configured as a pumping apparatus 400 can also be configured in an advantageous manner with components for single use and can have the single-use apparatus 200 and the reusable apparatus 300. For such applications, the single-use apparatus 200 preferably comprise the pump housing 401 and the rotor 3 arranged therein as single-use parts for single use that can therefore be used only once in accordance with their intended purpose and then have to be replaced with a new, unused part for the next application. The reusable apparatus 300 comprises the stator 2 in this configuration.

Due to the absence of mechanical bearings, the pumping apparatus 400 is in particular suitable for such applications in which very sensitive substances are conveyed, for example blood pumps, or on which very high demands are made on purity, for example in the pharmaceutical industry or in the biotechnological industry, or with which abrasive substances are conveyed which would very quickly destroy mechanical bearings, for example pumps for slurry in the semiconductor industry.

It is also an advantageous aspect with the pumping apparatus 400 that the rotor 3 is configured as an integral rotor because it is both the rotor 3 of the electromagnetic drive 1 and the rotor 3 of the magnetic support and the rotor 3 of the pumping apparatus 400 by which the fluid to be conveyed is pumped. This offers the advantage of a very compact and space-saving design.

The invention claimed is:

1. An electromagnetic rotary drive configured as a temple motor, comprising:
   a rotor configured to be contactlessly magnetically drivable, and is coil-free and free of permanent magnets, the rotor comprising a magnetically effective core; and
   a stator configured to contactlessly magnetically drive the rotor about an axis of rotation in an operating state, the stator having a plurality of coil cores, each of the plurality of coil cores comprising a bar-shaped longitudinal limb extending from a first end in a direction in parallel with a desired axis of rotation up to a second end, the first ends being configured to be connected by a reflux, and a plurality of windings configured to generate an electromagnetic rotational field, each of the plurality of windings surrounding one of the longitudinal limbs, and the coil cores comprising a plurality of permanent magnets capable of generating a permanent magnetic pre-magnetization flux, and
   each coil core comprising a transverse limb arranged at the second end of the longitudinal limb and extending in a radial direction perpendicular to an axial direction defined by the axis of rotation and a permanent magnetic portion extending from the first end up to the second end of the longitudinal limb and two permanent magnet-free portions that each extend from the first end up to the second end, with the permanent magnetic portion being arranged between the two permanent magnet-free portions.

2. The rotary drive in accordance with claim 1, wherein the stator is a bearing and drive stator by which the rotor is contactlessly magnetically supported with respect to the stator in the operating state.

3. The rotary drive in accordance with claim 2, wherein end faces of the transverse limbs of the coil cores facing the rotor have a height in an axial direction that is respectively larger than an axial height of the magnetically effective core of the rotor.

4. The rotary drive in accordance with claim 1, wherein the permanent magnetic portion and the two permanent magnet-free portions of the coil core each extend through the transverse limb, and the permanent magnetic portion is arranged between the two permanent magnet-free portions in the transverse limb.

5. The rotary drive in accordance with claim 1, wherein the permanent magnetic portions are each polarized perpendicular to the radial direction and perpendicular to the axial direction, with the permanent magnets of adjacent coil cores each being polarized in opposite directions.

6. The rotary drive in accordance with claim 1, wherein the permanent magnet-free portions of the coil cores are each manufactured as in bundled laminate form from elements, the elements being stacked in a peripheral direction of the rotor.

7. The rotary drive in accordance with claim 1, wherein the stator has an even number of coil cores.

8. The rotary drive in accordance with claim 7, wherein the stator has 6, 8 or 12 coil cores.

9. The rotary drive in accordance with claim 1, wherein the windings comprise drive coils configured to generate an electromagnetic drive field for the rotor and comprise control coils separate therefrom configured to set a transverse force acting on the rotor in the radial direction.

10. The rotary drive in accordance with claim 1, wherein the magnetically effective core of the rotor is configured in disk form or ring form and has a radially outer boundary surface, and the coil cores are evenly spaced along the radially outer boundary surface in the radial direction in a centered state of the rotor.

11. A rotational apparatus for conveying, pumping, mixing or stirring fluid, comprising:
   the electromagnetic rotary drive in accordance with claim 1.

12. The rotational apparatus in accordance with claim 11, further comprising a single-use apparatus configured for single use; and a reusable apparatus configured for multiple use, the single-use apparatus comprising the rotor having a plurality of vanes configured to convey, pump, mix of stir the fluid or fluids, and the reusable apparatus comprising a support tank configured to receive the rotor and the stator configured to contactlessly magnetically drive and support the rotor in the operating state, the stator comprising at the plurality of permanent magnet magnets configured to generate the permanent magnetic pre-magnetization flux and comprising the plurality of windings configured to generate the electromagnetic flux, and the permanent magnetic pre-magnetization flux and the electromagnetic flux together are configured to drive and support the rotor.

13. A stator for an electromagnetic rotary drive that is a temple motor, the stator capable contactlessly magnetically driving a rotor about an axis of rotation in the operating state, the stator comprising
   a plurality of coil cores, each of the plurality of coil cores comprising a bar-shaped longitudinal limb extending from a first end in a direction in parallel with the axis of rotation up to a second end, the first ends being configured to be connected by a reflux; and
   a plurality of windings configured to generate an electromagnetic rotational field, each of the plurality of windings surrounding one of the longitudinal limbs, the plurality of coil cores comprises a plurality of permanent magnets capable of generating a permanent magnetic pre-magnetization flux, each coil core of the plurality of coil cores comprises a permanent magnetic portion extending from the first end up to the second end of the longitudinal limb and comprises two permanent magnet-free portions each extending from the first end up to the second end, the permanent magnetic portion being arranged between the two permanent magnetic-free portions.

14. The stator in accordance with claim 13, wherein the stator is a bearing and drive stator configured to contactlessly magnetically support the rotor with respect to the stator in the operating state.

15. A rotational apparatus for conveying, pumping, mixing or stirring fluid, comprising:
the stator in accordance with claim 14.

* * * * *